United States Patent [19]

Wu et al.

[11] Patent Number: 4,735,966
[45] Date of Patent: Apr. 5, 1988

[54] NOVEL SUBSTITUTED (4.2.0)BICYCLOOCTANE DERIVATIVES WITH VALUABLE THERAPEUTIC PROPERTIES

[75] Inventors: Helen Y. Wu, San Jose; Walter Kurz, Mountain View, both of Calif.

[73] Assignee: Syntex (U.S.A.) Inc., Palo Alto, Calif.

[21] Appl. No.: 900,025

[22] Filed: Aug. 25, 1986

[51] Int. Cl.$^4$ ............... A61K 31/045; A61K 31/11; A61K 31/19; A61K 31/215

[52] U.S. Cl. ............ 514/510; 514/569; 514/572; 514/700; 514/703; 514/729; 514/824; 560/56; 560/116; 560/119; 562/466; 562/498; 562/501; 568/441; 568/445; 568/808; 568/819

[58] Field of Search ............ 560/56, 116, 119; 562/466, 498, 501; 568/441, 445, 808, 819; 514/510, 569, 572, 700, 703, 729, 824

[56] References Cited

U.S. PATENT DOCUMENTS 4,192,891 3/1980 Haslanger ............ 562/501 X
4,608,388 8/1986 Kluge et al. ............ 514/510
4,678,805 7/1987 Kluge et al. ............ 514/510

Primary Examiner—Donald B. Moyer
Assistant Examiner—Patricia M. Scott
Attorney, Agent, or Firm—Ellen J. Wise; Tom M. Moran; Brian Lewis

[57] ABSTRACT

Compounds useful in treating cardiovascular disorders such as thrombosis, hypertension and atherosclerosis are depicted in formulas (1), (2) and (3):

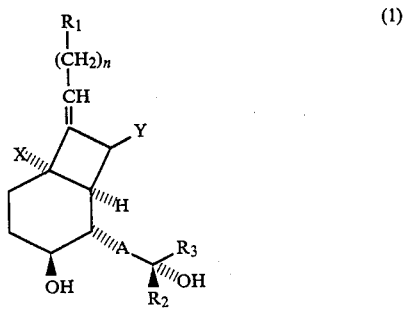

(1)

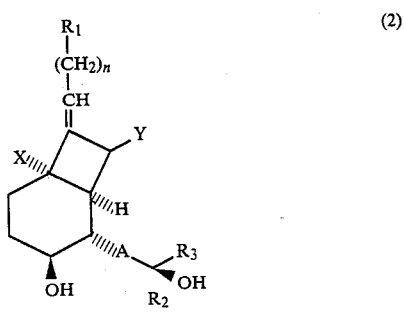

(2)

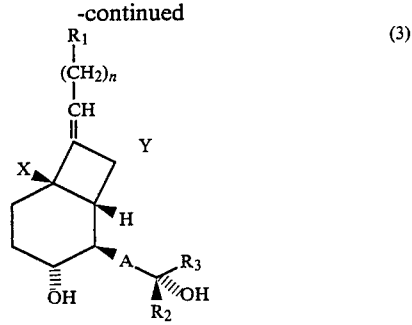

(3)

wherein:
A is —C≡C—, trans —HC=CH—, —CH$_2$CH$_2$— or —CH=CHCH$_2$—;
X is lower alkoxy, hydroxy, or (2,2,2)-trifluoroethoxy;
Y is hydrogen, exo-(lower alkyl) or endo-(lower alkyl);
is an integer of 2–4;
R$_1$ is —CH$_2$OH, —CHO, —CO$_2$R or —CO$_2$H, and the olefin formed by the R$_1$(CH$_2$)$_n$CH= moiety is either (E) or (Z);
R$_2$ is hydrogen or methyl, or optionally —CH=CH$_2$ when A is —CH=CHCH$_2$—; and
R$_3$ is linear or branched alkyl, alkenyl or alkynyl having 5–10 carbon atoms,

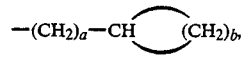

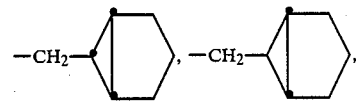

—(CH$_2$)$_m$-phenyl or CH$_2$O-phenyl;
in which each phenyl may be optionally substituted with lower alkyl, lower alkoxy, trifluoromethyl, or halogen;
in which:
a is an integer of 0, 1 or 2;
b is an integer of 3–7;
m is an integer of 0, 1 or 2; and
R is

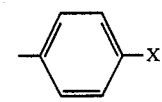

wherein x is $$-\overset{O}{\underset{\|}{C}}-CH_3, \quad -NH\overset{O}{\underset{\|}{C}}CH_3, \quad -\overset{O}{\underset{\|}{C}}-C_6H_5, \quad -NH\overset{O}{\underset{\|}{C}}-C_6H_5, \text{ or}$$

$$-NH\overset{O}{\underset{\|}{C}}N(R_4)_2;$$

in which each R$_4$ is independently hydrogen or lower alkyl having 1–6 carbon atoms,
and the pharmaceutically acceptable, non-toxic salts and esters thereof.

40 Claims, No Drawings

NOVEL SUBSTITUTED (4.2.0)BICYCLOOCTANE DERIVATIVES WITH VALUABLE THERAPEUTIC PROPERTIES

BACKGROUND OF THE INVENTION

1. Field of the Invention

This invention concerns novel derivatives of certain bicyclo[4.2.0]octanes and pharmaceutically acceptable salts and esters thereof, their use in treating cardiovascular disorders, pharmaceutical compositions containing these compounds, and methods of preparing such compounds.

2. Related Disclosures

Bicyclo[4.2.0]oct-2-en-7-one is readily prepared from 1,3-cyclohexadiene (*Tetrahedron*, 27:615, 1971). This has been used as an intermediate in a prostaglandin synthesis (*Tetrahedron Lett.*, 3091, 1973).

Several prostaglandin analogues are known which contain bicyclic all-carbon skeletons. Carbacyclin contains a bicyclo[3.3.0]octane skeleton, and is described in several publications (*J. Chem. Soc., Chem. Commun.*, 1067, 1978, *Tetrahedron Lett.*, 3743, 1978; *Tetrahedron Lett.*, 433, 1979; *Tetrahedron Lett.*, 2807, 1979; *J. Org. Chem.* 44:2880, 1979) and patents (Belgium Pat. No. 874, 135; British Pat. No. 2,014,143; French Pat. No. 2,424,908; Ger. Offen. 2,904,655; Japanese Pat. No. K79,117,450; Netherthland Patent Application Nos. 7,901,076 and 8,003,579; S. African Pat. No. 79 00 176). Numerous analogues of carbaprostacyclin are described (U.S. Pat. No. 4,306,076; Ger. Offen. No. 3,146,278; Ger. Offen. No. 3,204,443; *Prostaglandins, Leukotrienes Med.*, 9:307, 1982; *J. Org. Chem.* 48, 5341, 1983; *Tetrahedron Lett.* 3493, 1983; *Biochem. Pharmacol.* 32:2405, 1983; *Prostaglandins, Leukotrienes. Med.* 11:391, 1983). 9-Substituted analogs of carbacyclin are described in U.S. Pat. No. 4,487,960 and U.S. Pat. No. 4,487,961.

Synthetic prostaglandins (homo $PGE_2$ and homo $PGF_{2\alpha}$) have been prepared with the hydroxyl function and lower side chain trans-opposed in a 6-membered ring (*Tetrahedron Lett.*, 3327, 1971).

The preparation of novel unsubstituted bicyclo[4.2.0]octane derivatives and their use in treating cardiovascular disorders was disclosed in U.S. patent application Ser. No. 716,872, filed 03/27/85, the relevant portions of which are incorporated by reference herein.

SUMMARY OF THE INVENTION

One aspect of the present invention relates to compounds of the formulas (1), (2) and (3)

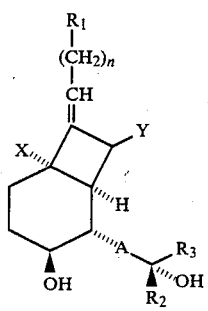
(1)

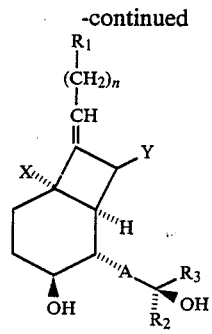
(2)

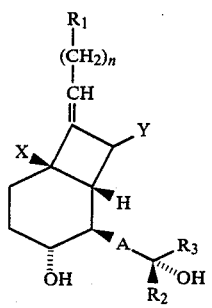
(3)

wherein:
A is $-C\equiv C-$, trans $-HC=CH-$, $-CH_2CH_2-$ or $-CH=CHCH_2-$;
X is lower alkoxy, hydroxy, or (2,2,2)-trifluoroethoxy;
Y is hydrogen, exo-(lower alkyl) or endo-(lower alkyl);
n is an integer of 2–4;
$R_1$ is $-CH_2OH$, $-CHO$, $-CO_2R$ or $-CO_2H$, and the olefin formed by the $R_1(CH_2)_nCH=$ moiety is either (E) or (Z);
$R_2$ is hydrogen or methyl, or optionally $-CH=CH_2$ when A is $-CH=CHCH_2-$; and
$R_3$ is linear or branched alkyl, alkenyl or alkynyl having 5–10 carbon atoms,

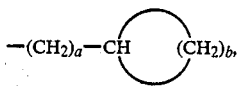

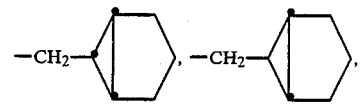

$-(CH_2)_m$-phenyl or $CH_2O$-phenyl
in which each phenyl may be optionally substituted with lower alkyl, lower alkoxy, trifluoromethyl, or halogen.
in which:
a is an integer of 0, 1 or 2;
b is an integer of 3–7;
m is an integer of 0, 1 or 2; and
R is

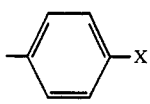

wherein X is

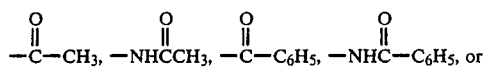

in which each $R_4$ is independently hydrogen or lower alkyl having 1–6 carbon atoms,
and the pharmaceutically acceptable non-toxic salts and esters thereof.

Another aspect of this invention is a method of treating cardiovascular disorders in mammals by administering a therapeutically effective amount of a compound of formula (1), (2), or (3) or a pharmaceutically acceptable salt or ester thereof.

Yet another aspect of the invention is a pharmaceutical composition containing at least one suitable pharmaceutical excipient and a compound of formula (1), (2) or (3), or a pharmaceutically acceptable salt and ester thereof.

Lastly, another aspect of the invention is a process for preparing compounds of formulas (1), (2) or (3), and their corresponding pharmaceutically acceptable, non-toxic salts and esters, as discussed below.

DETAILED DESCRIPTION OF THE INVENTION

Definitions

As used herein, the pharmaceutically acceptable, non-toxic salts of the compounds of formula (1), (2) or (3) are carboxylic acid salts obtained by reaction of the COOH moiety in formula (1), (2) or (3) with a suitable organic or inorganic base. Specific preparations are discussed hereinafter.

The pharmaceutically acceptable carboxylic esters corresponding to the acids of formula (1), (2) or (3) are prepared by conventional methods from the acid, e.g. by reaction with the appropriate diazoalkane, or reaction of an alcohol or phenol with an activated derivative of the acid optionally employing a condensing agent such as dicyclohexyl carbodiimide, by reaction of a salt with an appropriate alkylating agent, or by ester exchange from an existing ester. Specific preparations are described in the procedures and examples below.

The term "alkyl" refers to and includes saturated branched and straight chain monovalent hydrocarbon radicals containing the number of carbons indicated. Typical alkyl groups include methyl, ethyl, propyl, isopropyl, butyl, tertiary butyl, neopentyl, isopentyl, hexyl, octyl, nonyl, isodecyl, 6-methyldecyl.

"Cycloalkyl" as used herein means a monovalent saturated monocyclic hydrocarbon radical containing 3–8 carbon atoms, such as cyclopropyl, cyclobutyl, cyclopentyl, cyclohexyl, cycloheptyl and cyclooctyl.

The term, "lower alkyl" refers to a branched or unbranched saturated monovalent hydrocarbon chain of 1–4 carbons, such as, for example, methyl, ethyl, n-propyl, i-butyl and the like.

The term, "alkenyl" refers to a branched or unbranched saturated monovalent hydrocarbon chain containing a double bond, such as, for example, pent-2-en-1-yl, 4-methylpent-3-en-1-yl, hex-4-en-1-yl, 2,6-dimethylhept-5-en-1-yl, and the like.

The term, "alkynyl" refers to a branched or unbranched saturated monovalent hydrocarbon chain containing a triple bond, such as, for example, pent-2-yn-1-yl, 4-methylpent-3-yn-1-yl, hex-4-yn-1-yl, hex-4-yn-2-yl, hept-4-yn-2-yl, and the like.

The term "alkoxy" refers to the radical —O—alkyl wherein "alkyl" is as defined above. This includes radicals such as methoxy, ethoxy, 2-propoxy, butoxy, 3-pentoxy and the like.

"Lower alkoxy" means the group —O—(lower alkyl) wherein lower alkyl is as defined above.

"Halo" as used herein denotes fluoro, chloro, bromo, or iodo.

"Phenyl" as used herein encompasses all possible isomeric phenyl radicals optionally monosubstituted with a substituent selected from the group consisting of lower alkyl, lower alkoxy, hydroxy, trifluoromethyl and halogen.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The numbering system for the bicyclo[4.2.0]octane system shown in the scheme illustration below is used in naming the intermediates and product compounds of the invention.

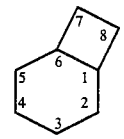

The absolute stereochemistry at carbons 1, 2, 3 and 6, and 3' of the side chain attached to carbon 2 are specified according to the Cahn-Ingold-Prelog R-S system. When the compound is a pure enantiomer, the stereochemistry at each chiral carbon is specified by either R or S. When a compound is a racemic mixture the stereochemistry at each chiral carbon is specified by either RS or SR by reference to a single enantiomer of the racemate. In this manner relative stereochemistry is conveyed unambiguously. The stereochemistry at carbon 8 is specified as an exo or endo isomer. When the substituent at carbon 8 is cis to the ring junction substituents (at carbons 1 and 6) it is specified as an exo-isomer. When the substituent at carbon 8 is trans to the ring junction substituents it is specified as an endo-isomer. Olefin stereochemistry is specified by the IUPAC E-Z system. Classical nomenclature is used to name a compound having a triple bond as alkynyl; and two bonds emanating from the same atom as -ylidene. Exemplary names are given in the "Preferred Embodiments" section of this application.

PREFERRED EMBODIMENTS OF THE INVENTION

Among the family of compounds of the present invention, a preferred group includes those compounds of formula (1), (2) and (3) in which the olefin formed by the $R_1(CH_2)_nCH=$ moiety is (Z). Within this group a preferred subgroup includes the compounds represented by the formulas (1) and (2).

One preferred class within this subgroup include (a) compounds in which X is lower alkoxy, n is 2 or 3, especially those in which A is $C\equiv C$. More preferred embodiments of this class include those compounds where X is methoxy, $R_2$ is hydrogen and $R_3$ is

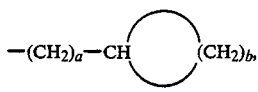

especially where a is zero and b is 5. Of these, an especially preferred subclass includes those compounds in which $R_1$ is $-CO_2H$ and Y is hydrogen. Another especially preferred subclass includes those compounds where Y is exo-methyl or endo-methyl and $R_1$ is $-CO_2H$.

A second preferred class includes (b) compounds in which X is lower alkoxy, n is 2 or 3 and A is trans $-CH=CH-$. More preferred embodiments include those compounds where X is methoxy, Y and $R_2$ are both hydrogen, and $R_3$ is

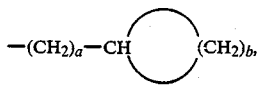

especially where a is 0 and b is 5. Of these, especially preferred are those compounds in which $R_1$ is $-CO_2H$.

A third preferred class includes (c) those compounds in which X is methoxy and A is $-CH_2CH_2-$.

Still another preferred class includes (d) those compounds in which X is methoxy and A is $-CH=CHCH_2-$.

The foregoing statement of the preferred embodiments of the invention includes the pharmaceutically acceptable salts and esters, as well as the free bases of the compounds referred to above or named below. At the present time, the most preferred compounds of this invention are:

(Z)-(3'S,1S,2R,3S,6S)-4-[2-(3'-hydroxy-3'-cyclohexyl-prop-1'-ynyl)-3-hydroxy-6-methoxybicyclo[4.2.-0]oct-7-ylidene]butyric acid;

(Z)-(3'S,1S,2R,3S,6S)-5-[2-(3'-hydroxy-3'-cyclohexyl-prop-1'-ynyl)-3-hydroxy-6-methoxybicyclo[4.2.-0]oct-7-ylidene]pentanoic acid;

(Z)-(3'S,1S,2R,3S,6S)-4-[2-(3'-hydroxy-3'-cyclohexyl-prop-1'-ynyl)-3-hydroxy-6-methoxy-8-exo-methyl-bicyclo[4.2.0]oct-7-ylidene]butyric acid;

(Z)-(3'S,1S,2R,3S,6S)-4-[2-(3'-hydroxy-3'-cyclohexyl-prop-1'-ynyl)-3-hydroxy-6-methoxy-8-endo-methyl-bicyclo[4.2.0]oct-7-ylidene]butyric acid;

(Z)-(3'S,1S,2R,3S,6S)-5-[2-(3'-hydroxy-3'-cyclohexyl-prop-1'-ynyl)-3-hydroxy-6-methoxy-8-exo-methyl-bicyclo[4.2.0]oct-7-ylidene]pentanoic acid;

(Z)-(3'S,1S,2R,3S,6S)-5-[2-(3'-hydroxy-3'-cyclohexyl-prop-1'-ynyl)-3-hydroxy-6-methoxy-8-endo-methyl-bicyclo[4.2.0]oct-7-ylidene]pentanoic acid;

(Z)-(3'S,1S,2S,3S,6S)-4-[2-(3'-hydroxy-3'-cyclohexyl-prop-(1'E)-enyl)-3-hydroxy-6-methoxybicyclo[4.2.-0]oct-7-ylidene]butyric acid; and (Z)-(3'R,1S,2S,3S,6S)-4-[2-(3'-hydroxy-3'-cyclohexyl-prop-(1'E)-enyl)-3-hydroxy-6-methoxybicyclo[4.2.-0]oct-7-ylidene]butyric acid.

METHODS OF PREPARATION

1. Compounds of Formula (1), (2) or (3) wherein $R^1$ is $-CO_2H$ (a) Where A is $-C\equiv C-$ and $R_1$ is $-CO_2H$ Compounds of Formula (1), (2) or (3) where A is $-C\equiv C-$ and $R_1$ is $-CO_2H$ are prepared as shown in Reaction Scheme 1.

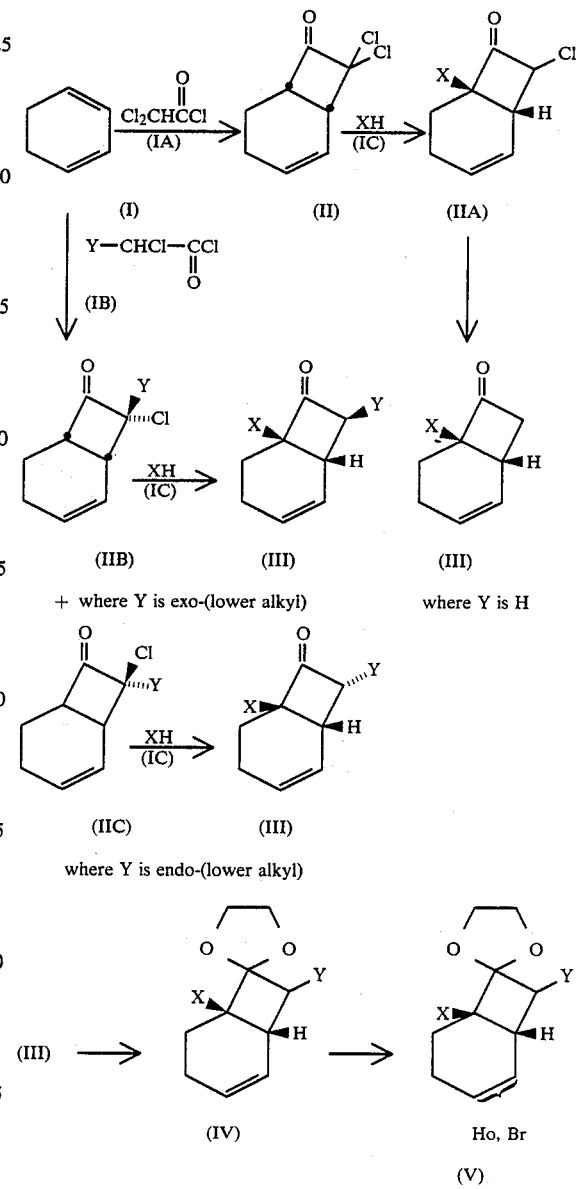

-continued
REACTION SCHEME 1

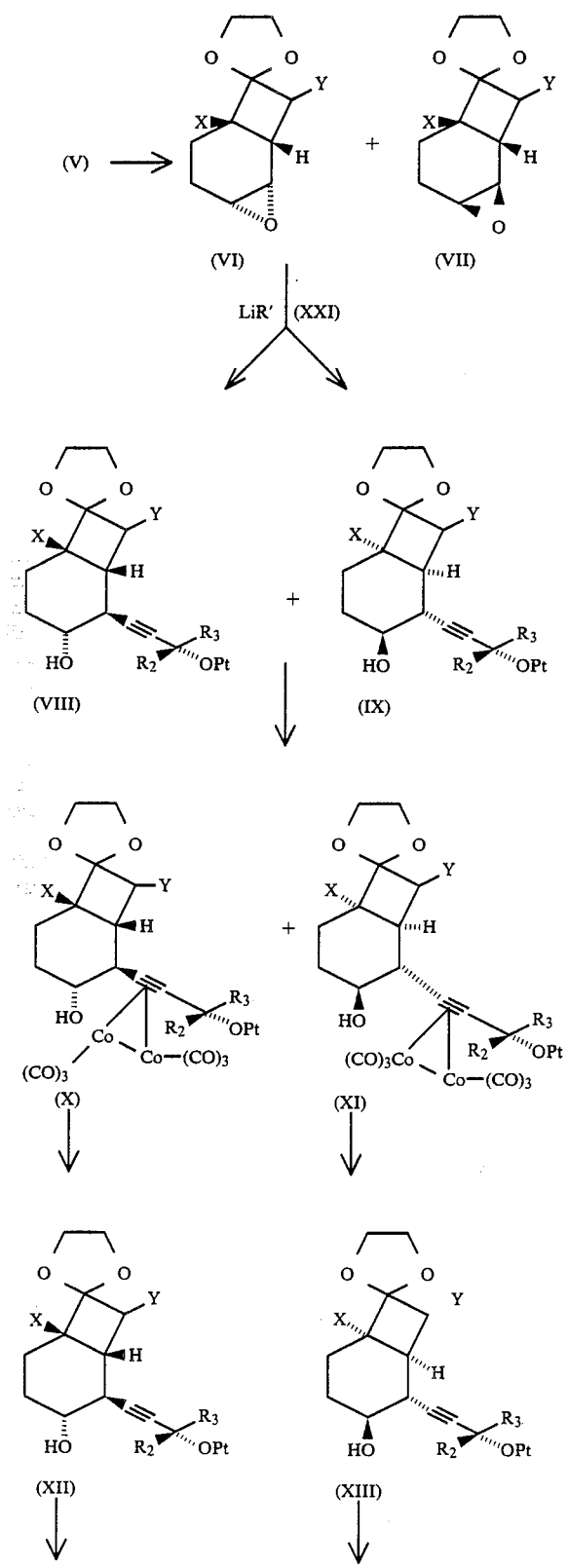

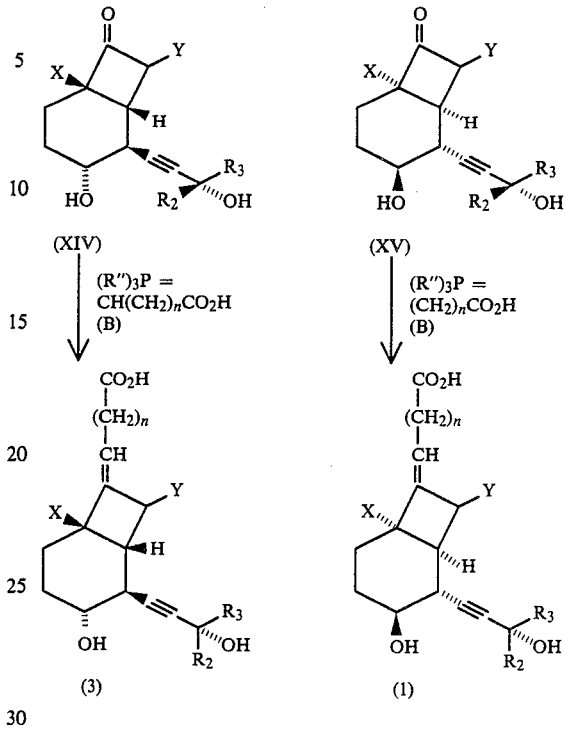

The synthesis of the compounds of formula (1), (2) and (3) where $R_1$ is —$CO_2H$ and A is —C≡C— begins with the reaction of cyclohexadiene and the chloroalkanoyl chloride of formula (IA) or (IB). For example, to prepare the compound of formula (II), cyclohexadiene is reacted with about 0.5 to 1.0 molar equivalents, preferably about 0.75 molar equivalents, of dichloroacetyl chloride, the compound of formula (IA), in an ethereal solvent, such as tetrahydrofuran, dioxan or preferably diethyl ether in the presence of about 0.5 to 1.0 molar equivalents, preferably about 0.75 molar equivalents, of triethylamine. The reaction is carried out at a temperature of about 20° C. up to the reflux temperature of the chosen solvent, preferably about 35° C., for about 1 to 6 hours, preferably about 3 hours. The reaction mixture is then stirred at a temperature of about 0°–30° C., preferably about 23° C., for about 8 to 48 hours, preferably about 20 hours. When the reaction is substantially complete, the product of formula (II) is isolated by conventional means.

The compound of formula (II) is then reacted with the appropriate alcohol of formula (IC). For example, to prepare the compound of formula (III) where X is methoxy and Y is H, the compound of formula (II) is reacted in the presence of 1 to 2 molar equivalents, preferably about 1.1 molar equivalents, of base such as sodium methoxide or a tertiary organic base such as N-methylpiperidine, pyridine or preferably triethylamine with methanol as a solvent. The reaction is carried out at a temperature of about 0°–40° C., preferably about 23° C., for about 1 to 5 hours, preferably about 1½ hours, giving the compound of formula (IIA). To the reaction mixture is then added about 1 to 4 molar equivalents, preferably about 3 molar equivalents, of a zinc-copper couple. The reaction is carried out at a temperature of about 0°–40° C., preferably about 23° C., for about 1 to 10 hours, preferably about 3 hours. When the reaction is substantially complete, the compound of formula (III) where Y is H, is isolated by conventional means.

Similarly, to prepare the compound of formula (III) where Y is lower alkyl, cyclohexadiene is reacted with the appropriate 2-chloroalkanoyl chloride of formula (IB) in the same manner as shown above for the preparation of the compound of formula (II). For example, to prepare the compound of formula (III) where Y is methyl, cyclohexadiene is reacted with 2-chloropropionyl chloride. The mixture of exo-methyl compound (IIB) and endo-methyl compound (IIC) thus produced is then separated into the individual isomers (IIB) and (IIC) by conventional means, preferably chromatography.

The compound of formula (IIB) or (IIC) is then reacted with the appropriate alcohol of formula (IC) in the same manner as shown above for the preparation of the compound of formula (IIA), giving the compound of formula (III) where Y is exo-(lower alkyl) or endo-(lower alkyl), which is isolated conventionally.

The subsequent preparative procedures will be described without specifying the sterochemistry of the 8-(lower alkyl) group, where present. However, it should be understood that the preparations described are applicable equally to the 8-exo-(lower alkyl) or the 8-endo-(lower alkyl) compounds, and that both isomers are intended to fall within the scope of these preparations.

The compound of formula (III) is then reacted with about 2 to 10 molar equivalents, preferably about 5 molar equivalents, of ethylene glycol in a solvent such as toluene, xylene or preferably benzene in the presence of an acid catalyst such as hydrochloric acid, methanesulfonic acid or preferably p-toluenesulfonic acid. The reaction is carried out at the reflux temperature of the solvent used removing water azeotropically, typically for about 1 to 10 hours, preferably about 4 hours. When the reaction is substantially complete, the product of formula (IV) is isolated and purified by conventional means.

The compound of formula (IV) is then reacted with about 1 to 2 molar equivalents, preferably about 1.2 molar equivalents, of a halogenating agent such as N-chlorosuccinimide or preferably N-bromoacetamide in an aqueous solvent mixture such as acetone-water. This is the preferred procedure for the compounds of formula (IV) where Y is lower alkyl. The reaction is initially carried out at about 0° C. for about 1 hour, then at a temperature of about 5°–40° C., preferably about 25° C., for about 8 to 40 hours, preferably about 20 hours. To this solution is added about 2 to 5 molar equivalents, preferably about 3 molar equivalents, of a base such as sodium hydroxide, sodium bicarbonate or preferably potassium carbonate, and the mixture stirred at a temperature of about 0°–40° C., preferably about 25° C., for about 12 hours to 3 days, preferably about 1 day. When the reaction is substantially complete, the mixture of compounds of formula (VI) and (VII) is isolated and purified by conventional means.

Alternatively, the compound of formula (IV) is reacted with about 1 to 2 molar equivalents, preferably about 1.1 molar equivalents, of an epoxidizing agent such as peracetic acid, perbenzoic acid or preferably m-chloroperbenzoic acid. This is the preferred procedure for the compounds of formula (IV) where Y is H. The reaction is carried out in an inert solvent such as chloroform, cyclohexane or preferably methylene chloride, at a temperature of about 0°–40° C., preferably about 25° C., for about 1 to 10 hours, preferably about 3 hours.

The bicyclic epoxyacetals (VI) and (VII) are then reacted as a mixture with a lithium acetylide of formula (XXI) in the presence of boron trifluoride etherate to give the diastereomeric alcohols of formula (VIII) and (IX). In the reaction of the lithium acetylenic reagent with the mixture of epoxyacetals (VI) and (VII), both α and β epoxides undergo reaction, and the attack by the lithium acetylide reagent is not regioselective. Thus, the reaction gives a mixture from which the desired mixture of diastereoisomers (VIII) and (IX) is separated by chromatography. To carry out this process, the epoxides are reacted with about 1 to 5 molar equivalents, preferably about 2.5 molar equivalents, of the lithium acetylide of formula (XXI) in the presence of about 0.1 to 1.0 molar equivalents, preferably about 0.6 molar equivalents, of boron trifluoride etherate. The reaction is carried out in an ethereal solvent, as defined above, preferably tetrahydrofuran, for about 10 minutes to 1 hour, preferably 30 minutes, at a temperature of about −50° C. to −100° C., preferably about −78° C. When the reaction is substantially complete, the mixture of diastereomeric alcohols (VIII) and (IX) is isolated and purified by conventional means. Preparation of the organolithium acetylides (XXI) is described following Reaction Scheme 4 below.

The two individual stereoisomers (VIII) and (IX) are separated from the mixture of diastereomeric alcohols as their dicobalthexacarbonyl complexes. The mixture of (VIII) and (IX) is treated with about 1 to 2 molar equivalents, preferably about 1.25 molar equivalents, of dicobalt octacarbonyl in an ethereal solvent as defined above, preferably diethyl ether. The reaction is carried out at a temperature of 0°–40° C., preferably about 25° C., for about 30 minutes to 4 hours, preferably about 1 hour. When the reaction is substantially complete, the mixture of products is isolated conventionally, and the two stereoisomers separated as their cobalt complexes (X) and (XI) by chromatography. The complexes of formula (X) and (XI) are then converted separately to the stereoisomers (XII) or (XIII) by reaction with about 1 to 2 molar equivalents, preferably about 1.2 molar equivalents, of ceric ammonium nitrate in an aqueous solvent, for example acetone-water. The reaction is carried out for about 2 minutes at a temperature of about 25° C. When the reaction is substantially complete, the products of formula (XII) and (XIII) are isolated and purified by conventional means.

The compounds (XII) and (XIII) are then hydrolyzed to the ketones of formula (XIV) and (XV), respectively. The compound is dissolved in an inert solvent miscible with water, for example methanol, acetone, or preferably acetonitrile, and stirred with about 1 to 10 molar equivalents, preferably about 5 molar equivalents, of an acid catalyst, such as hydrochloric acid, p-toluenesulfonic acid or preferably sulfuric acid, in water. The reaction is carried out at a temperature of about 0°–80° C., preferably about 50° C., for 2–48 hours, preferably about 16 hours. When the reaction is substantially complete, the product of formula (XIV) or (XV) is isolated and purified by conventional means.

The compounds of formula (XIV) and (XV) where X is hydroxy are prepared from the compounds of formula (XIV) and (XV) where X is methoxy. Typically, the compounds of formula (XIV) and (XV) where X is methoxy are reacted with about 10 to 100 molar equivalents, preferably about 20 molar equivalents, of 48% aqueous hydrobromic acid in a water-miscible solvent as defined above, preferably acetone. The mixture is stirred at a temperature of about 0°–50° C., preferably about 23° C., for about 10 to 72 hours, preferably about 24 hours. When the reaction is substantially complete, the product of formula (XIV) or (XV) where X is hydroxy is isolated by conventional means.

The compunds of formula (XIV) and (XV) are then reacted with a phosphorus ylide of formula (B), where R″ is aryl, prepared from the corresponding phosphonium salt. Alternatively, the compounds of formula (XIV) and (XV) are reacted with a phosphorus ylide prepared from a compound of the formula (R″O)$_2$OPCH$_2$(CH$_2$)$_n$CO$_2$H where R″ is alkyl or aryl, or (R″)$_2$OPCH$_2$(CH$_2$)$_n$CO$_2$H where R″ is aryl. Preferably, a triaryl phosphine, preferably triphenylphosphine, is reacted with the appropriate ω-halocarboxylic acid as described in J. Org. Chem., 27, 3404 (1962). The resulting phosphonium salt is slurried in an aprotic solvent such as diethyl ether, tetrahydurofuran or preferably dimethyl sulfoxide, at a temperature of about 0°–40° C., preferably about 25° C., and about 2.2 molar equivalents of a strong base added, such as butyl lithium, sodium amide, potassium hydride, sodium alkoxide or preferably dimsyl sodium in dimethyl sulfoxide. After about 20 minutes, 1 molar equivalent of the compound of formula (XIV) or (XV) is added and the mixture stirred at a temperature of about 20° C.-70° C., preferably about 50° C., for about 1-10 hours, preferably about 4 hours. When the reaction is substantially complete, the products are isolated conventionally. The reaction yields a mixture of (E) and (Z) isomers which are separated by chromatography. In this manner, the (E) and (Z) isomers of compounds of formula (1) and (3) where A is —C≡C— and R$_1$ is —CO$_2$H are obtained.

Similarly, by replacing the chiral organolithium acetylide (XXI) with one of opposite chirality (prepared from the acetylenic alcohol of formula (XXV) by protecting the hydroxy group and reacting with butyllithium as shown in Reaction Scheme 4), the (E) and (Z) isomers of the compound of formula (2) are prepared. If the product compounds of our invention are prepared from optically inactive starting materials and without employment of chiral reagents, the products will be obtained as (optically inactive) racemic mixtures.

The compounds of the present invention where n is 2 may also be prepared according to Reaction Scheme IA.

REACTION SCHEME IA

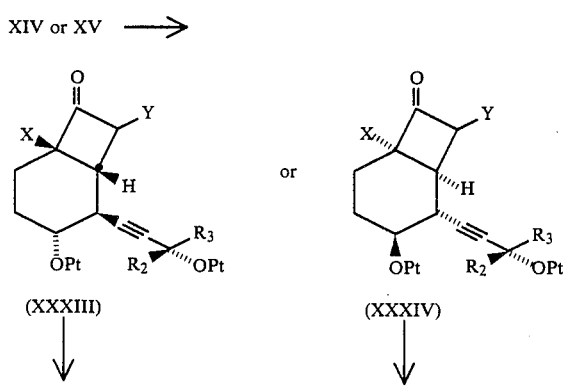

-continued
REACTION SCHEME IA

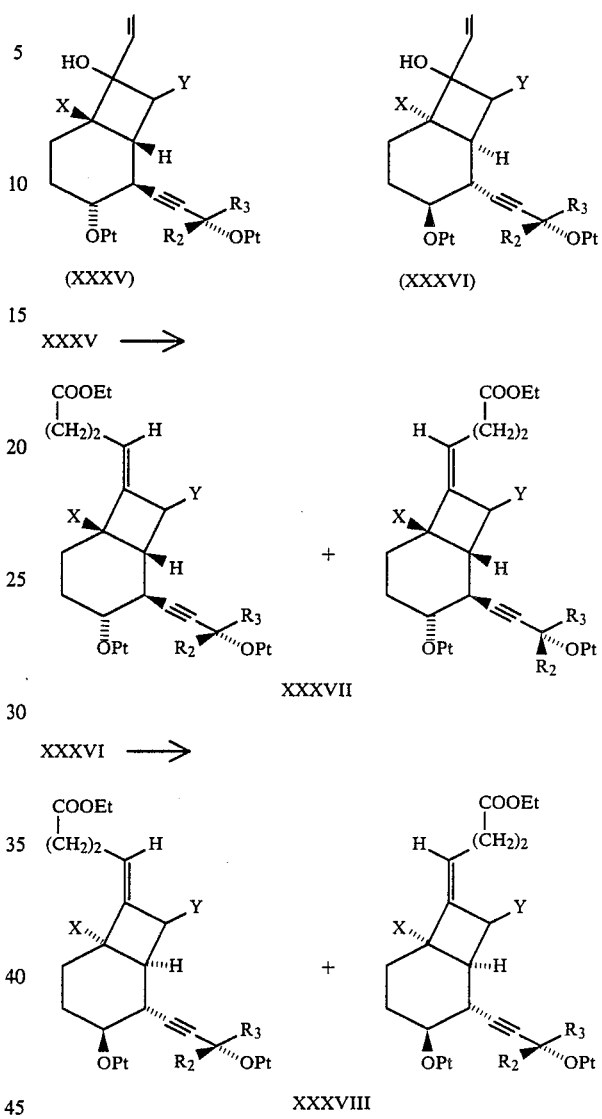

Compounds XIV and XV are converted into the 3 and 3′ protected compounds (XXXIII and XXXIV) by condensation with trialkylsilyl chloride and imidazole. Compounds (XXXIII) and (XXXIV) are then reacted with vinyl Grignard to give vinyl carbinols (XXXV and XXXVI). Claisen rearrangement of vinyl carbinols is carried out with ethyl orthoacetate in the presence of acid catalyst according to the methods described in J. Amer. Chem. Soc., 92, 741 (1970) to give compounds (XXXVII) and (XXXVIII) as E/Z mixtures. Separation of the E and Z isomers may be accomplished by chromatography. Saponification of the separated esters with lithium hydroxide in aqueous methanol gives the corresponding acids. Subsequently, the protecting groups at the 3- and 3′-positions may be removed by treatment with dilute aqueous acid preferably mineral acid such as sulfuric acid in acetonitrile or with hydrogen fluoride or tetrabutylammonium fluoride in tetrahydrofuran at 0°–40° C. as described in J. Amer. Chem. Soc., 94, 6190 (1972) to form the compounds of formula (1) or (3) or, where R$_1$ is —CO$_2$H and A is —C≡C—.

Similarly, by starting with the opposite enantiomer of the compound of formula XIV, prepared as shown above, the compound of formula (2) where $R_1$ is —$CO_2H$ and A is —C≡C— is prepared.

The preferred mode for the synthesis of the compounds of formula (1), (2) and (3) where A is —C≡C— and $R_1$ is —$CO_2H$ is illustrated in Reaction Scheme IB.

REACTION SCHEME IB

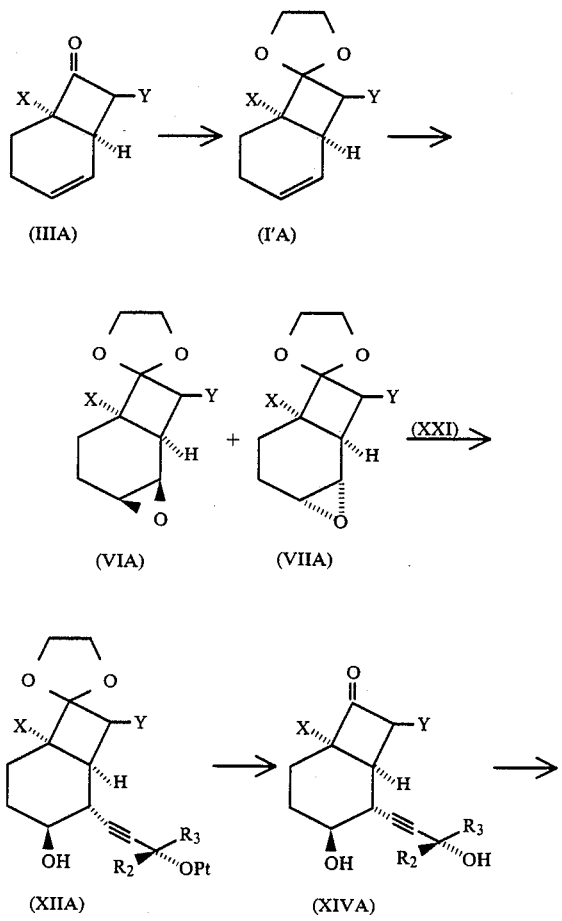

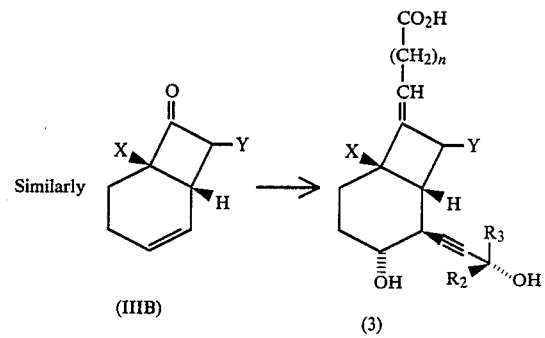

-continued
REACTION SCHEME IB

The reaction scheme starts with the optically pure bicyclo[4.2.0]oct-2-en-7-ones of formula (IIIA) or (IIIB).

The subsequent reactions are carried out in the same manner as shown in Reaction Scheme 1. However, comparison of Reaction Scheme 1 and Reaction Scheme 1B demonstrates the advantage of the latter scheme, as the formation of the mixture of diastereomers (VIII) and (IX) in Reaction Scheme 1 is avoided. Thus the steps of formation of a cobalt complex followed by chromatography and conversion back to the individual diastereomers (XII) and (XIII) are avoided.

The above Scheme 1B illustrates the preparation of the compounds of formula (1) and (3). To prepare the compounds of formula (2), the same sequence is carried out starting with the compound of formula (IIIA), using a lithium acetylide of formula (XXI) of opposite chirality (i.e. prepared from an (R)-acetylenic alcohol), the preparation of which is shown above.

The enantiomeric bicyclo[4.2.0]oct-2-en-7-ones of formula (IIIA) and (IIIB) where Y is H, used as starting materials in Reaction Scheme 1B, are prepared as shown (as the compounds of formulas (XLV) and (XLVI)) in Reaction Scheme 1C.

REACTION SCHEME 1C

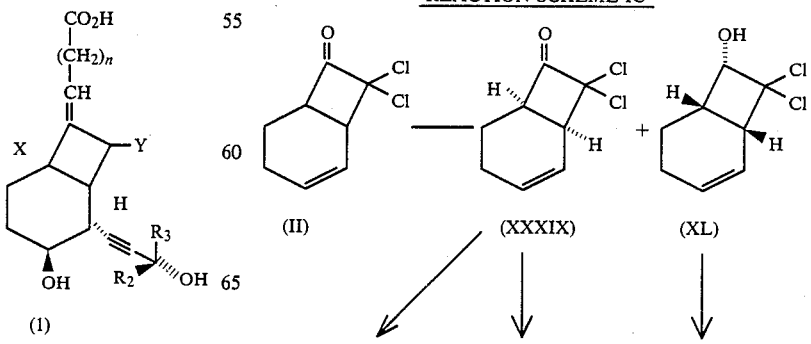

-continued
REACTION SCHEME IC

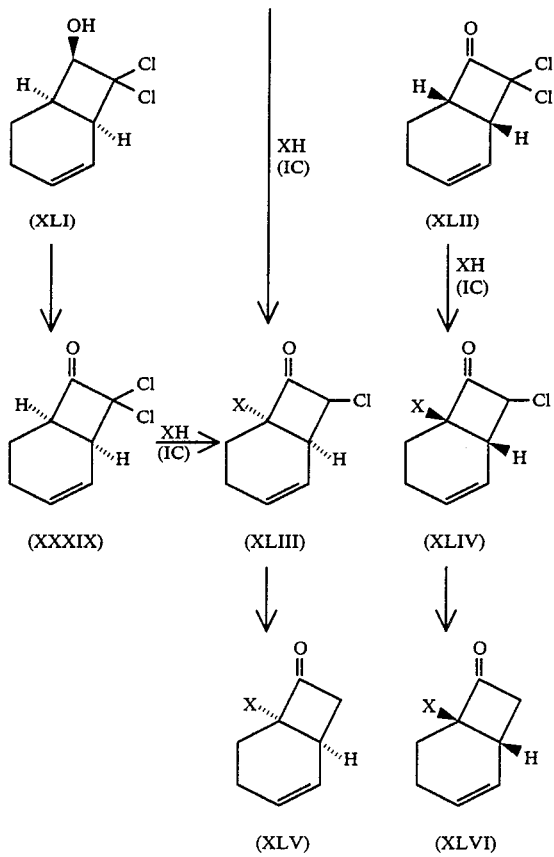

In the first step, the racemic 8,8-dihalobicyclo[4.2.-0]oct-2-n-7-one (II), preferably 8,8-dichloro-, is treated with a micro-organism, preferably Baker's Yeast, optionally in the presence of a yeast nutrient and a sugar such as sucrose or dextrose. For every gram of ketone about 2–25 g, preferably about 8–15 g, of Baker's Yeast is used, plus about 0 g to 1.0 g, preferably about 0.7 g, of yeast nutrient, and about 0 g to 2.0 g, preferably about 0.5 g, of sucrose. The reaction is carried out in a solvent of about 2% to 10% ethanol, preferably about 5% ethanol, in water at a temperature of about 20°–40° C., preferably about 33° C., for about 15 minutes to 2 hours, preferably about 45 minutes. The ketone (XXXIX) and the alcohol (XL) are isolated, separated and purified by conventional means, preferably by column chromatography.

The ketone of formula (XXXIX) may optionally be reduced to the alcohol of formula (XLI) with a mild reducing agent recrystallized from a suitable solvent and oxidized back to the compound of formula (XXXIX). This process acts as a purification procedure for the compound of formula (XXXIX), and results in a compound of 100% enantiomeric purity. For example, the ketone of formula (XXXIX) is reacted with about 1 to 10 molar equivalents, preferably about 2 to 4 molar equivalents, of sodium borohydride in a protic solvent such as water, ethanol or preferably methanol at a temperature of about 0°–25° C., preferably about 5° C., for about 15 minutes to 4 hours, preferably about 1 hour, giving the compound of formula (XLI), which is isolated and purified by conventional means.

The alcohols of formula (XL) or (XLI) are then converted to the ketones of formula (XLII) or (XXXIX), respectively, using an oxidizing agent such as an aqueous solution of chromic acid and sulfuric acid (Jones reagent), sodium dichromate or an organochromium reagent, preferably pyridinium chlorochromate. Typically, the ketone is reacted with about 1.5 to 4 molar equivalents, preferably about 2 molar equivalents, of pyridinium chlorochromate in the presence of about 4 to 10 molar equivalents, preferably about 6 molar equivalents, of magnesium sulfate in an inert solvent such as chloroform or preferably methylene chloride. The reaction is carried out at a temperature of about 30°–70° C., preferably about 40° C., for about 2 to 10 hours, preferably about 4 hours. When the reaction is substantially complete, the product is isolated and purified by conventional means, to give the compound of formula (XLII) or (XXXIX).

The optically pure ketones of formula (XXXIX) and (XLII) are then reacted with the appropriate alcohol of formula (IC) as described above. For example, reaction with methanol gives the mono-chloro ketones of formula (XLIII) and (XLIV) where X is methoxy. The compounds of formula (XLIII) and (XLIV) are then reacted with a dechlorinating agent such as tri-n-butyltin hydride, a zinc-copper couple or preferably zinc in acetic acid as described in detail above to give the enantiomers of formula (XLV) and (XVVI).

The enantiomeric bicyclo[4.2.0]oct-2-en-7-ones where Y is exo- or endo-(lower alkyl) used as starting materials in Reaction Scheme 1B. are prepared as shown (as the compounds of formula (L), (LI), (LII) and (LIII) in Reaction Scheme 1D.

REACTION SCHEME 1D

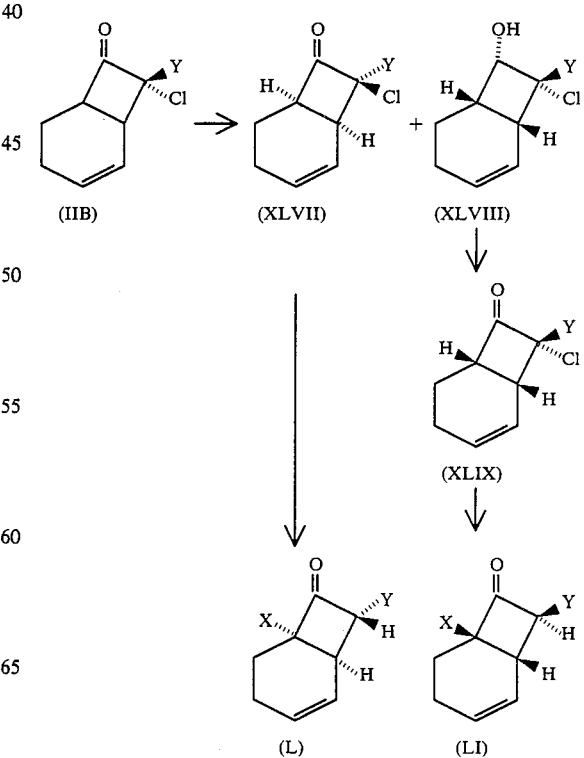

-continued
REACTION SCHEME 1D

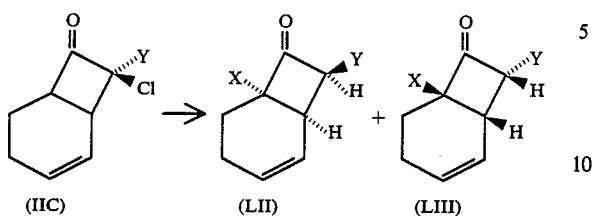

The compound of formula (IIB) is reacted with Baker's Yeast as shown above to give the compounds of formula (XLVII) and (XLVIII) where Y is exo-(lower alkyl), which are separated. The compoumd of formula (XLVIII) is oxidized to the compound of formula (XLIX), and then both (XLVII) and (XLIX) are then reacted with an alcohol of formula (IC) as described above to give the enantiomers of formula (L) and (LI).

Similarly, the compound of formula (IIC) is converted to the enantiomers of formula (LII) and (LIII), where Y is endo-(lower alkyl).

(b) Where A is trans —CH=CH— and $R_1$ is —$CO_2H$

The synthesis of the compounds of formulas (1), (2) and (3), where A is trans —CH=CH— and $R_1$ is —$CO_2H$, is illustrated in Reaction Scheme 2.

REACTION SCHEME 2

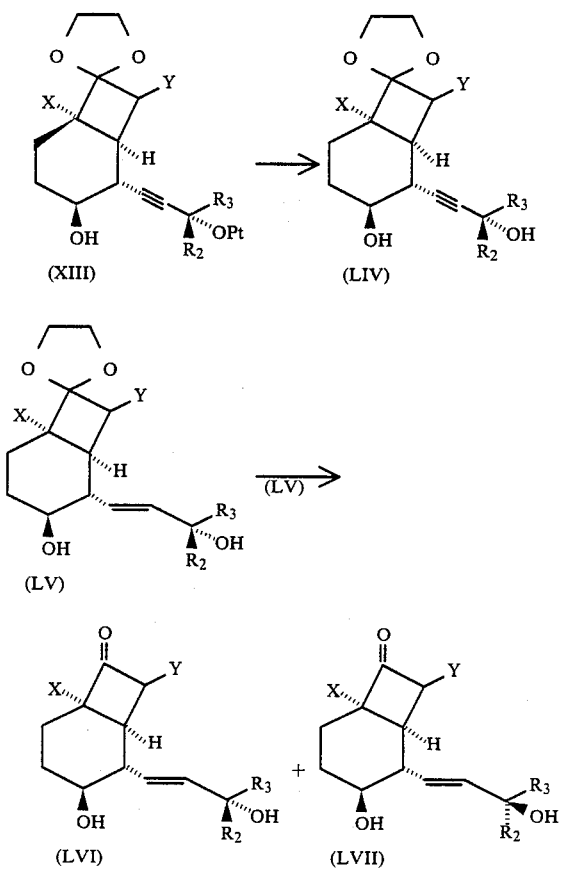

-continued
REACTION SCHEME 2

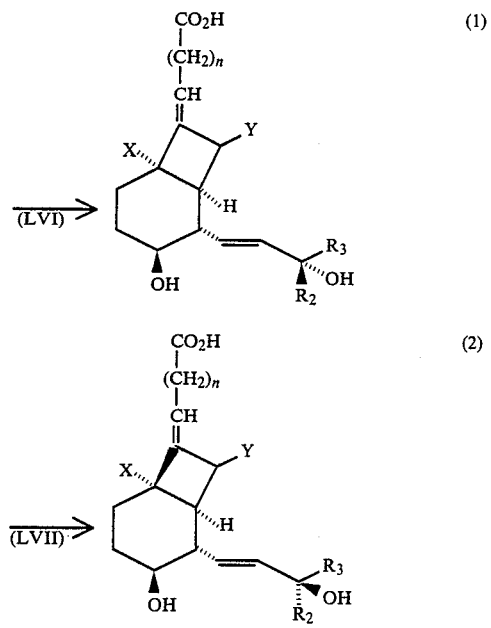

The synthesis begins with the removal of the preferred silyl protecting group from the compound of formula (XIII), prepared as shown in Section (a) above. Typically, the compound of formula (XIII) is dissolved in an ethereal solvent as defined above, preferably tetrahydrofuran, and about 1 to 10 molar equivalents, preferably about 2.5 molar equivalents, of tetrabutylammonium fluoride in tetrahydrofuran is added. The mixture is stirred for about 1 to 20 hours, preferably about 5 hours, at about 0°–50° C., preferably about 23° C. When the reaction is substantially complete, the compound of formula (LIV) is isolated and purified by conventional means.

The compound of formula (LIV) is then reduced with lithium aluminum hydride to a trans olefin of formula (LV). The compound of formula (LIV) is dissolved in an ethereal solvent as defined above, preferably tetrahydrofuran, and added to a solution of about 5 to 20 molar equivalents, preferably about 9 molar equivalents, of lithium aluminum hydride in tetrahydrofuran under nitrogen. The reaction is conducted at about reflux temperature for about 1 to 10 hours, preferably about 3 hours. When the reaction is substantially complete, the trans olefin of formula (LV) is isolated and purified by conventional means.

The compound of formula (LV) is then treated with an inorganic acid, preferably sulfuric acid, to hydrolyze the ketal group. The reaction is carried out in a mixture of a water-miscible solvent as defined above, preferably acetonitrile, and dilute sulfuric acid, preferably about 1.2M, in an approximately 2:1 ratio. The mixture is stirred at about 30°–100° C., preferably about 65° C., for about 1 to 5 hours, preferably about 2 hours. This treatment simultaneously hydrolyzes the ketal group and partially epimerizes the 3′-hydroxy group on the vinylic side chain to give two diastereomeric ketones of formula (LVI) and (LVII). When the reaction is substantially complete, the products are isolated and separated by conventional means.

The ketones of formula (LVI) and (LVII) are then converted into the corresponding alkylidenes of formula (1) and (2) where $R_1$ is $CO_2H$ and A is trans $HC=CH$ by reaction with a Wittig reagent or other phosphorus ylides as described in detail in section (a) above, and similarly separated. Alternatively, the ketones of formula (LVI) and (LVII) are protected and converted to vinyl alcohols and a Claisen rearrangements carried out as described in section (a) above and illustrated in Reaction Scheme 1A.

Similarly, starting with the compound of formula (XII) and following the procedures detailed above, the compound of formula (3) where $R_1$ is $—CO_2H$ and A is trans $HC=CH$ is made.

Alternatively, a method of arriving at a mixture of the intermediate compound of formula (LVI) and its diastereomer (LVIA) is illustrated in Reaction Scheme 2A below.

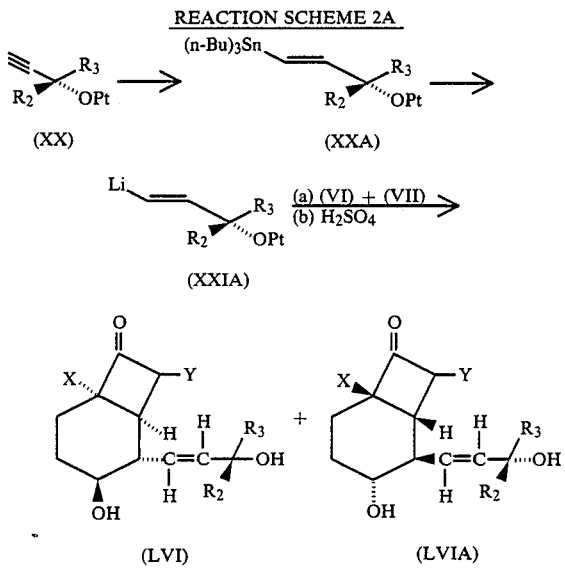

The compound of formula (XX), prepared as illustrated in Reaction Scheme 4 below, is reacted with about 3 to 10 molar equivalents, preferably about 5 molar equivalents, of tri-n-butyltin hydride, at a temperature of about 85° C. for about 1 hour in the presence of a catalytic quantity of azobisisobutyronitrile. The temperature is then raised to about 125° C. for about 1 hour, then excess tri-n-butyltin hydride removed by careful distillation. The compound of formula (XXA) that remains is then dissolved in an ethereal solvent, preferably tetrahydrofuran, and reacted with about 1 molar equivalent of n-butyl lithium in an inert atmosphere at about −78° C. The temperature is allowed to rise to about −40° C., and the reaction mixture stirred for about 1 hour. The reaction mixture is then cooled to about −78° C. and reacted with the mixture of epoxides (VI) and (VII) as described above in 1(a) above. The resulting mixture is then hydrolized with acid, also as shown in 1(a) above, giving a mixture of the compound of formula (LVI) and its diastereomer (LVIA), which, when reacted with an appropriate phosphorus ylide, as detailed above in section (a), followed by chromatography, as shown above, gives a racemic mixture of the compounds of formula (1) and (3), where $R_1$ is $—CO_2H$ and A is trans $—CH=CH—$, as the individual (E) and (Z) isomers.

Similarly, by replacing the propargylic alcohol of formula (XX) with one of opposte chirality (prepared as described in 1(a) above), a mixture of the compound of formula (LVII) and its diastereomer is prepared.

The structures depicted herein, including the novel compounds of our invention, have multiple chiral centers and are optically active. While, for illustrative purposes, only one optical isomer is depicted, our invention encompasses all optical isomers and mixtures thereof, said mixtures including racemates and diastereomeric mixtures in all proportions. If the product compounds of our invention are prepared from optically inactive starting materials and without employment of chiral reagents, the products will be obtained as (optically inactive) racemic mixtures.

(c) When A is $—CH=CHCH_2—$, $R_2$ is optionally $—CH=CH_2$ and $R_1$ is $—CO_2H$.

The compounds of formulas (1), (2) and (3) where A is $—CH=CHCH_2—$, $R_2$ is optionally $—CH=CH_2$ and $R_1$ is $—CO_2H$ are prepared in the same manner as shown in Reaction Scheme 2A above. The starting acetylenic alcohols necessary to carry out this synthesis are prepared as shown in Reaction Scheme 2B.

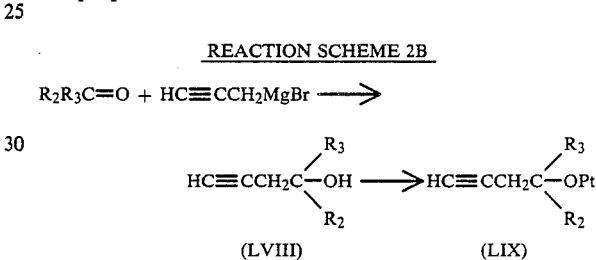

For example, when $R_2$ is H and $R_3$ is cyclohexyl, cyclohexanecarboxaldehyde is reacted with propargylmagnesium bromide to give an acetylenic alcohol of formula (LVIII), which is protected as shown above to give a compound of formula (LIX), where Pt is preferably t-butyldimethylsilyl. In the case where $R_2$ is $—CH=CH_2$, the protection of the alcohol group is carried out by reacting with t-butyldimethylsilyl triflate. The reactions are discussed in more detail in J. Med. Chem., Vol. 25, pp. 492–494 (1982), which is incorporated herein by reference.

The compound of formula (LIX) is then converted to the compounds of formula (1), (2) and (3), where A is $—CH=CHCH_2—$ and $R_1$ is $—CO_2H$, as shown in Reaction Scheme 2A and Reaction Scheme 1.

(d) When A is $—CH_2CH_2—$ and $R_1$ is $—CO_2H$

The compounds of formulas (1), (2) and (3) where A is $—CH_2CH_2—$ and $R_1$ is $—CO_2H$ are made as illustrated in Reaction Scheme 3.

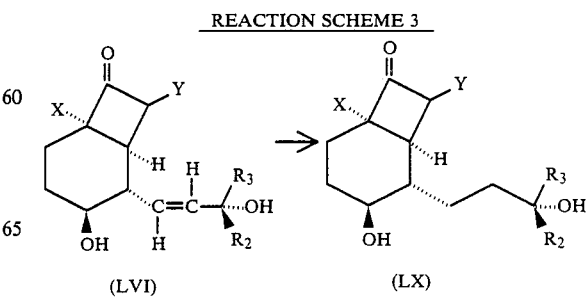

-continued
REACTION SCHEME 3

(LVII) →
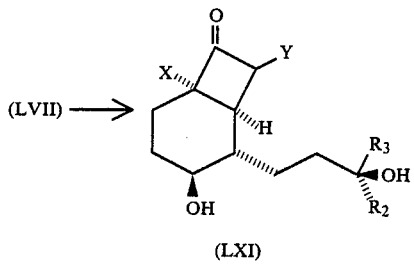
(LXI)

The preparation of the compounds of formulas (LVI) and (LVII) is shown in section (b) above. To prepare the compound of formula (LX) or (LXI) the compound of Formula (LVI) or (LVII) is dissolved in an inert solvent as defined above, or methanol or preferably ethanol and reacted with hydrogen at a pressure of about 1–5 atmospheres, preferably about 1 atmosphere, in the presence of a homogenous catalyst such as chlorotris(triphenylphosphine)rhodium (Wilkinson catalyst) or a heterogeneous catalyst such as copper chromite, platinum on carbon or preferably palladium on carbon. The reaction is conducted at a temperature of about 0°–50° C., preferably about 25° C., until about 1 molar equivalent of hydrogen is absorbed, typically in about 2 hours. When the reaction is substantially complete, the product of Formula (LX) or (LXI) is isolated by conventional means.

The ketone of formula (LX) or (LXI) is then converted into the corresponding alkylidenes of formula (1) or (2) where $R_1$ is $-CO_2H$ and A is $CH_2CH_2$ by reaction with a Wittig reagent or other phosphorus ylides, as described in detail above in section (a). Alternatively, the ketones of formula (LX) and (LXI) are converted to vinyl alcohols and a Claisen rearrangement carried out as described in section (a) above and illustrated in Reaction Scheme 1A. The alkylidenes are separated into their (E) and (Z) isomers also as shown in section (a) above.

Similarly, starting with the compounds of opposite chirality to (LVI) and (LVII), obtained from the compound of formula (XII) by reaction with lithium aluminum hydride followed by hydrolyzing the product as shown in section (b) above, the compound of formula (3) where $R_1$ is $-CO_2H$ and A is $CH_2CH_2$ is obtained. It is similarly separated into its (E) and (Z) isomers.

It is obvious that an alternative method of arriving at the ketones of formula (LX) or (LXI) or their enantiomers is to reduce the corresponding acetylenic compounds, prepared as shown in 1(a) above, by catalytic reduction as shown above, carrying out the reaction until 2 molar equivalents of hydrogen are absorbed. For example, the compounds of formula and (XIII) or (XV) could be used to arrive at the ketone of formula (LX). The same subsequent procedures are then followed as shown in section (a) above to arrive at the compounds of formulas (1), (2) and (3) where A is $-CH_2CH_2-$ and $R_1$ is $-CH_2H$.

Alternatively, a method of arriving at the compounds of formula (1), (2) and (3) where A is $-CH_2CH_2-$ is to react the mixture of epoxides, the compounds of formula (VI) and (VII), with the corresponding saturated side chain as an organometallic reagent

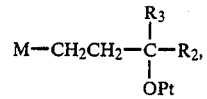

which can be prepared by standard methods from the appropriate halide by reaction with a metal, for example Mg or Li, or by exchange with a more reactive organometallic reagent, for example an aryl lithium derivative.

The optically active acetylenes used in Scheme I(a) in which $R_2$ is hydrogen are prepared according to Reaction Scheme 4.

REACTION SCHEME 4

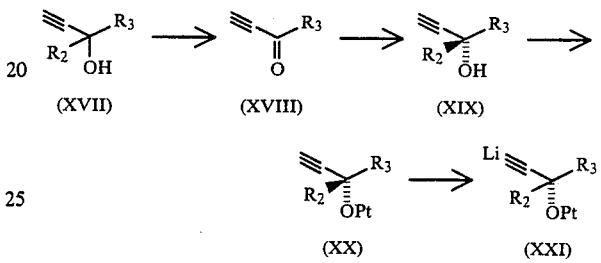

As shown in Reaction Scheme 4, a propargylic alcohol of formula (XVII), wherein $R_2$ is H, is oxidized with Jones reagent to give a propargylic ketone of formula (XVIII). This ketone is reduced with isopinocamphenyl-9-borabicyclo[3.3.1]nonane according to the method described in J. Amer. Chem. Soc., 101, 2352 (1979) to give the chiral propargylic alcohols (XIX). The propargylic alcohols (XIX) are converted into O-protected derivatives (XX) by condensation with, for example, trialkylsilyl chlorides and imidazole. Compounds (XX) are reacted with butyllithium to give lithioacetylides (XXI), which are used in Scheme I to convert epoxide (VI) into (VIII) and (IX). Propargylic alcohols of formula (XVII) wherein $R_2$ is methyl are prepared according to the general method of *Organic Synthesis*, Collective Volume 3, page 320 (1955).

Propargylic alcohols of formula

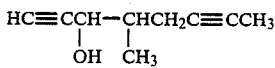

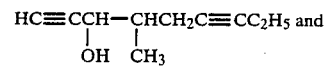

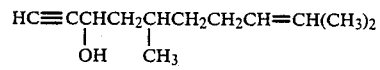

are prepared as illustrated in Reaction Scheme 4A.

REACTION SCHEME 4A

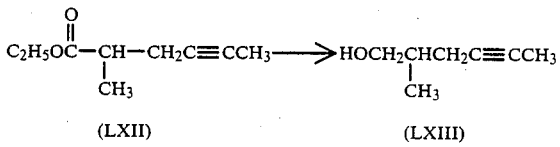

-continued
REACTION SCHEME 4A

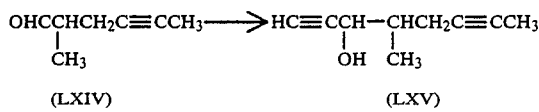

(LXIV)                (LXV)

The starting ester of formula (LXII), prepared as described in *Angew Chem. Int. Ed.* 20 1046 (1981), is first reduced with lithium aluminum hydride to give the alcohol of formula (LXIII). The alcohol is oxidized with, for example, pyridinium chlorochromate, to give the aldehyde of formula (LXIV), which is reacted with HC≡CMgBr or a lithium acetylide to give the desired propargylic alcohol of formula (LXV). The propargylic alcohol is then protected and reacted with butyl lithium as described above to give the compound of formula (XXI).

In the same manner as described above, the propargylic alchols of formula

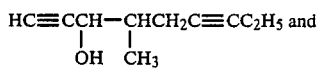

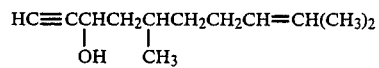

are prepared, starting from the appropriate ester. Alternatively, the alcohol corresponding to formula (H) necessary for the preparation of the latter compound is commercially available as Citronellol.

The optically active acetylenes used in Reaction Scheme I wherein $R_2$ is H or $CH_3$ may also be prepared according to Reaction Scheme 5. Reaction Scheme 5 is the method of Fried (*Ann. N.Y. Acad. Sci.*, 180, 39 (1971)). In this method a hemiphthalate of racemic (XVII), which is formed by condensation of (XVII) with phthalic anhydride, is converted into a mixture of diastereoisomeric salts (XXII) and (XXIII) using a suitable optically active amine. The mixture of salts is recrystallized from an appropriate solvent, typically acetonitrile, to give a pure diastereoisomeric salt (XXII). This salt is treated with dilute aqueous hydrochloric acid to give a hemiphthalate, which is hydrolyzed with aqueous base to give chiral acetylenic alcohol (XXIV). Similarly, a pure diastereomeric salt (XXIII) is obtained which is in the same manner converted to the acetylenic alcohol of opposite chirality, (XXV).

REACTION SCHEME 5

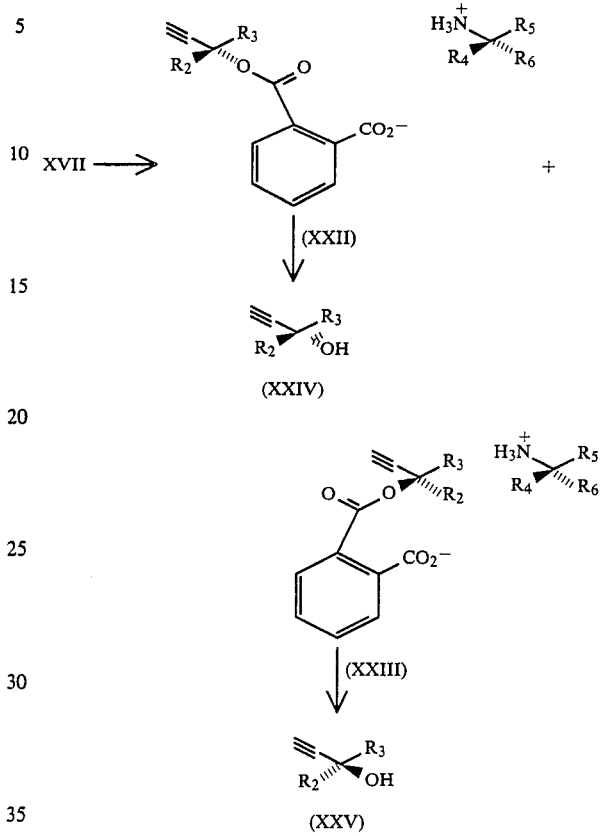

The racemic acetylenic alcohols used as starting materials in Reaction Schemes 4 and 5 are prepared by methods well known to those skilled in the art. For example, by reaction of a metal acetylide with an aldehyde or ketone. The reaction is discussed in more detail in *Chemistry of Acetylenes*, by Viehe, pp. 207–241, which is incorporated herein by reference.

The preceding discussion of Reaction Schemes 1–5 in part describe a method of synthesizing and separating the chiral intermediates of formula XII and XIII obtained from the reaction of the mixture of epoxides VI and VII with a chiral lithium acetylide of formula XXI. An alternative method of preparing these chiral intermediate of Scheme I starting with a racemic compound of formula XXI is illustrated in Reaction Scheme 6.

REACTION SCHEME 6

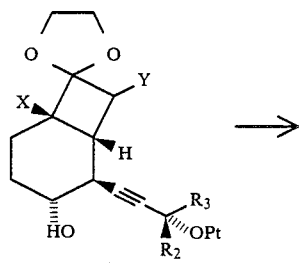

(d,l XII) = (XII + XIIA)

-continued
REACTION SCHEME 6

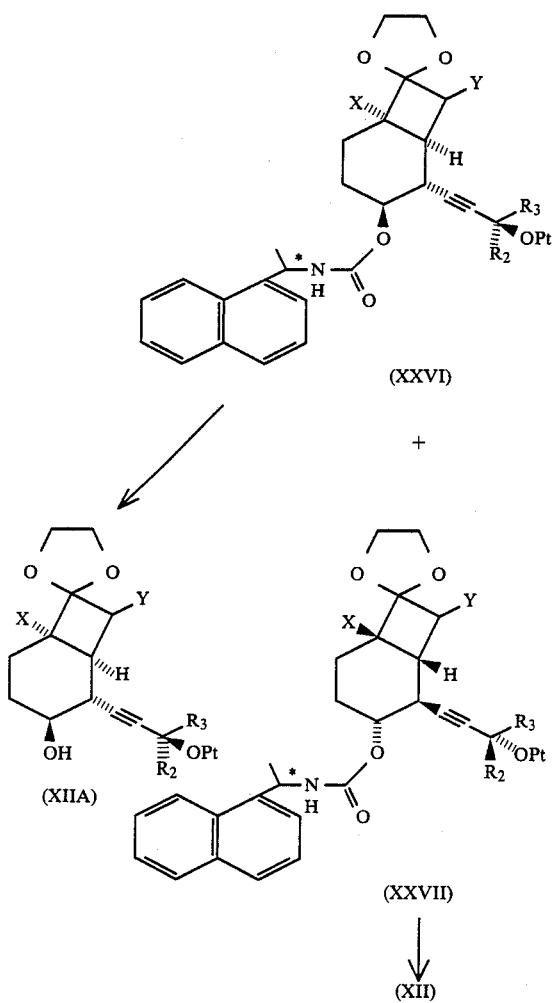

The starting point of Reaction Scheme 6 is a racemic mixture indicated as (d,l XII), which is a mixture of the isomers shown as formulas (XII) and (XIIA). The mixture (d,l XII) is obtained by reacting the mixture of epoxides (VI) and (VII) with a racemic lithium acetylide of formula (XXI). The reaction also gives the corresponding racemic mixture (d,l XIII), consisting of the compound of formula (XIII) and its enantiomer. The two diastereoisomers (d,l XII) and (d,l XIII) are separated by the cobalt procedure, as shown in Scheme I above. Condensation of (d,l XII) with (R)-(—)-α-(1-naphthyl)ethylisocyanate gives a mixture of diastereoisomers (XXVI) and (XXVII). These are separated by chromatography to give the individual diastereoisomers (XXVI) and (XXVII). Compounds (XXVI) and (XXVII) are reacted individually with lithium aluminum hydride to give enantiomers (XIIA) and (XII) respectively.

Similarly, following the above procedure the compound of formula (XIII) is separated from its enantiomer.

This scheme is discussed in more detail in U.S. patent application Ser. No. 716,872, now U.S. Pat. No. 4,608,388 which is incorporated herein by reference.

The pharmaceutically acceptable nontoxic salt derivatives of the compounds of formula (1), (2) and (3) are prepared by treating the free acids with an appropriate amount of pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganous hydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoethanol, lysine, arginine, histidine, procaine, choline, betaine, ethylenediamine, glucosamine, methylglucamine, theobromine, purines, piperazine, piperidine, N-ethylpiperidine, polyamine resins and the like. For preparing, for example, monovalent cation salts, the free acid starting material of formula (1), (2) and (3) is treated with one molar equivalent of pharmaceutically acceptable base in an appropriate solvent such as water, methanol, ethanol, isopropanol, butanol, acetone, dioxane or tetrahydrofuran. The molar ratio of compounds of formula (1), (2) or (3) to base used is chosen to provide the ratio desired for any particular salt. For preparing, for example, divalent cation salts such as the calcium or magnesium salts the free acid starting material of formula (1), (2) or (3) is treated with at least one-half molar equivalent of pharmaceutically acceptable base to yield a neutral salt. Similarly, for the trivalent cation aluminum salts, at least one-third molar equivalent of the aluminum base is employed if a neutral salt product is desired.

The novel free carboxylic acids (1), (2) and (3) of our invention can be reliberated from their respective salts by treating said salts with at least stoichiometric quantities of a strong acid, preferably an inorganic acid, e.g., hydrochloric acid, sulfuric acid, and the like, at temperatures ranging from about 0° C. to about 50° C., preferably at room temperature.

The pharmaceutically acceptable nontoxic esters of the novel acids (1), (2) and (3) of our invention can be prepared, e.g. by esterifying the corresponding free acids with a solution of the appropriate diazoalkane in a suitable inert solvent such as diethyl ether. An alternative and general method for producing the esterified acids of our invention comprises reaction of a benzene solution of the carboxylic acid with an alkyl halide in the presence of the organic base diazabicycloundecane (DBU) at temperatures from about 20° C.-80° C., and for about 1-12 hours. These conditions are particularly useful for esterifying acids containing labile functionality in the molecule, such as the prostaglandins and their synthetic analogues, since they avoid the use of acid catalysts and in fact involve no harsh reagents. (N. Ono et al, *Bull. Chem. Soc. Japan*, 51, 2401–2404 (1978)).

The esters can also be prepared under mild conditions by reacting the novel acids (1), (2) or (3) with an alcohol or phenol in the presence of a dehydrating agent, for example, dicyclohexylcarbodiimide. The procedure involves reacting equivalent amounts of the acid and alcohol or phenol in a suitable solvent, for example, methylene chloride and dimethylformamide mixture in the presence of a catalytic amount of 4-dimethylaminopyridine and an equimolar amount of dicyclohexylcarbodiimide. The reaction is carried out at a temperature of about —10° C. to 25° C., preferably about 0° C., for 8 to 48 hours, preferably about 16 hours.

Typical esters are those esters derived from methyl alcohol, ethyl alcohol, propyl alcohol, isopropyl alcohol, butyl alcohol, 2-butyl alcohol, 2-pentyl alcohol, isopentyl alcohol, 2-hexyl alcohol, and the like.

Alternatively, the alkyl esters can be prepared by transesterification, catalyzed by the corresponding alkoxide according to methods known in the art. It is preferred in preparing the esters via transesterification to go from a lower ester to a higher ester, e.g., from the methyl ester to the isoamyl ester. However, by using a substantial excess of a lower alcohol, a higher ester can be transesterified to a lower ester; thus, for example, by using a substantial excess of ethanol, the hexyl ester is converted by transesterification to the ethyl ester.

Salts of the compounds of formula (1), (2) and (3) may be interchanged by taking advantage of differential solubilities of the salts volatilities or activities of the acids, or by treating with the appropriately loaded ion exchange resin. For example, the interchange is effected by the reaction of a salt of the compounds of formula (1), (2) or (3) with a slight stoichiometric excess of an acid of a lower pKa than the acid component of the starting salt. This conversion is carried out at a temperature between about 0° C. and the boiling point of the solvent being used as the medium for the procedure.

II. Compounds Wherein $R_1$ is —CH$_2$OH or —CHO.

Compounds of formulas (1), (2) or (3) wherein $R_1$ is —CH$_2$OH or —CHO are prepared from the corresponding compounds (1), (2) or (3) wherein $R_1$ is —CO$_2$H, according to Reaction Scheme 7. Scheme 7 demonstrates a method for the conversion of (1) wherein $R_1$ is —CO$_2$H into (1) wherein $R_1$ is —CH$_2$OH or —CHO. By appropriate substitution of (1) wherein $R_1$ is —CO$_2$H the reactions of Scheme 7 may be used to prepare (2) or (3) wherein $R_1$ is —CH$_2$OH or —CHO.

REACTION SCHEME 7

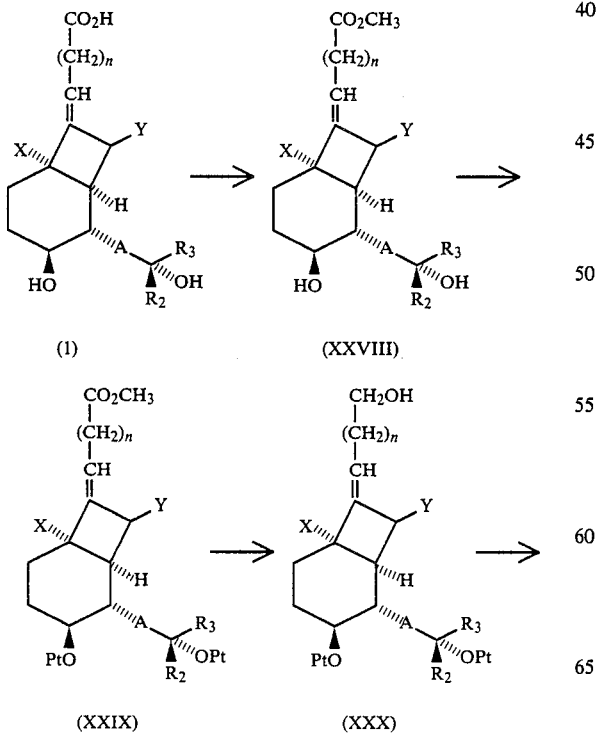

-continued
REACTION SCHEME 7

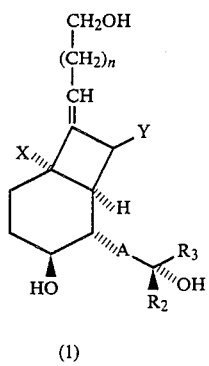

(1)

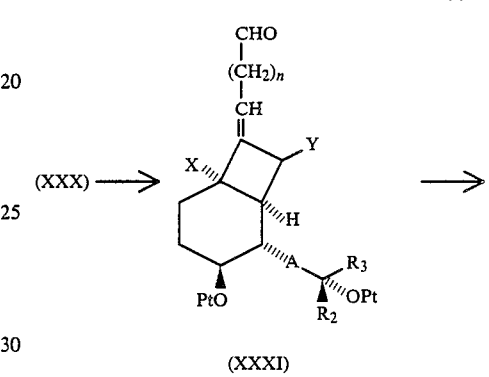

(XXXI)

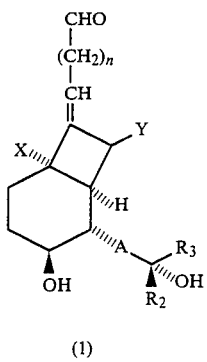

(1)

For example, reaction of (1) wherein $R_1$ is —CO$_2$H with diazomethane gives the methyl ester (XXVIII). Reaction of (XXVIII) with excess tert-butyldimethylchlorosilane in the presence of triethylamine and 4-dimethylaminopyridine gives the bis-protected derivative (XXIX) (Pt=Si(CH$_3$)$_2$t-Bu). Reduction of (XXIX) with lithium aluminum hydride gives carbinol (XXX), which is converted to (1) wherein $R_1$ it CH$_2$OH by reaction with tetrabutylammmonium fluoride in tetrahydrofuran. Oxidation of (XXX) with, for example, pyridinium chlorochromate give aldehyde (XXXI), which is converted into (1) wherein $R_1$ is CHO by reaction with tetrabutylammonium fluoride in tetrahydrofuran. Similarly, the compounds of formula (2) and (3) where $R_1$ is —CH$_2$OH or —CHO are prepared.

The compounds wherein $R_1$ is —CH$_2$OH may also be prepared as E/Z mixtures by reacting compounds XIV or XV with a stabilized anion or ylid of the formula P'—$\overline{\text{CH}}$—(CH$_2$)$_n$CH$_2\overline{\text{O}}$ (wherein P' is a residue normally associated with olefination reactions and n is 2 or 3), derived from, for example, 4-hydroxybutyltriphenylphosphonium bromide, in an aprotic solvent, preferably dimethylsulfoxide or dimethylsulfoxide/tetrahydrofuran mixture at a temperature range from 10° C. to 60° C. for 1-24 hours. Alternatively, the compounds in which $R_1$ is —CH$_2$OH may also be prepared by first reacting compounds XIV or XV with a compound of the formula P'—$\overline{\text{CH}}$—(CH$_2$)$_n$CH$_2$OPt (P' and n are as defined above, Pt is a protecting group for the hydroxyl function), for example, the ylide derived from 4-(t-butyldimethylsilyloxy)butyltriphenylphosphonium bromide, to form the E/Z mixtures (1) (2) or (3) wherein $R_1$ is —CH$_2$OPt. The protecting group may be removed according to the procedure as described in *J. Amer. Chem. Soc.*, 94, 6190 (1972) by treatment with dilute aqueous acid, such as mineral acid preferably sulfuric acid in acetonitrile, or with hydrogen fluoride or tetrabutylammonium fluoride in tetrahydrofuran at a temperature ranged from 0° C. to 40° C. for 1-24 hours. The E and Z isomers prepared by the above two methods may then be separated by chromatography.

III. Compounds Wherein $R_1$ is CO$_2$R

Compounds (1), (2), and (3) wherein $R_1$ is —CO$_2$R are prepared according to Reaction Scheme 8.

REACTION SCHEME 8

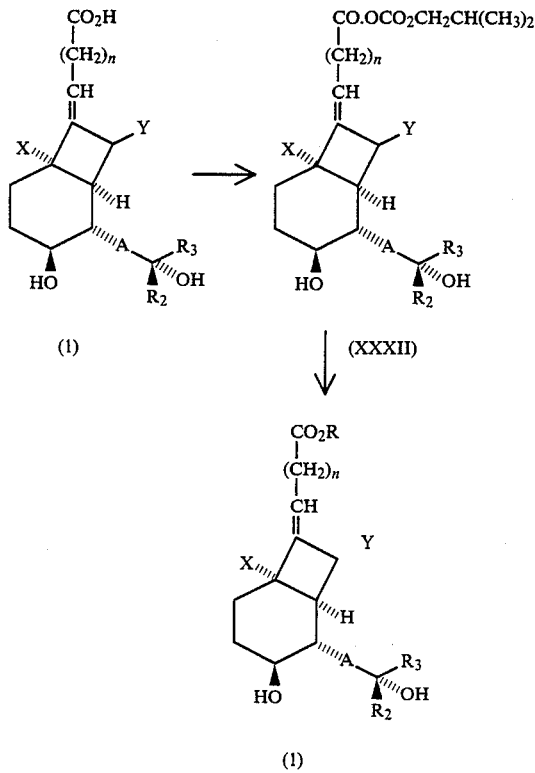

Reaction Scheme 8 demonstrates a method for conversion of (1) wherein $R_1$ is —CO$_2$H into (1) wherein $R_1$ is —CO$_2$R. By appropriate substitution of (1) wherein $R_1$ is —CO$_2$H by either (2) or (3) wherein $R_1$ is —CO$_2$H the reactions of Scheme 8 may be used to prepare (2) or (3) wherein $R_1$ is —CO$_2$R. In this method a compound of formula (1), (2) or (3) wherein $R_1$ is —CO$_2$H is condensed with isobutyl chlorocarbonate to give an anhydride represented in the case of (1) by formula (XXXII). Compound (XXXII) is reacted with a substituted phenol to give compounds (1) wherein $R_1$ is —CO$_2$R. The phenols used in this Scheme are known in the prior art and their application to the preparation of phenyl esters is described in *J. Pharm. Sci.* 68, 833 (1979).

In summary, the compounds of the present invention are made by the procedures below:

(1) A process for the preparation of a compound of formula (1), (2) or (3), wherein:

A is —C≡C—, —HC=CH—, —CH$_2$CH$_2$— or —CH=CHCH$_2$—;

X is lower alkoxy, hydroxy or (2,2,2)-trifluoroethoxy;

Y is hydrogen, exo-(lower alkyl) or endo-(lower alkyl);

n is an integer of 2-4;

$R_1$ is —CO$_2$H, and the olefin formed by the $R_1$(CH$_2$)$_n$CH= moiety is either (E) or (Z);

$R_2$ is hydrogen or methyl, or optionally —CH=CH$_2$ when A is —CH=CHCH$_2$—; and $R_3$ is linear or branched alkyl, alkenyl or alkynyl having 5-10 carbon atoms,

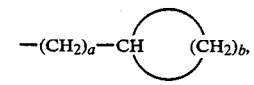

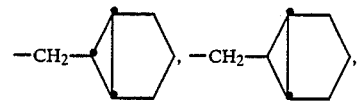

—(CH$_2$)$_m$-phenyl or CH$_2$O-phenyl;

in which phenyl may be optionally substituted with lower alkyl, lower alkoxy, trifluoromethyl, or halogen.

in which:

a is an integer of 0, 1 or 2;

b is an integer of 3-7;

m is an integer of 0, 1 or 2;

comprises reacting a compound of the formula:

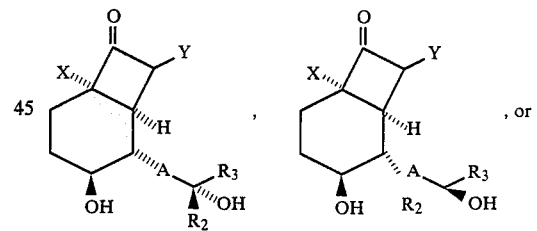

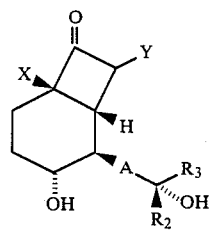

where A, X, Y, $R_2$ and $R_3$ are as defined above, with a phosphorus ylide of formula (R')$_3$P=CH(CH$_2$)$_n$—CO$_2$H, where R' is optionally substituted phenyl and n is as defined in (1) above, or any appropriately chosen stabilized anion or ylide of formula P'—$\overline{\text{CH}}$—(CH$_2$)$_n$CO$_2$—, where P' is a residue normally associated with olefination reactions and n is as defined above.

(2) A process for the preparation of a compound of formula (1), (2) or (3) wherein A, X, Y, $R_2$ and $R_3$ are as defined above, $R_1$ is —$CO_2H$ and n is 2 comprises reacting a compound of the formula

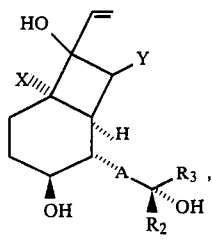 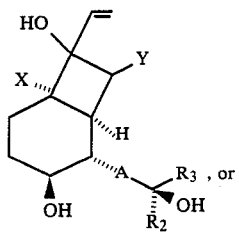

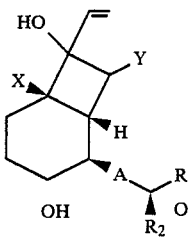

where A, X, Y, $R_2$ and $R_3$ are as defined above, with ethyl orthoacetate in the presence of an acid catalyst.

(3) A process for the preparation of an ester of a compound of formula (1), (2) or (3) comprises reacting a compound of the general formula

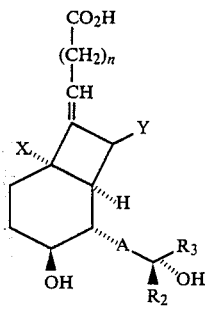 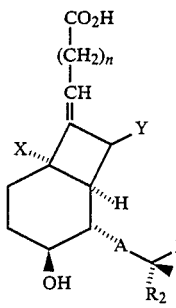

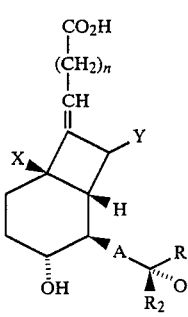

where A, X, Y, $R_2$ and $R_3$ are as defined in (1) above, with:
(a) a diazoalkane of formula $RCHN_2$, where R is hydrogen or alkyl; or
(b) an alkyl halide of formula RHal, where R is alkyl and Hal is chlorine, bromine or iodine, in the presence of a base; or
(c) a chlorocarbonate of formula $ClCO_2R$, where R is alkyl in the presence of a base followed by a phenol; or (d) an alcohol or phenol of formula ROH in the presence of an activating agent.

(4) The process for preparing the compounds of formula (1), (2) or (3) where $R_1$ is —$CH_2OH$ comprises reacting a compound of the formula

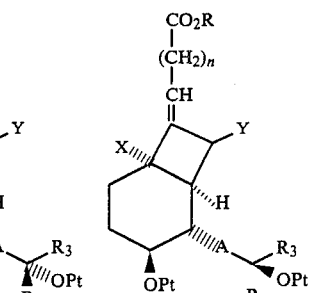

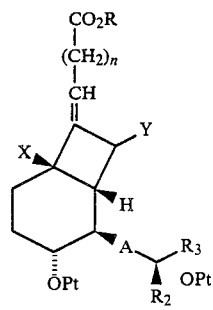

where A, X, Y, R, $R_2$ and $R_3$ are as defined above, and Pt is a protecting group, with a hydride reducing agent followed by removal of the protecting group.

(5) The process for preparing the compounds of formula (1), (2) or (3) where $R_1$ is —CHO comprises reacting a compound of the formula

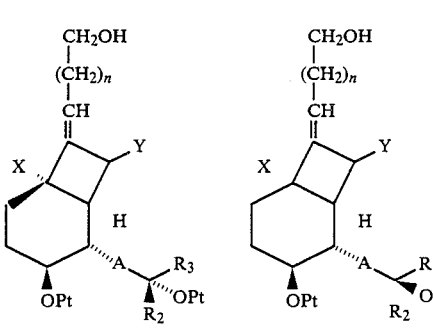

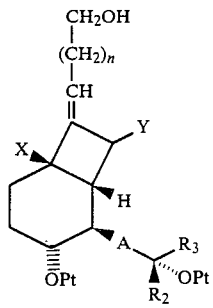

where A, X, Y, $R_2$ and $R_3$ are as defined above, and Pt is a protecting group, with a suitable oxidizing agent followed by removal of the protecting group.

(6) The process for preparing the enantiomers of formula (XLV) and (XLVI), where X is lower alkoxy, comprises reacting a compound of the formula

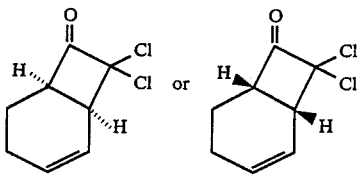

with an alcohol of formula XH, where X is defined as above, followed by treatment with a dechlorinating agent.

(7) The process for preparing the enantiomers of formula (L), (LI), (LII) or (LIII), where X is lower alkoxy and Y is exo-(lower alkyl) or endo-(lower alkyl), comprises reacting a compound of the formula

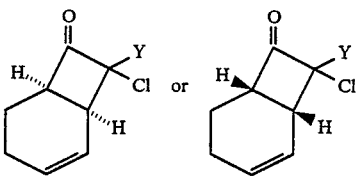

where Y is as defined above, with an alcohol of formula XH, where X is as defined above.

UTILITY AND ADMINISTRATION

The compounds of the present invention are useful for the treatment of cardiovascular disorders; in particular they are vasodilators, and inhibit accumulation of cholesterol in the vascular wall and in plasma. They are also potent inhibitors of the aggregation of platelets and the release from them of pro-coagulant and pro-atherosclerotic factors. Accordingly, these compounds are useful in treating and preventing cardiovascular disorders involving atherosclerosis, thrombotic and vasospastic conditions. They also are useful antihypertensive and cholesterol lowering agents.

The compounds of this invention display the spectrum of activities associated with prostacyclin. However, in contrast to prostacyclin, whose therapeutic potential is severely compromised by its extreme chemical instability, the compounds of our invention retain high biological activity while displaying much greater chemical stability, a combination of attributes identifying them as promising agents for prophylactic and/or therapeutic use particularly in the treatment of cardiovascular dysfunction and disease. Many of these compounds are potent antihypertensives. Alternatively, many of these compounds are selective in their antithrombotic effect, and they achieve this therapeutic effect without substantially affecting blood pressure.

Administration of the active compounds in the pharmaceutical composition described hereinafter can be via any of the accepted modes of administration for agents which affect the cardiovascular system. These methods include oral, parenteral, topical and otherwise systemic administration. Depending on the intended mode, the composition may be in the form of solid, semi-solid or liquid dosage forms, such as, for example, tablets, suppositories, pills, capsules, powders, liquids, suspension, or the like, preferably in unit dosage forms suitable for single administration of precise dosages. The composition will include a conventional pharmaceutical carrier or excipient and an active compound of formula (1), (2) or (3) and/or the pharmaceutically acceptable salts thereof and, in addition, may include other medicinal agents, pharmaceutical agents, carriers, adjuvants, etc.

The present invention further relates to a method for treating cardiovascular disorders in mammals, which method comprises administering to a subject in need thereof an effective amount of a compound selected from those represented by formulas (1), (2) or (3) or their pharmaceutically acceptable nontoxic salts or esters, or a pharmaceutical composition incorporating such compound(s) as an active ingredient.

The present invention still further relates to pharmaceutical compositions useful for treating cardiovascular disorders. These compositions comprise an effective amount of a compound selected from those represented by formulas (1), (2) or (3) or their pharmaceutically acceptable nontoxic salts or esters in acceptable, nontoxic carrier.

The amount of active compound administered will of course, be dependent on the subject being treated, the severity of the affliction, the manner of administration and the judgment of the prescribing physician. However, an effective dosage will be in the range of 0.001–15 mg/kg/day, preferably 0.01–3 mg/kg/day. For an average 70 kg human, this would amount to 0.07–1000 mg per day, or preferably 0.7–210 mg/day.

The novel compounds of this invention may be formulated with suitable pharmaceutical vehicles known in the art to form particularly effective cardiovascular compositions. Generally, an effective amount of active ingredient is about 0.001% w to about 10% w of the total formulated composition. The rest of the formulated composition will be about 90% w to about 99.999% w of a suitable excipient.

For solid compositions, conventional nontoxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences,* Mack Publishing Company, Easton, Pa., 15th Edition, 1975. The composition or formulation to be administered will, in any event, contain a quantity of the active compound(s) in an amount effective to alleviate the symptoms of the subject being treated.

Parenteral administration is generally characterized by injection, either subcutaneously, intramuscularly or intravenously. Injectibles can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of nontoxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

For systemic administration via suppository, traditional binders and carriers include, e.g. polyalkylene glycols or triglycerides. Such suppositories may be formed from mixtures containing active ingredient in the range of 0.1%–10%; preferably 1–2%.

The following Preparations and Examples serve to illustrate the invention and make the invention enabling. They should not be construed as narrowing it or limiting its scope in any way. For the sake of convenience and clarity the compounds that exemplify the Preparations and Examples are named as pure enantiomers. It should be understood that the compounds may be equally prepared as racemic mixtures or as other enantiomers by the same procedures.

PREPARATION 1

Preparation of 8,8-dichlorobicyclo[4.2.0]oct-2-en-7-one (II) and related compounds of formula (IIB) and (IIC)

A. A mixture of 34.0 g of cyclohexadiene and 35.0 g of dichloroacetyl chloride in 300 ml of diethyl ether under nitrogen was refluxed while adding 31.5 g of triethylamine dropwise over a period of 3 hours. The mixture was then stirred at room temperature for 20 hours and filtered. The filtrate was washed with brine, 1N hydrochloric acid, saturated sodium bicarbonate and then dried over anhydrous sodium sulfate. The solvent was removed under reduced pressure and the residue distilled to give 32 g of 8,8-dichlorobicyclo[4.2.0]oct-2-en-7-one.

B. Similarly, starting from 2-chloropropionyl chloride in place of dichloroacetyl chloride, the following mixture of compounds of formula (IIB) and (IIC) was obtained:
8-endo-chloro-8-exo-methylbicyclo[4.2.0]oct-2-en-7-one; and
8-exo-chloro-8-endo-methylbicyclo[4.2.0]oct-2-en-7-one,
which were separated by chromatography on silica gel, eluting with a mixture of methylene chloride and hexane (1:1).

Similarly, starting with the appropriate 2-chloroalkanoyl chloride in place of 2-chloropropionyl chloride in preparation 1.A. above, the following mixtures of compounds of formula (IIB) and (IIC) are prepared:
8-exo-chloro-8-endo-ethylbicyclo[4.2.0]oct-2-en-7-one, and
8-endo-chloro-8-exo-ethylbicyclo[4.2.0]oct-2-en-7-one;
8-exo-chloro-8-endo-n-butylbicyclo[4.2.0]oct-2-en-7-one; and
8-endo-chloro-8-exo-n-butylbicyclo[4.2.0]oct-2-en-7-one.

PREPARATION 2

Preparation of 6-methoxybicyclo[4.2.0]oct-2-en-7-one and related compounds of formula (III) where Y is H A. To a stirred solution of 60 g of 8,8-dichlorobicyclo[4.2.0]oct-2-en-7-one in 500 ml of methanol under nitrogen at room temperature was added 48 ml of triethylamine over a period of 1 hour. The mixture was stirred for 30 minutes, then 90 g of ammonium chloride and 60 g of zinc-copper couple (as a powder) was added. The reaction mixture was stirred at room temperature for 2.5 hours, filtered through celite and the solvent removed under reduced pressure. The residue was dissolved in ethyl acetate, washed with brine, dried over anhydrous sodium sulfate and the solvent was distilled under vacuum, giving 32 g of 6-methoxybicyclo[4.2.0]oct-2-en-7-one.

B. Similarly, substituting 2,2,2-trifluoroethanol for methanol in preparation 2.A. above, the following compound was prepared:
6-(2,2,2-trifluoroethoxy)bicyclo[4.2.0]oct-2-en-7-one.

C. Similarly, starting with (1S,6R)-8,8-dichlorobicyclo[4.2.0]oct-2-en-7-one, prepared as shown in Preparation 22, in place of the racemic compound in Preparation 2.A. above, (1S,6S)-6-methoxybicyclo[4.2.0]oct-2-en-7-one is prepared. Similarly, starting with the (1R,6S)-compound, (1R,6R)-6-methoxybicyclo[4.2.0]oct-2-en-7-one is prepared.

D. Similarly, replacing methanol in Preparation 2.A. above with the appropriate alcohol, the following exemplary compounds of formula (III) where Y is H are made:
6-ethoxybicyclo[4.2.0]oct-2-en-7-one;
6-propoxybicyclo[4.2.0]oct-2-en-7-one;
6-butoxybicyclo[4.2.0]oct-2-en-7-one; and
6-isobutoxybicyclo[4.2.0]oct-2-en-7-one.

PREPARATION 3

Preparation of 6-methoxy-8-endo-methylbicyclo[4.2.0]oct-2-en-7-one and related compounds of formula (III) where Y is lower alkyl A. A solution of 1.0 g of 8-exo-chloro-8-endo-methylbicyclo[4.2.0]oct-2-en-7-one, prepared as shown in Preparation 1B, in 100 ml of methanol was stirred at room temperature while adding 0.6 ml of triethylamine dropwise over a period of 1 hour. Stirring was continued for a further 15 minutes then methanol was removed from the mixture under reduced pressure. The residue was partitioned between diethyl ether and brine solution and the organic layer dried over anhydrous sodium sulfate. Solvent was removed from the filtrate under reduced pressure, and the residue chromatographed on silica gel, eluting with 12% ethyl acetate in hexane, to give 830 mg of 6-methoxy-8-endo-methylbicyclo[4.2.0]oct-2-en-7-one.

B. Similarly, replacing 8-exo-chloro-8-endo-methylbicyclo[4.2.0]oct-2-en-7-one with the 8-exo-methyl isomer in paragraph 3.A. above, the corresponding compound of formula (III) was prepared i.e.
6-methoxy-8-exo-methylbicyclo[4.2.0]-oct-2en-7-one.

C. Similarly, starting with (1S,6R)-8-exo-chloro-8-endomethylbicyclo[4.2.0]oct-2-en-7-one, prepared as shown in Preparation 22, the optically active compound (1R,6S)-6-methoxy-8-endo-methylbicyclo[4.2.0]oct-2-en-7-one is prepared, and starting with the (1R,6S)isomer, (1S,6R)-6-methoxy-8-endo-methylbicyclo[4.2.-0]oct-2-en-7-one is prepared.

Similarly, (1R,6S)-6-methoxy-8-exo-methylbicyclo[4.2.0]oct-2-en-7-one and (1S,6R)-6-methoxy-8-exo-methylbicyclo[4.2.0]oct-2-en-7-one are prepared.

D. Similarly, replacing 8-exo-chloro-8-endo-methylbicyclo[4.2.0]oct-2-en-7-one with the appropriate compound of formula (IIB) or (IIC), the following exemplary compounds of formula (III) where Y is exo or endo-(lower alkyl) are prepared:
6-(2,2,2-trifluoroethoxy)-8-methylbicyclo[4.2.0]oct-2-en-7one;
6-ethoxy-8-methylbicyclo[4.2.0]oct-2-en-7-one;
6-propoxy-8-methylbicyclo[4.2.0]oct-2-en-7-one;
6-n-butoxy-8-methylbicyclo[4.2.0]oct-2-en-7-one;
6-isobutoxy-8-methylbicyclo[4.2.0]oct-2-en-7-one;
6-methoxy-8-ethylbicyclo[4.2.0]oct-2-en-7-one;
6-methoxy-8-n-butylbicyclo[4.2.0]oct-2-en-7-one; and
6-n-butoxy-8-n-butylbicyclo[4.2.0]oct-2-en-7-one.

PREPARATION 4

Preparation of spiro[6-methoxybicyclo[4.2.0]oct-2-ene-7,2''-(1'',3''-dioxolane)] and related compounds of formula (IV)

A. A mixture of 6.4 g of 6-methoxybicyclo[4.2.0]oct-2-en-7-one (III), 18.62 g of ethylene glycol, 100 ml of benzene, and 25 mg of p-toluenesulfonic acid was heated at reflux for 4 hr using a Dean-Stark trap to effect continuous removal of water. The cooled reaction mixture was poured on to 100 ml saturated sodium bicarbonate solution and the resulting mixture extracted with three 75 ml portions of diethyl ether. The combined organic extract was washed with 100 ml saturated sodium chloride solution and then dried over sodium sulfate. The solvent was removed under vacuum and the residue distilled under vacuum to give 7.12 g of spiro[6-methoxybicyclo[4.2.0]oct-2-ene-7,2''-(1'',3''-dioxolane)] (IV).

B. Similarly, following the procedure of paragraph 4.A. above, replacing 6-methoxybicyclo[4.2.0]oct-2-en-7-one with the appropriate compounds of formula (III) the following compounds of formula (IV) were prepared:
Sprio[6-(2,2,2-trifluoroethoxy)bicyclo[4.2.0]oct-2-ene-7,2''-(1'',3''-dioxolane)];
Spiro[6-methoxy-8-exo-methylbicyclo[4.2.0]oct-2-ene-7,2''-(1'',3''-dioxolane)]; and
Spiro[6-methoxy-8-endo-methylbicyclo]4.2.0]oct-2-ene-7,2''-(1'',3''-dioxolane)].

C. Similarly, following the procedure of paragraph 4.A. above, replacing 6-methoxybicyclo[4.2.0]oct-2-en-7-one with the appropriate optically active compounds, prepared as shown in Preparations 2C and 3C, the following exemplary compounds of formula (IVA) are prepared:
(1S,6S)-Spiro[6-methoxybicyclo[4.2.0]oct-2-ene-7,2''-(1'',3''-dioxolane)]
(1R,6R)-Spiro[6-methoxybicyclo[4.2.0]oct-2-ene-7,2''-(1'',3''-dioxolane)]
(1S,6R)-Spiro[6-methoxy-8-exo-methylbicyclo[4.2.-0]oct-2-ene-7,2'' −(1'',3''-dioxolane)]
(1R,6S)-Spiro[6-methoxy-8-exo-methylbicyclo[4.2-0]oct-2-ene-7,2'' −(1'',3''-dioxolane)]
(1S,6R)-Spiro[6-methoxy-8-endo-methylbicyclo[4.2-0]oct-2-ene-7,2'' −(1'',3''-dioxolane)]
(1R,6S)-Spiro[6-methoxy-8-endo-methylbicyclo[4.2-0]oct-2-ene-7,2'' −(1'',3''-dioxolane)]

D. Similarly, following the procedures of paragraph 4.A. above, the following representative compounds of formula (IV) where Y is H are prepared:
Spiro[6-ethoxybicyclo]4.2.0oct-2-ene-7,2''-(1'',3''-dioxolane)];
Spiro[6-propoxybicyclo[4.2.0]oct-2-ene-7,2''-(1'',3''-dioxolane)];
Spiro[6-butoxybicyclo[4.2.0]oct-2-ene-7,2''-(1'',3''-dioxolane)]; and
Spiro[6-isobutoxybicyclo[4.2.0]oct-2-ene-7,2''-(1'',3''-dioxolane)].

E. Similarly, following the procedures of paragraph 4.A. above, the following representative compounds of formula (IV), where Y is exo or endo-(lower alkyl), are prepared.
Spiro[6-trifluoroethoxy-8-methylbicyclo[4.2.0]oct-2-ene-7,2''-(1'',3''-dioxolane)];
Spiro[6-ethoxy-8-methylbicyclo[4.2.0]oct-2-ene-7,2''-(1'',3''-dioxolane)];
Spiro[6-propoxy-8-methylbicyclo[4.2.0]oct-2-ene-7,2''-(1'',3''-dioxolane)];
Spiro[6-n-butoxy-8-methylbicyclo[4.2.0]oct-2-ene-7,2''-(1'',3''-dioxolane)];
Spiro[6-isobutoxy-8-methylbicyclo[4.2.0]oct-2-ene-7,2''-(1'',3''-dioxolane)].
Spriro[6-methoxy-8-ethylbicyclo[4.2.0]oct-2-ene-7,2''-(1'',3''-dioxolane)];
Spiro[6-methoxy-8-n-butylbicyclo[4.2.0]oct-2-ene-7,2''-(1'',3''-dioxolane)]; and
Spiro[6-n-butoxy-8-n-butylbicyclo[4.2.0]oct-2-ene-7,2''-(1'',3''-dioxolane)].

PREPARATION 5

Preparation of (1RS,2SR,3RS,6RS)-Spiro[2,3-epoxy-6-methoxybicyclo[4.2.0]octane-7,2''-(1'',3''-dioxolane)] and (1RS,2RS,3SR,6RS)-Spiro[2,3-epoxy-6-methoxybicyclo[4.2.0]octane-7,2''-(1'',3''-dioxolane)] and related compounds of formulas (VI) and (VII)

A. To a stirred solution of 5 g of spiro[6-methoxybicyclo[4.2.0]oct-2-ene-7,2''-(1'',3''-dioxolane)], prepared according to Preparation 4, in 40 ml acetone and 20 ml water at 0° C. was added 4.76 g of N-bromoacetamide over 1 hour. This mixture was stirred at room temperature for 20 hours. To this solution was added 12.4 g potassium carbonate and the resulting mixture was stirred at room temperature for 3 days. The mixture was saturated with sodium chloride and the resulting mixture extracted with four 150 ml portions of diethyl ether. The combined organic extract was washed with 100 ml of saturated sodium chloride solution and dried over sodium sulfate. Removal of solvent in vacuum and chromatographic purification of the residue on silica gel eluting with 15% ethyl acetate-hexane gave 3.45 g of a ca. 4:1 mixture of (1RS,2SR,3RS,6RS)-Spiro[2,3-epoxy-6-methoxybicyclo[4.2.0]octane-7,2''-(1'',3''-dioxolane)] and (1RS,2RS,3SR,6RS)-Spiro[2,3-epoxy-6-methoxybicyclo[4.2.0]octane-7,2''-(1'',3''-dioxolane)].

Similarly, starting with the appropriate compounds of formula (IV) in place of spiro[6-methoxybicyclo[4.2.-0]oct-2-ene-7,2''-(1'',3''-dioxolane)] and following the procedures of paragraph 5.A. above, the following mixtures of compounds of formula (VI) and (VII) were prepared:
(1RS,2SR,3RS,6RS)-Spiro[2,3-epoxy-6-(2,2,2-trifluoroethoxy)bicyclo[4.2.0]octane-7,2''-(1'',3''-dioxolane)], and (1RS,2RS,3SR,6RS)-Spiro[2,3-epoxy-6-(2,2,2-trifluoroethoxy)bicyclo[4.2.0]octane-7,2''-(1'',3''-dioxolane)];

(1RS,2SR,3RS,6RS)-Spiro[2,3-epoxy-6-methoxy-8-exo-methylbicyclo[4.2.0]octane-7,2''-(1'',3''-dioxolane)], and (1RS,2RS,3SR,6RS)-Spiro[2,3-epoxy-6-methoxy-8-exo-methylbicyclo[4.2.0]octane-7,2''-(1'',3''-dioxolane)];

(1RS,2SR,3RS,6RS)-Spiro[2,3-epoxy-6-methoxy-8-endo-methylbicyclo[4.2.0]octane-7,2''-(1'',3''-dioxolane)], and (1RS,2RS,3SR,6RS)-Spiro[2,3-epoxy-6-methoxy-8-endo-methylbicyclo[4.2.0]octane-7,2''-(1'',3''-dioxolane)].

C. Similarly, starting with the appropriate compounds of formula (IVA), prepared as shown in Preparation 4.C., in place of spiro[6-methoxybicyclo[4.2.0]oct-2-ene-7,2''-(1'',3''-dioxolane)] and following the procedures of paragraph 5A above, the following exemplary mixtures of compounds of formula (VIA) and (VIIA) are prepared:

(1S,2R,3S,6S)- and (1S,2S,3R,6S)-Spiro-[2,3-epoxy-6-methoxybicyclo[4.2.0]octane-7,2''-(1'',3''-dioxolane)].

(1R,2R,3S6R,)- and (1R,2S,3R,6R)-Spiro-[2,3-epoxy-6-methoxybicyclo[4.2.0]octane-7,2''-(1'',3''-dioxolane)].

(1S,2R,3S,6S)- and (1S,2S,3R,6S)-Spiro-[2,3-epoxy-6-methoxy-8-exo-methylbicyclo[4.2.0]octane-7,2''-(1'',3''-dioxolane)].

(1R,2R,3S,6R)- and (1R,2S,3R,6R)-Spiro-[2,3-epoxy-6-methoxy-8-exo-methylbicyclo[4.2.0]octane-7,2''-(1'',3''-dioxolane)].

(1S,2R,3S,6S)- and (1S,2S,3R, 6S)-Spiro-[2,3,-epoxy-6-methoxy-8-endo-methylbicyclo[4.2.0]octane-7,2''-(1'',3''-dioxolane)].

(1R,2R,3S,6R)- and (1R,2S,3R,6R)-Spiro-[2,3-epoxy-6-methoxy-8-endo-methylbicyclo[4.2.0]octane-7,2''-(1'',3''-dioxolane)].

D. Similarly, following the procedures of 5.A. above, the following exemplary mixtures of compounds of formula (VI) and (VII), where Y is H, or exo or endo-(lower alkyl) are prepared:

(1RS,2SR,3RS,6RS)-Spiro[2,3-epoxy-6-ethoxybicyclo[4.2.0]octane-7,2''-(1''3''-dioxolane)], and (1RS,2RS,3SR,6RS)-Spiro[2,3-epoxy-6-ethoxybicyclo[4.2.0]octane-7,2''-(1'',3''-dioxolane)];

(1RS,2SR,3RS,6RS)-Spiro[2,3-epxoy-6-n-butoxybicyclo[4.2.0]octane-7,2''-(1'',3''-dioxolane)], (1RS,2RS,3SR,6RS)-Spiro[2,3-epoxy-6-n-butoxybicyclo[4.2.0]octane-7,2''-(1'',3''-dioxolane)];

(1RS,2SR,3RS,6RS)-Spiro[2,3-epoxy-6-isobutoxybicyclo[4.2.0]octane-7,2''-(1'',3''-dioxolane)];

(1RS,2RS,3SR,6RS)-Spiro[2,3-epoxy-6-isobutoxybicyclo[4.2.0]octane-7,2''-(1'',3''-dioxolane)];

(1RS,2SR,3RS,6RS)-Spiro[2,3-epoxy-6-(2,2,2-trifluoroethoxy)-8-methylbicyclo[4.2.0]octane-7,2''-(1'',3''-dioxolane)], and (1RS,2RS,3SR,6RS)-Spiro[2,3-epoxy-6-(2,2,2-trifluoroethoxy)-8-methylbicyclo[4.2.0]octane-7,2''-(1'',3''-dioxolane)];

(1RS,2SR,3RS,6RS)-Spiro[2,3-epoxy-6-ethoxy-8-methylbicyclo[4.2.0]octane-7,2''-(1'',3''-dioxolane)], and (1RS,2RS,3SR,6RS)-Spiro[2,3-epoxy-6-ethoxy-8-methylbicyclo[4.2.0]octane-7,2''-(1'',3''-dioxolanew)];

(1RS,2SR,3RS,6RS)-Spiro[2,3-epoxy-6-n-butoxy-8-methylbicyclo[4.2.0]octane-7,2''-(1'',3''-dioxolane)], and (1RS,2RS,3SR,6RS)-Spiro[2,3-epoxy-6-n-butoxy-8-methylbicyclo[4.2.0]octane-7,2''-(1'',3''-dioxolane)];

(1RS,2SR,3RS,6RS)-Spiro[2,3-epoxy-6-methoxy-8-ethylbicyclo[4.2.0]octane-7,2''-(1'',3''-dioxolane)], and (1RS,2RS,3SR,6RS)-Spiro[2,3-epoxy-6-methoxy-8-ethylbicyclo[4.2.0]octane-7,2''-(1'',3''-dioxolane)];

(1RS,2SR,3RS,6RS)-Spiro[2,3-epoxy-6-methoxy-8-n-butylbicyclo[4.2.0]octane-7,2''-(1'',3''-dioxolane)], and (1RS,2RS,3SR,6RS)-Spiro[2,3-epoxy-6-methoxy-8-n-butylbicyclo[4.2.0]octane-7,2''-(1'',3''-dioxolane)];

(1RS,2SR,3RS,6RS)-Spiro[2,3-epoxy-6-n-butoxy-8-n-butylbicyclo[4.2.0]octane-7,2''-(1'',3''-dioxolane)], and (1RS,2RS,3SR,6RS)-Spiro[2,3-epoxy-6-n-butoxy-8-n-butylbicyclo[4.2.0]octane-7,2''-(1'',3''-dioxolane)].

PREPARATION 6

Alternative preparation of
(1RS,2SR,3RS,6RS)-Spiro[2,3-epoxy-6-methoxybicyclo[4.2.0]octane-7,2''-(1'',3''-dioxolane)] and
(1RS,2RS,3SR,6RS)-Spiro[2,3-epoxy-6-methoxybicyclo[4.2.0]octane-7,2''-(1'',3''-dioxolane)] and related compounds of formulas (VI) and (VII)

A. A mixture of 5.4 g of spiro[6-methoxybicyclo[4.2.0]oct-2-ene-7,2''-(1'',3''-dioxolane)] and 5.5 g of m-chloroperbenzoic acid in 80 ml of dichloromethane was stirred at room temperature for 3 hours. The mixture was then washed with aqueous sodium bicarbonate solution, dried over anhydrous sodium sulfate and the solvent removed under reduced pressure. The residue was chromatographed on silica gel, eluting with ethyl acetatehexane (1:1) to give a mixture of the endo and exo epoxides in a 2:2 ratio, namely:

(1RS,2SR,3RS,6RS)-spiro[2,3-epoxy-6-methoxybicyclo[4.2.0]octane-7,2''-(1'',3''-dioxolane)] and (1RS,2RS,3SR,6RS)-spiro[2,3-epoxy-6-methoxybicyclo[4.2.0]octane-7,2''-(1'',3''-dioxolane)];

B. Similarly, starting with the appropriate compounds of formula (IVA), prepared as shown in Preparation 4.C., in place of spiro[6-methoxybicyclo[4.2.0]oct-2-ene-7,2''-(1'',3''-dioxolane)] and following the procedures of paragraph 6.A. above, the following exemplary mixtures of compounds of formula (VIA) and (VIIA) are prepared:

(1S,2R,3S,6S)- and (1S,2S,3R,6S)-Spiro-[2,3-epoxy-6-methoxybicyclo[4.2.0]octane-7,2''-dioxolane)].

1R,2R,3S,6R)- and (1R,2S,3R,6R)-Spiro-[2,3-epoxy-6-methoxybicyclo[4.2.0]octane-7,2''-(1'',3''-dioxolane)].

(1S,2R,3S,6S)- and (1S,2S,3R,6S)-Spiro-[2,3-epoxy-6-methoxy-8-exo-methylbicyclo[4.2.0]octane-7,2''-(1'',3''-dioxolane)].

(1R,2R,3S,6R)- and (1R,2S,3R,6R)-Spiro-[2,3-epoxy-6-methoxy-8-exo-methylbicyclo[4.2.0]octane-7,2''-(1'',3''-dioxolane)].

(1S,2R,3S,6S)- and (1S,2S,3R,6S)-[2,3-epoxy-6-methoxy-8-endo-methylbicyclo[4.2.0]octane-7,2''-(1'',3''-dioxolane)].

(1R,2R,3S,6R)- and (1R,2S,3R,6R)-Spiro-[2,3-epoxy-6-methoxy-8-endo-methylbicyclo[4.2.0]octane-7,2''-(1'',3''-dioxolane)].

C. Similarly, starting with the appropriate compounds of formula (IV) in place of spiro[6-methoxybicyclo[4.2.0]oct-2-ene-7,2''-(1'',3''-dioxolane)] and following the procedures of paragraph 6.A. above, the following exemplary mixtures of compounds of formula (VI) and (VII) where Y is H, or exo or endo-(lower alkyl) are prepared:

(1RS,2SR,3RS,6RS)-Spiro[2,3-epoxy-6-(2,2,2-trifluoro-ethoxy)bicyclo[4.2.0]octane-7,2''-(1'',3''-dioxolane)], and
(1RS,2RS,3SR,6RS)-Spiro[2,3-epoxy-6-(2,2,2-trifluoro-ethoxy)bicyclo[4.2.0]octane-7,2''-(1'',3''-dioxolane)];
(1RS,2SR,3RS,6RS)-Spiro[2,3-epoxy-6-methoxy-8-methylbicyclo[4.2.0]octane-7,2''-(1'',3''-dioxolane)], and
(1RS,2RS,3SR,6RS)-Spiro[2,3-epoxy-6-methoxy-8-methylbicyclo[4.2.0]octane-7,2''-(1'',3''-dioxolane)];
(1RS,2SR,3RS,6RS)-Spiro[2,3-epoxy-6-ethoxybicyclo[4.2.0]octane-7,2''-(1'',3''-dioxolane)], and
(1RS,2RS,3SR,6RS)-Spiro[2,3-epoxy-6-ethoxybicyclo[4.2.0]octane-7,2''-(1'',3''-dioxolane)];
(1RS,2SR,3RS,6RS)-Spiro[2,3-epoxy-6-n-butoxybicyclo[4.2.0]octane-7,2''-(1'',3''-dioxolane)], and
(1RS,2RS,3SR,6RS)-Spiro[2,3-epoxy-6-n-butoxybicyclo[4.2.0]octane-7,2''-(1'',3''-dioxolane)];
(1RS,2SR,3RS,6RS)-Spiro[2,3-epoxy-6-isobutoxybicyclo[4.2.0]octane-7,2''-(1'',3''-dioxolane)], and
(1RS,2RS,3SR,6RS)-Spiro[2,3-epoxy-6-isobutoxybicyclo[4.2.0]octane-7,2''-(1'',3''-dioxolane)];
(1RS,2SR,3RS,6RS)-Spiro[2,3-epoxy-6-(2,2,2-trifluoro-ethoxy)-8-methylbicyclo[4.2.0]octane-7,2''-(1'',3''-dioxolane)], and
(1RS,2RS,3SR,6RS)-Spiro[2,3-epoxy-6(2,2,2-trifluoro-ethoxy)-8-methylbicyclo[4.2.0]octane-7,2''-(1'',3''-dioxolane)];
(1RS,2SR,3RS,6RS)-Spiro[2,3-epoxy-6-ethoxy-8-methylbicyclo[4.2.0]octane-7,2''-(1'',3''-dioxolane)], and
(1RS,2RS,3SR,6RS,)-Spiro[2,3-epoxy-6-ethoxy-8-methylbicyclo[4.2.0]octane-7,2''-(1'',3''-dioxolanew)];
(1RS,2SR,3RS,6RS)-Spiro[2,3-epoxy-6-n-butoxy-8-methylbicyclo[4.2.0]octane-7,2''-(1'',3''-dioxolane)], and
(1RS,2RS,3SR,6RS)-Spiro[2,3-epoxy-6-n-butoxy-8-methylbicyclo[4.2.0]octane-7,2''-(1'',3''-dioxolane)];
(1RS,2SR,3RS,6RS)-Spiro[2,3-epoxy-6-methoxy-8-ethylbicyclo[4.2.0]octane-7,2''-(1'',3''-dioxolane)], and
(1RS,2RS,3SR,6RS)-Spiro[2,3-epoxy-6-methoxy-8-ethylbicyclo[4.2.0]octane-7,2''-(1'',3''-dioxolane)];
(1RS,2SR,3RS,6RS)-Spiro[2,3-epoxy-6-methoxy-8-n-butylbicyclo[4.2.0]octane-7,2''-(1'',3''-dioxolane)], and
(1RS,2RS,3SR,6RS)-Spiro[2,3-epoxy-6-methoxy-8-n-butylbicyclo[4.2.0]octane-7,2''-(1'',3''-dioxolane)];
(1RS,2SR,3RS,6RS)-Spiro[2,3-epoxy-6-n-butoxy-8-n-butylbicyclo[4.2.0]octane-7,2''-(1'',3''-dioxolane)], and
(1RS,2RS,3SR,6RS)-Spiro[2,3-epoxy-6-n-butoxy-8-n-butylbicyclo[4.2.0]octane-7,2''-(1'',3''-dioxolane)].

PREPARATION 7

Preparation of 3-Hydroxy-1-Alkynes of Formula (XVII)

A. A rapid stream of acetylene was passed through a solution of 2M methyl magnesium bromide (100 ml) in THF until no more methane evolution was observed. 10 g of hexanal was added at 0° C., stirred for ½ h and a saturated solution of NH$_4$Cl was added. The organic product was isolated by extraction with ether. The ether solution was washed with water, brine, dried over MgSO$_4$ and evaporated to give a liquid, which was purified by distillation, to give oct-1-yn-3-ol, b.p. 85° C./0.1 mm Hg.

B. Similarly, following the procedure of 7.A. above, the following representative compounds of formula (XVII) are prepared:
3-cyclohexylprop-1-yn-3-ol;
dec-1-yn-3-ol;
tridec-1-yn-3-ol;
(R)-5-methylnon-1-yn-3-ol;
non-1-yn-3-ol;
4-phenylbut-1-yn-3-ol;
5-phenylpent-1-yn-3-ol;
3-methyl-4-phenylbut-1-yn-3-ol;
4-m-trifluoromethylphenylbut-1-yn-3-ol;
4-endo-bicyclo[3.1.0]hex-6-ylbut-1-yn-3-ol;
4-exo-bicyclo[3.1.0]hex-6-ylbut-1-yn-3-ol;
3-methyl-3-cyclobutylprop-1-yn-3-ol;
3-methyl-3-cyclopentylprop-1-yn-3-ol;
3-cyclopentylprop-1-yn-3-ol;
4-cyclopentylbut-1-yn-3-ol,
4-cyclohexylbut-1-yn-3-ol.
4-phenoxybut-1-yn-3-ol, and
5,9-dimethyldec-1-yn-8-en-3-ol.

PREPARATION 8

Preparation of 3-Cyclohexylprop-1-yn-3-one and Related Compounds of Formula (VIII)

A. A solution of chromic acid was prepared by dissolving 106.88 g chromium trioxide in 400 ml water and then adding 92 ml concentrated sulfuric acid. This solution was added in dropwise fashion over a 3 hr. period to an ice cooled, stirred solution of 120 g 3-cyclohexyl-1-propyn-3-ol in 175 ml acetone. The resulting mixture was diluted with 500 ml water and the product was extracted into 1 liter of diethyl ether. The ether extract was washed with 250 ml saturated sodium bisulfite solution and was dried over sodium sulfate. The diethyl ether was removed by distillation under nitrogen atmosphere and the resulting residue was purified by Kugelrohr distillation (65° C., 0.1 mm Hg) to give 84.9 g of 3-cyclohexylprop-1-yn-3-one as an oil: MS m/z=136 (M+) Calcd. for C$_9$H$_{12}$O: C, 79.37; H, 8.88. Found: C, 79.24; H, 8.60.

B. In like manner, but replacing the 3-cyclohexyl-prop-1-yn-3-ol with oct-1-yn-3-ol, oct-1-yn-3-one was prepared.

C. Similarly, but starting with other appropriate compounds of formula (XVII), prepared in accordance with Preparation 7, the following exemplary compounds of Formula XVIII are prepared:
dec-1-yn-3-one;
tridec-1-yn-3-one;
(R)-5-methylnon-1-yn-3-one;
non-1-yn-3-one;
4-phenylbut-1-yn-3-one;
5-phenylpent-1-yn-3-one;
4-m-trifluoromethylphenylbut-1-yn-3-one;
4-endo-bicyclo[3.1.0]hex-6-ylbut-1-yn-3-one;
4-exo-bicyclo[3.1.0]hex-6-yl-1-butyn-3-one;
3-cyclopentylprop-1-yn-3-one;
4-cyclopentylbut-1-yn-3-one; and
4-cyclohexylbut-1-yn-3-one.

PREPARATION 9

Preparation of (S)-3-cyclohexylprop-1-yn-3-ol and Related Compounds of Formula (XIX)

A mixture of 1.6 liters 0.5M 9-borabicyclo[3.3.1]nonane in tetrahydrofuran and 122.6 g (−)-α-pinene, 99%+ pure, was heated at reflux under nitrogen for 4 hr., at which time the excess (−)-α-pinene and tetrahydrofuran were removed under vacuum to leave a thick oil. The contents of the flask were cooled to 0° C. and 80 g of 3-cyclohexylprop-1-yn-3-one, prepared according to Preparation 8, was added with stirring. The resulting mixture was allowed to warm to 23° C. and was stirred at that temperature for 16 hr. Excess S-Alpine borane was destroyed by adding 44 ml propionaldehyde and stirring at 23° C. for 1 hr. The liberated (−)-α-pinene was removed by vacuum distillation. The resulting mixture was diluted with 400 ml tetrahydrofuran followed by 300 ml 3N sodium hydroxide. To this stirred mixture was added in dropwise fashion 300 ml 30% hydrogen peroxide over 1 hr. The mixture was heated at 40° C. for 3 hr. After cooling, the mixture was extracted with diethyl ether and this extract was dried over magnesium sulfate. Evaporation of the solvent and purification of the residue by silica gel flash chromatography using 5% ethyl acetate-hexane gave 56 g of (S)-3-cyclohexyl prop-1-yn-3-ol, which by nmr analysis was shown to be 90% e.e. Recrystallization from hexane gave 45 g of the pure S isomer, mp 56°-58°, $[\alpha]_D^{25} = -11.1°$ (C=0.53, Et$_2$O)

B. In like manner, but replacing the 3-cyclohexylprop-1-yn-3-one with oct-1-yn-3-one, prepared as described in Preparation 8, we prepared (S)-1-octyn-3-ol; $[\alpha]_D^{25} = -39.7°$ (C=1, CHCl$_3$).

C. Similarly, but utilizing instead other suitable compounds of formula (XVIII), prepared according to Preparation 8, the following representative compounds of formula (XIX) are prepared:
(S)-dec-1-yn-3-ol;
(S)-tridec-1-yn-3-ol;
(3S,5R)-5-methylnon-1-yn-3-ol;
(S)-non-1-yn-3-ol;
(S)-4-phenylbut-1-yn-3-ol;
(S)-5-phenylpent-1-yn-3-ol;
(S)-4-m-trifluoromethylphenylbut-1-yn-3-ol;
(S)-4-endo-bicyclo[3.1.0]hex-6-ylbut-1-yn-3-ol;
(S)-4-exo-bicyclo[3.1.0]hex-6-ylbut-1-yn-3-ol;
(S)-3-cyclopentylprop-1-yn-3-ol;
(S)-3-cyclooctylprop-1-yn-3-ol;
(S)-4-cyclopentylbut-1-yn-3-ol; and
(S)-4-cyclohexylbut-1-yn-3-ol.

PREPARATION 10

Preparation of (S)-3-cyclohexylprop-1-yn-3-ol and Related Compounds of Formula (XIX) or (XXV)

A. A mixture of 50 g racemic 3-cyclohexyl-1-propyn-3-ol, prepared according to Preparation 7, 53.3 g phthalic anhydride, and 100 ml pyridine was heated at 90° C. for 4 hours. After cooling to 0° C. this mixture was added with stirring to a mixture of 350 ml concentrated hydrochloric acid and 900 ml ice. The oily solid that separated was dissolved in 600 ml diethyl ether. This solution was washed with saturated NaCl solution and dried over sodium sulfate. Evaporation and recrystallization from acetone/hexane gave the hemiphthalate, mp 136°-138° C. This hemiphthalate (38.5 g) was suspended in 80 ml dichloromethane and a solution of 16.2 g (−)-α-phenylethylamine in 250 ml dichloromethane added with stirring over 15 minutes. The mixture was filtered after 1 hour and the filtrate evaporated to give a mixture of diastereoisomeric salts. This mixture was recrystallized five times from acetonitrile to give 7 g of a pure diastereoisomeric salt mp 142°-143° C., $[\alpha]_D = -36.7$ (C=1, CHCl$_3$). This salt (2 g) was added to a stirred mixture of 25 ml 5% sodium carbonate and 25 ml diethyl ether. The ether layer was discarded and the aqueous layer extracted with 3 additional 25-ml portions of diethyl ether. The aqueous layer was acidified with 4N HCl and extracted thoroughly with diethyl ether. The ether extract was dried over sodium sulfate and evaporated to dryness to give 1.37 g of the hemiphthalate of (S)-3-cyclohexylprop-1-yn-3-ol, mp 70°-74° C., $[\alpha]_D = -35.8°$ (C=1, CHCl$_3$). The hemiphthalate was then stirred with excess aqueous 2N potassium hydroxide for 2 hours at 60° C., the mixture cooled to room temperature and extracted with diethyl ether. The organic layer was separated, dried over sodium sulfate and the solvent removed under reduced pressure to give (S)-3-cyclohexylprop-1-yn-3-ol, m.p. 56°-58° C., $[\alpha]_D^{25} = -11.2°$ (c=0.5, Et$_2$O).

B. Similarly, following the procedures of paragraph 10.A. above, but starting with other compounds of formula (XVII), prepared in accordance with Preparation 7, the following exemplary compounds of formula (XXV) are prepared:
(S)-oct-1-yn-3-ol;
(S)-dec-1-yn-3-ol;
(S)-tridec-1-yn-3-ol;
(3S,5R)-5-methylnon-1-yn-3-ol;
(S)-non-1-yn-3-ol;
(S)-4-phenylbut-1-yn-3-ol;
(S)-5-phenylpent-1-yn-3-ol;
(S)-4-m-trifluoromethylphenylbut-1-yn-3-ol;
(S)-4-endo-bicyclo[3.1.0]hex-6-ylbut-1-yn-3-ol;
(S)-4-exo-bicyclo[3.1.0]hex-6-ylbut-1-yn-3-ol;
(S)-3-cyclopentyl-3-methylprop-1-yn-3-ol;
(S)-3-cyclobutyl-3-methylprop-1-yn-3-ol;
(S)-3-cyclooctylprop-1-yn-3-ol;
(S)-4-cyclopentylbut-1-yn-3-ol;
(S)-3-cyclopentylprop-1-yn-3-ol; and
(S)-4-cyclohexylbut-1-yn-3-ol.

PREPARATION 11

Preparation of (S)-3-Tert-butyldimethylsilyloxyoct-1-yne and Related Silyl Ethers of Formula (XX)

A. To a solution of (S)-3-cyclohexylprop-1-yn-3-ol, (obtained according to Preparation 10) (2.76 g, 0.02 mol), in 10 ml N,N-dimethylformamide (DMF), cooled to 0° C., was added imidazole (2.1 g), followed by tert-butyldimethylchlorosilane (3.1 g, 0.02 mol). The mixture was stirred for 3 h. Water (80 ml) and hexane (80 ml) were added; the organic layer was separated and combined with 2×80 ml of hexane extractions of the aqueous layer. The solvent was removed (in vacuo), after drying over sodium sulfate, to give a crude residue (4.3 g) which was chromatographed on silica gel (80 g), eluting with ethyl acetate-hexane (2:1, v/v) to afford (S)-3-tert-butyldimethylsilyloxy-3-cyclohexylprop-1-yne.

B. In like manner, but replacing the (S)-3-cyclohexylprop-1-yn-3-ol with (S)-oct-1-yn-3-ol, prepared according to Preparation 10, there was prepared (S)-3-t-butyldimethylsilyloxyoct-1-yne.

C. Similarly, following the procedures of 11.A. above, but starting instead with other suitable compounds of formula (XIX), prepared according to Preparation 9 or 10, the following representative compounds of formula (XX) are prepared:
(S)-3-t-butyldimethylsilyloxydec-1-yne;
(S)-3-t-butyldimethylsilyloxytridec-1-yne;
(3S,5R)-3-t-butyldimethylsilyloxy-5-methylnon-1-yne;

(S)-3-t-butyldimethylsilyloxynon-1-yne;
(S)-3-t-butyldimethylsilyloxy-4-phenylbut-1-yne;
(S)-3-t-butyldimethylsilyloxy-5-phenylpent-1-yne;
(S)-3-t-butyldimethylsilyloxy-4-m-trifluoromethylphenylbut-1-yne;
(S)-3-t-butyldimethylsilyloxy-4-endo-bicyclo[3.1.0]hex-6-ylbut-1-yne;
(S)-3-t-butyldimethylsilyloxy-4-exo-bicyclo[3.1.0]hex-6-ylbut-1-yne;
(S)-3-t-butyldimethylsilyloxy-3-cyclopentylprop-1-yne;
(S)-3-t-butyldimethylsilyloxy-3-cyclooctylprop-1-yne;
(S)-3-t-butyldimethylsilyloxy-4-cyclopentylbut-1-yne;
(S)-3-t-butyldimethylsilyloxy-4-cyclohexylbut-1-yne, and
3-t-butyldimethylsilyloxy-4-phenoxybut-1-yne.

D. Similarly, but starting instead with racemic compounds of formula (XVII), prepared according to Preparation 7, the following exemplary racemic compounds of formula (XX) are prepared:
3-t-butyldimethylsilyloxyoct-1-yne;
3-t-butyldimethylsilyloxydec-1-yne;
3-t-butyldimethylsilyloxytridec-1-yne;
3-t-butyldimethylsilyloxynon-1-yne;
3-t-butyldimethylsilyloxy-4-phenylbut-1-yne;
3-t-butyldimethylsilyloxy-5-phenylpent-1-yne;
3-t-butyldimethylsilyloxy-4-m-trifluoromethylphenylbut-1-yne;
3-t-butyldimethylsilyloxy-4-endo-bicyclo[3.1.0]hex-6-ylbut-1-yne;
3-t-butyldimethylsilyloxy-4-exo-bicyclo[3.1.0]hex-6-ylbut-1-yne;
3-t-butyldimethylsilyloxy-3-cyclopentylprop-1-yne;
3-t-butyldimethylsilyloxy-3-cyclohexylprop-1-yne;
3-t-butyldimethylsilyloxy-3-cyclooctylprop-1-yne;
3-t-butyldimethylsilyloxy-4-cyclopentylbut-1-yne;
3-t-butyldimethylsilyloxy-4-cyclohexylbut-1-yne;
3-t-butyldimethylsilyloxy-3-methyl-3-cyclobutylprop-1-yne; and
3-t-butyldimethylsilyloxy-3-methyl-3-cyclopentylprop-1-yne.

PREPARATION 12

Preparation of the mixture of (3'S,1R,2S,3R,6R)-Spiro[2-(3'-t-butyldimethylsilyloxy-3'-cyclohexylprop-1'-ynyl)-3-hydroxy-6-methoxybicyclo[4.2.0]octane-7,2''-(1'',3''-dioxolane)](VIII), (3'S,1S,2R,3S,6S)-Spiro[2-(3'-t-butyldimethylsilyloxy-3'-cyclohexylprop-1'-ynyl)-3-hydroxy-6-methoxybicyclo[4.2.0]octane-7,2''-(1'',3''-dioxolane)] (IX) and Related Compounds of Formula (VIII) and (IX)

A. To a mixture of 7.56 g of (S)-3-t-butyldimethylsilyloxy-3-cyclohexylprop-1-yne prepared according to Preparation 11 in 40 ml tetrahydrofuran at 0° C. under an argon atmosphere was added over 10 min 18 ml of 1.55M n-butylithium in hexane. The resulting solution was cooled to −78° C. and a solution of 5.6 g of a mixture of (1RS,2SR,3RS,6RS)-spiro[2,3-epoxy-6-methoxybicyclo[4.2.0]octane-7,2''-(1'',3''-dioxolane)] and (1RS,2RS,3SR,6RS)-spiro-[2,3-epoxy-6-methoxybicyclo[4.2.0]octane-7,2''-(1'',3''-dioxolane)] in 25 ml tetrahydrofuran was added. To this stirred mixture at −78° C. was added 3.2 ml of boron trifluoride etherate dropwise over a 15 minute period, followed by 25 ml of saturated sodium sulfate solution. The resulting mixture was warmed to room temperature and extracted thoroughly with ethyl acetate. This extract was dried over sodium sulfate and concentrated in vacuo to give an oily residue. Volatiles were removed on a Kugelrohr distillation device at 95° C. (0.1 mm Hg) to leave 9.28 g of a residue, which was further purified by flash chromatography on silica gel using hexane-ethyl acetate (4:1). This procedure gave 5.6 g of a mixture of the title compounds as an oil.

B. In like manner, following the procedure of paragraph 12.A. above, but replacing the mixture of epoxides with other mixtures of compounds of formula (VI) and (VII), the following mixtures of compounds of formula (VIII) and (IX) were prepared:
(3'S,1R,2R,3R,6R)- and (3'S,1S,2R,3S,6S)-spiro[2-(3'-t-butyldimethylsilyloxy-3'-cyclohexylprop-1'-ynyl)-3-hydroxy-6-(2,2,2-trifluoroethoxy)bicyclo[4.2.0]octane-7,2''-(1'',3''-dioxolane)];
(3'S,1S,2S,3R,6R)- and (3'S,1R,2R,3S,6S)-spiro[2-(3'-t-butyldimethylsilyloxy-3'-cyclohexylprop-1'-ynyl)-3-hydroxy-6-methoxy-8-exo-methylbicyclo[4.2.0]octane-7,2''-(1'',3''-dioxolane)]; and
(3'S,1S,2S,3R,6R)- and (3'S,1R,2R,3S,6S)-spiro[2-(3'-t-butyldimethylsilyloxy-3'-cyclohexylprop-1'-ynyl)-3-hydroxy-6-methoxy-8-endo-methylbicyclo[4.2.0]octane-7,2''-(1'',3''-dioxolane)].

C. In like manner, following the procedure of paragraph 12.A. above, but replacing the the mixture of epoxides with mixtures of compounds of formula (VIA) and (VIIA), prepared as shown in Preparations 5.C. and 6.B., the following exemplary of compounds of formula (VIIIA) and (IXA) are prepared:
(3'S,1R,2S,3R,6R)-Spiro[2-(3'-t-butyldimethylsilyloxy-3'-cyclohexylprop-1'-ynyl)-3-hydroxy-6-methoxybicyclo[4.2.0]octane-7,2''-(1'',3''-dioxolane)];
(3'S,1S,2R,3S,6S)-Spiro[2-(3'-t-butyldimethylsilyloxy-3'-cyclohexylprop-1'-ynyl)-3-hydroxy-6-methoxybicyclo[4.2.0]octane-7,2''-(1'',3''-dioxolane)];
(3'S,1S,2S,3R,6R)-Spiro[2-(3'-t-butyldimethylsilyloxy-3'-cyclohexylprop-1'-ynyl)-3-hydroxy-6-methoxy-8-exo-methylbicyclo[4.2.0]octane-7,2''-(1'',3''-dioxolane)];
(3'S,1R,2R,3S,6S)-Spiro[2-(3'-t-butyldimethylsilyloxy-3'-cyclohexylprop-1'-ynyl)-3-hydroxy-6-methoxy-8-exo-methylbicyclo[4.2.0]octane-7,2''-(1'',3''-dioxolane)];
(3'S,1S,2S,3R,6R)-Spiro[2-(3'-t-butyldimethylsilyloxy-3'-cyclohexyl-prop-1'-ynyl)-3-hydroxy-6-methoxy-8-endo-methylbicyclo[4.2.0]octane-7,2''-(1'',3''-dioxolane)];
(3'S,1R,2R,3S,6S)-Spiro[2-(3'-t-butyldimethylsilyloxy-3'-cyclohexylprop-1'-ynyl)-3-hydroxy-6-methoxy-8-endo-methylbicyclo[4.2.0]octane-7,2''-(1'',3''-dioxolane)];

D. In like manner, following the procedures of paragraph 12.A. above, the following representative mixtures of compounds of formulas (VIII) and (IX), where Y is H, or exo or endo-(lower alkyl), are prepared:
(3'S,1R,2S,3R,6R)- and (3'S,1S,2R,3S,6S)-spiro[2-(3'-t-butyldimethylsilyloxy-3'-cyclohexylprop-1'-ynyl)-3-hydroxy-6-ethoxybicyclo[4.2.0]octane-7,2''-(1'',3''-dioxolane)];
(3'S,1R,2S,3R,6R)- and (3'S,1S,2R,3S,6S)-spiro[2-(3'-t-butyldimethylsilyloxy-3'-cyclohexylprop-1'-ynyl)-3-hydroxy-6-n-butoxybicyclo[4.2.0]octane-7,2''-(1'',3''-dioxolane)];
(3'S,1S,2S,3R,6R)- and (3'S,1R,2R,3S,6S)-spiro[2-(3'-t-butyldimethylsilyloxy-3'-cyclohexylprop-1'-ynyl)-3-hydroxy-6-ethoxy-8-methylbicyclo[4.2.0]octane-7,2''-(1'',3''-dioxolane)];

(3'S,1S,2S,3R,6R)- and (3'S,1R,2R,3S,6S)-spiro[2-(3'-t-butyldimethylsilyloxy-4'-(endo-bicyclo[3.1.0]hex-6-yl)but-1'-ynyl)-3-hydroxy-6-methoxybicyclo[4.2.0]octane-7,2''-(1'',3''-dioxolane)];

(3'S,1R,2S,3R,6R)- and (3'S,1S,2R,3S,6S)-spiro[2-(3'-t-butyldimethylsilyloxy-4'-cyclopentylbut-1'-ynyl)-3-hydroxy-6-methoxybicyclo[4.2.0]octane-7,2''-(1'',3''-dioxolane)];

(3'S,1R,2S,3R,6R)- and (3'S,1S,2R,3S,6S)-spiro[2-(3'-t-butyldimethylsilyloxy-4'-cyclohexylbut-1'-ynyl)-3-hydroxy-6-methoxybicyclo[4.2.0]octane-7,2''-(1'',3''-dioxolane)];

(3'S,1R,2S,3R,6R)- and (3'S,1S,2R,3S,6S)-spiro[2-(3'-t-butyldimethylsilyloxy-3'-dec-1'-ynyl)-3-hydroxy-6-methoxybicyclo[4.2.0]octane-7,2''-(1'',3''-dioxolane)];

(3'S,1S,2S,3R,6R)- and (3'S,1R,2R,3S,6S)-spiro[2-(3'-t-butyldimethylsilyloxy-3'-cyclohexylprop-1'-ynyl)-3-hydroxy-6-methoxy-8-ethylbicyclo[4.2.0]octane-7,2''-(1'',3''-dioxolane)];

(3'S,1S,2S,3R,6R)- and (3'S,1R,2R,3S,6S)-spiro[2-(3'-t-butyldimethylsilyloxy-3'-cyclohexylprop-1'-ynyl)-3-hydroxy-6-methoxy-8-n-butylbicyclo[4.2.0]octane-7,2''-(1'',3''-dioxolane)];

(3'S,1S,2S,3R,6R)- and (3'S,1R,2R,3S,6S)-spiro[2-(3'-t-butyldimethylsilyloxy-3'-cyclohexylprop-1'-ynyl)-3-hydroxy-6-butoxy-8-n-butylbicyclo[4.2.0]octane-7,2''-(1'',3''-dioxolane)];

(3'R,1R,2S,3R,6R)- and (3'S,1S,2R,3S,6S)-spiro[2-(3'-t-butyldimethylsilyloxy-4'-phenoxybut-1'-ynyl)-3-hydroxy-6-methoxybicyclo[4.2.0]octane-7,2''-(1'',3''-dioxolane)];

(3'R,1S,2S,3R,6R)- and (3'S,1R,2R,3S,6S)-spiro[2-(3'-t-butyldimethylsilyloxy-4'-phenoxybut-1'-ynyl)-3-hydroxy-6-methoxy-8-methylbicyclo[4.2.0]octane-7,2''-(1'',3''-dioxolane)];

PREPARATION 13

Preparation of (3'S,1R,2S,3R,6R)-Spiro[2-(3'-t-butyldimethylsilyloxy-3'-cyclohexylprop-1'-ynyl)-3-hydroxy-6-methoxybicyclo[4.2.0]octane-7,2''-(1'',3''-dioxolane)] and (3'S,1S,2R,3S,6S)-Spiro[2-(3'-t-butyldimethylsilyloxy-3'-cyclohexylprop-1'-ynyl)-3-hydroxy-6-methoxybicyclo[4.2.0]octane-7,2''-(1'',3''-dioxolane)] and Related Compounds of Formulas (XII) and (XIII)

A. To a mixture of 5.6 g of the diastereomeric mixture of the above title compounds obtained as described in Preparation 12, in 200 ml diethyl ether was added 5.0 g of dicobalt octacarbonyl. The resulting solution was stirred at 23° C. for 1 hour. The mixture was diluted with 200 ml of diethyl ether and the resulting solution was filtered through 100 g of silica gel. The filtrate was concentrated to an oil which was purified by flash chromatography using 13% ethyl acetate-hexane to give two components: A (high $R_f$) and B (low $R_f$). Component A (4.0 g) was dissolved in 200 ml acetone-water (9:1), to which was added 14 g ceric ammonium nitrate. After 2 min. this mixture was diluted with 300 ml water. The product was isolated by extraction with diethyl ether. After drying and evaporation there was obtained 2.1 g of (3'S,1R,2S,3R,6R)-Spiro[2-(3'-t-butyldimethylsilyloxy-3'-cyclohexylprop-1'-ynyl)-3-hydroxy-6-methoxybicyclo[4.2.0]octane-7,2''-(1'',3''-dioxolane)] as an oil. Similarly component B (4.0 g) was converted to 2.2 g of (3'S,1S,2R,3S,6S)-Spiro[2-(3'-t-butyldimethylsilyloxy-3'-cyclohexylprop-1'-ynyl)-3-hydroxy-6-methoxybicyclo[4.2.0]octane-7,2''-(1'',3''-dioxolane)] as an oil.

B. In like manner, following the procedures of paaragraph 13.A. above, but starting instead with other diastereomeric mixtures of compounds (VIII) and (IX), the following individual optical isomers (XII) and (XIII) were obtained:

(3'S,1R,2S,3R,6R)-spiro[2-(3'-t-butyldimethylsilyloxy-3-cyclohexylprop-1'-ynyl)-3-hydroxy-6-(2,2,2-trifluoroethoxy)bicyclo[4.2.0]octane-7,2''-(1'',3''-dioxolane)];

(3'S,1S,2R,3S,6S)-spiro[2-(3'-t-butyldimethylsilyloxy-3-cyclohexylprop-1'-ynyl)-3-hydroxy-6-(2,2,2-trifluoroethoxy)bicyclo[4.2.0]octane-7,2''-(1'',3''-dioxolane)];

(3'S,1S,2S,3R,6R)-spiro[2-(3'-t-butyldimethylsilyloxy-3-cyclohexylprop-1'-ynyl)-3-hydroxy-6-methoxy-8-exo-methylbicyclo[4.2.0]octane-7,2''-(1'',3''-dioxolane)];

(3'S,1R,2R,3S,6S)-spiro[2-(3'-t-butyldimethylsilyloxy-3-cyclohexylprop-1'-ynyl)-3-hydroxy-6-methoxy-8-exo-methylbicyclo[4.2.0]octane-7,2''-(1'',3''-dioxolane)];

(3'S,1S,2S,3R,6R)-spiro[2-(3'-t-butyldimethylsilyloxy-3-cyclohexylprop-1'-ynyl)-3-hydroxy-6-methoxy-8-endo-methylbicyclo[4.2.0]octane-7,2''-(1'',3''-dioxolane)];

(3'S,1R,2R,3S,6S)-spiro[2-(3'-t-butyldimethylsilyloxy-3-cyclohexylprop-1'-ynyl)-3-hydroxy-6-methoxy-8-endo-methylbicyclo[4.2.0]octane-7,2''-(1'',3''-dioxolane)];

C. In like manner, following the procedures of paragraph 13.A. above, the following exemplary individual optical isomers of formula (XII) and (XIII) are obtained:

(3'S,1R,2S,3R,6R)-spiro[2-(3'-t-butyldimethylsilyloxy-3'-cyclohexylprop-1'-ynyl)-3-hydroxy-6-ethoxybicyclo[4.2.0]octane-7,2''-(1'',3''-dioxolane)];

(3'S,1S,2R,3S,6S)-spiro[2-(3'-t-butyldimethylsilyloxy-3'-cyclohexylprop-1'-ynyl)-3-hydroxy-6-ethoxybicyclo[4.2.0]octane-7,2''-(1'',3''-dioxolane)];

(3'R,1R,2S,3R,6R)-spiro[2-(3'-t-butyldimethylsilyloxy-4'-phenoxybut-1'-ynyl)-3-hydroxy-6-methoxybicyclo[4.2.0]octane-7,2''-(1'',3''-dioxolane)];

(3'R,1S,2R,3S,6S)-spiro[2-(3'-t-butyldimethylsilyloxy-4'-phenoxybut-1'-ynyl)-3-hydroxy-6-methoxybicyclo[4.2.0]octane-7,2''-(1'',3''-dioxolane)];

(3'S,1R,2S,3R,6R)-spiro[2-(3'-t-butyldimethylsilyloxy-4'-(exo-bicyclo[3.1.0]hex-6-yl)but-1'-ynyl)-3-hydroxy-6-methoxybicyclo[4.2.0]octane-7,2''-(1'',3''-dioxolane)];

(3'S,1S,2R,3S,6S)-spiro[2-(3'-t-butyldimethylsilyloxy-4'-(exo-bicyclo[3.1.0]hex-6-yl)but-1'-ynyl)-3-hydroxy-6-methoxybicyclo[4.2.0]octane-7,2''-(1'',3''-dioxolane)];

(3'R,1S,2S,3R,6R)-spiro[2-(3'-t-butyldimethylsilyloxy-4'-phenoxybut-1'-ynyl)-3-hydroxy-6-methoxy-8-endo-methylbicyclo-[4.2.0]octane-7,2''-(1'',3''-dioxolane)];

(3'R,1R,2R,3S,6S)-spiro[2-(3'-t-butyldimethylsilyloxy-4'-phenoxybut-1'-ynyl)-3-hydroxy-6-methoxy-8-endo-methylbicyclo-[4.2.0]octane-7,2''-(1'',3''-dioxolane)];

(3'S,1R,2S,3R,6R)-spiro[2-(3'-t-butyldimethylsilyloxy-3'-cyclohexylprop-1'-ynyl)-3-hydroxy-6-n-butoxybicyclo[4.2.0]octane-7,2''-(1'',3''-dioxolane)];

(3'S,1S,2R,3S,6S)-spiro[2-(3'-t-butyldimethylsilyloxy-3'-cyclohexylprop-1'-ynyl)-3-hydroxy-6-n-butoxybicyclo[4.2.0]octane-7,2"-(1",3"-dioxolane)];

(3'S,1S,2S,3R,6R)-spiro[2-(3'-t-butyldimethylsilyloxy-3'-cyclohexylprop-1'-ynyl)-3-hydroxy-6-ethoxy-8-exo-methylbicyclo[4.2.0]octane-7,2"-(1",3"-dioxolane)];

(3'S,1R,2R,3S,6S)-spiro[2-(3'-t-butyldimethylsilyloxy-3'-cyclohexylprop-1'-ynyl)-3-hydroxy-6-ethoxy-8-exo-methylbicyclo[4.2.0]octane-7,2"-(1",3"-dioxolane)];

(3'S,1S,2S,3R,6R)-spiro[2-(3'-t-butyldimethylsilyloxy-3'-cyclohexylprop-1'-ynyl)-3-hydroxy-6-(2,2,2-trifluoroethoxy)-8-endo-methylbicyclo[4.2.0]octane-7,2"-(1",3"-dioxolane)];

(3'S,1R,2R,3S,6S)-spiro[2-(3'-t-butyldimethylsilyloxy-3'-cyclohexylprop-1'-ynyl)-3-hydroxy-6-(2,2,2-trifluoroethoxy)-8-endo-methylbicyclo[4.2.0]octane-7,2"-(1",3"-dioxolane)];

(3'S,1R,2S,3R,6R)-spiro[2-(3'-t-butyldimethylsilyloxy-3'-cyclopentylbut-1'-ynyl)-3-hydroxy-6-methoxybicyclo[4.2.0]octane-7,2"-(1",3"-dioxolane)];

(3'S,1S,2R,3S,6S)-spiro[2-(3'-t-butyldimethylsilyloxy-3'-cyclopentylbut-1'-ynyl)-3-hydroxy-6-methoxybicyclo[4.2.0]octane-7,2"-(1",3"-dioxolane)];

(3'S,1R,2S,3R,6R)-spiro[2-(3'-t-butyldimethylsilyloxy-3'-cyclohexylbut-1'-ynyl)-3-hydroxy-6-methoxybicyclo[4.2.0]octane-7,2"-(1",3"-dioxolane)];

(3'S,1S,2R,3S,6S)-spiro[2-(3'-t-butyldimethylsilyloxy-3'-cyclohexylbut-1'-ynyl)-3-hydroxy-6-methoxybicyclo[4.2.0]octane-7,2"-(1",3"-dioxolane)];

(3'S,1R,2S,3R,6R)-spiro[2-(3'-butyldimethylsilyloxy-3'-dec-1'-ynyl)-3-hydroxy-6-methoxybicyclo[4.2.0]octane-7,2"(1",3"-dioxolane)];

(3'S,1S,2R,3S,6S)-spiro[2-(3'-t-butyldimethylsilyloxy-3'-dec-1'-ynyl)-3-hydroxy-6-methoxybicyclo[4.2.0]octane-7,2"-(1",3"-dioxolane)];

(3'S,1S,2S,3R,6R)-spiro[2-(3'-t-butyldimethylsilyoxy-3'-cyclohexylprop-1'-ynyl)-3-hydroxy-6-methoxy-8-endo-ethylbicyclo[4.2.0]octane-7,2"-(1",3"-dioxolane)];

(3'S,1R,2R,3S,6S)-spiro[2-(3'-t-butyldimethylsilyloxy-3'-cyclohexylprop-1'-ynyl)-3-hydroxy-6-methoxy-8-endo-ethylbicyclo[4.2.0]octane-7,2"-(1",3"-dioxolane)];

(3'S,1S,2S,3R,6R)-spiro[2-(3'-t-butyldimethylsilyloxy-3'-cyclohexylprop-1'-ynyl)-3-hydroxy-6-methoxy-8-exo-n-butylbicyclo[4.2.0]octane-7,2"-(1",3"-dioxolane)];

(3'S,1R,2R,3S,6S)-spiro[2-(3'-t-butyldimethylsilyloxy-3'-cyclohexylprop-1'-ynyl)-3-hydroxy-6-methoxy-8-exo-n-butylbicyclo[4.2.0]octane-7,2"-(1",3"-dioxolane)];

(3'S,1S,2S,3R,6R)-spiro[2-(3'-t-butyldimethylsilyloxy-3'-cyclohexylprop-1'-ynyl)-3-hydroxy-6-n-butoxy-8-endo-n-butylbicyclo[4.2.0]-octane-7,2"-(1",3"-dioxolane)];

(3'S,1R,2R,3S,6S)-spiro[2-(3'-t-butyldimethylsilyloxy-3'-cyclohexylprop-1'-ynyl)-3-hydroxy-6-n-butoxy-8-endo-n-butylbicyclo[4.2.0]octane-7,2"-(1",3"-dioxolane)];

PREPARATION 14

Preparation of (3'S,1R,2S,3R,6R)-2-(3'-hydroxy-3'-cyclohexylprop-1'-ynyl)-3-hydroxy-6-methoxybicyclo[4.2.0]octan-7-one and Related Compounds of Formulas (XIV) and (XV)

A. A solution of 2.1 g of (3'S,1R,2S,3R,6R)-spiro[2-(3'-t-butyldimethylsilyloxy-3'-cyclohexylprop-1'-ynyl)-3-hydroxy-6-methoxybicyclo[4.2.0]octane-7,2"-(1",3"-dioxolane)], prepared as shown in Preparation 12 or 13 in 30 ml of acetonitrile and 20 ml of 2.4N sulfuric acid was stirred at 50° C. for 16 hours. The reaction was quenched by neutralization with aqueous sodium bicarbonate and the mixture was extracted with diethyl ether. The extracts were dried with magnesium sulfate, evaporated to dryness and the residue was purified by short column silica-gel chromatography. Elution with ethyl acetate-hexane (1:1), gave 1.05 g of (3'S,1R,2S,3R,6R)-2-(3'-hydroxy-3'-cyclohexylprop-1'-ynyl)-3-hydroxy-6-methoxybicyclo[4.2.0]octan-7-one.

B. In like manner, following the procedure of paragraph 14.A. above, but starting with other appropriate compounds of formula (XII) or (XIII) the following compounds of formula (XIV) or (XV) were obtained:

(3'S,1S,2R,3S,6S)-2-(3'-hydroxy-3'-cyclohexylprop-1'-ynyl)-3-hydroxy-6-methoxybicyclo[4.2.0]octan-7-one.

(3'S,1R,2S,3R,6R)-[2-(3'-hydroxy-3'-cyclohexylprop-1'-ynyl)-3-hydroxy-6-(2,2,2-trifluoroethoxy)bicyclo[4.2.0]octan-7-one;

(3'S,1S,2R,3S,6S)-[2-(3'-hydroxy-3'-cyclohexylprop-1'-ynyl)-3-hydroxy-6-(2,2,2-trifluoroethoxy)bicyclo[4.2.0]octan-7-one;

(3'S,1S,2S,3R,6R)-[2-(3'-hydroxy-3'-cyclohexylprop-1'-ynyl)-3-hydroxy-6-methoxy-8-exo-methylbicyclo[4.2.0]octan-7-one;

(3'S,1R,2R,3S,6S)-[2-(3'-hydroxy-3'-cyclohexylprop-1'-ynyl)-3-hydroxy-6-methoxy-8-exo-methylbicyclo[4.2.0]octan-7-one;

(3'S,1S,2S,3R,6R)-[2-(3'-hydroxy-3'-cyclohexylprop-1'-ynyl)-3-hydroxy-6-methoxy-8-endo-methylbicyclo[4.2.0]octan-7-one;

(3'S,1R,2R,3S,6S)-[2-(3'-hydroxy-3'-cyclohexylprop-1'-ynyl)-3-hydroxy-6-methoxy-8-endo-methylbicyclo[4.2.0]octan-7-one;

C. In like manner, following the procedures of paragraph 14.A. above, the following exemplary compounds of formula (XIV) or (XV), where Y is H, or exo or endo-(lower alkyl), are obtained:

(3'S,1R,2S,3R,6R)-[2-(3'-hydroxy-3'-cyclohexylprop-1'-ynyl)-3-hydroxy-6-ethoxybicyclo[4.2.0]octan-7-one;

(3'S,1S,2R,3S,6S)-[2-(3'-hydroxy-3'-cyclohexylprop-1'-ynyl)-3-hydroxy-6-ethoxybicyclo[4.2.0]octan-7-one;

(3'R,1R,2S,3R,6R)-2-(3'-hydroxy-4'-phenoxybut-1'-ynyl)-3-hydroxy-6-methoxybicyclo[4.2.0]octan-7-one.

(3'R,1S,2R,3S,6S)-2-(3'-hydroxy-4'-phenoxybut-1'-ynyl)-3-hydroxy-6-methoxybicyclo[4.2.0]octan-7one.

(3'R,1S,2S,3R,6R)-2-(3'-hydroxy-4'-phenoxybut-1'-ynyl)-3-hydroxy-6-methoxy-8-methylbicyclo[4.2.0]octan-7-one;

(3'R,1R,2R,3S,6S)-2-(3'-hydroxy-4'-phenoxybut-1'-ynyl)-3-hydroxy-6-methoxy-8-methylbicyclo[4.2.0]octan-7-one;

(3'S,1R,2S,3R,6R)-[2-(3'-hydroxy-3'-cyclohexylprop-1'-ynyl)-3-hydroxy-6-n-butoxybicyclo[4.2.0]octan-7-one;

(3'S,1S,2R,3S,6S)-[2-(3'-hydroxy-3'-cyclohexylprop-1'-ynyl)-3-hydroxy-6-n-butoxybicyclo[4.2.0]octan-7-one;

(3'S,1S,2S,3R,6R)-[2-(3'-hydroxy-3'-cyclohexylprop-1'-ynyl)-3-hydroxy-6-ethoxy-8-methylbicyclo[4.2.0]-octan-7-one;

(3'S,1R,2R,3S,6S)-[2-(3'-hydroxy-3'-cyclohexylprop-1'-ynyl)-3-hydroxy-6-ethoxy-8-methylbicyclo[4.2.0]octan-7-one;

(3'S,1R,2S,3R,6R)-[2-(3'-hydroxy-4'-(exo-bicyclo[3.1.0]hex-6-yl)but-1'-ynyl)-3-hydroxy-6-methoxybicyclo[4.2.0]octan-7-one;

(3'S,1S,2R,3S,6S)-[2-(3'-hydroxy-4'-(exo-bicyclo[3.1.0]hex-6-yl)but-1'-ynyl)-3-hydroxy-6-methoxybicyclo[4.2.0]octan-7-one;

(3'S,1R,2S,3R,6R)-[2-(3'-hydroxy-3'-cyclopentylbut-1'-ynyl)-3-hydroxy-6-methoxybicyclo[4.2.0]-octan-7-one;

(3'S,1S,2R,3S,6S)-[2-(3'-hydroxy-3'-cyclopentylbut-1'-ynyl)-3-hydroxy-6-methoxybicyclo[4.2.0]octan-7-one;

(3'S,1R,2S,3R,6R)-[2-(3'-hydroxy-3'-cyclohexylbut-1'-ynyl)-3-hydroxy-6-methoxybicyclo[4.2.0]octan-7-one;

(3'S,1S,2R,3S,6S)-[2-(3'-hydroxy-3'-cyclohexylbut-1'-ynyl)-3-hydroxy-6-methoxybicyclo[4.2.0]octan-7-one;

(3'S,1R,2S,3R,6R)-[2-(3'-hydroxy-3'-dec-1'-ynyl)-3-hydroxy-6-methoxybicyclo[4.2.0]octan-7-one;

(3'-S,1S,2R,3S,6S)-[2-(3'-hydroxy-3'-dec-1'-ynyl)-3-hydroxy-6-methoxybicyclo[4.2.0]octan-7-one;

(3'S,1S,2S,3R,6R)-2-(3'-hydroxy-3'-cyclohexylprop-1'-ynyl)-3-hydroxy-6-methoxy-8-ethylbicyclo[4.2.0]octan-7-one;

(3'S,1R,2R,3S,6S)-2-(3'-hydroxy-3'-cyclohexylprop-1'-ynyl)-3-hydroxy-6-methoxy-8-ethylbicyclo[4.2.0]octan-7-one;

(3'S,1S,2S,3R,6R)-2-(3'-hydroxy-3'-cyclohexylprop-1'-ynyl)-3-hydroxy-6-methoxy-8-n-butylbicyclo[4.2.0]octan-7-one;

(3'S,1R,2R,3S,6S)-2-(3'-hydroxy-3'-cyclohexylprop-1'-ynyl)-3-hydroxy-6-methoxy-8-n-butylbicyclo[4.2.0]octan-7-one;

(3'S,1S,2S,3R,6R)-2-(3'-hydroxy-3'-cyclohexylprop-1'-ynyl)-3-hydroxy-6-n-butoxy-8-n-butylbicyclo[4.2.0]octan-7-one; and (3'S,1R,2R,3S,6S)-2-(3'-hydroxy-3'-cyclohexylprop-1'-ynyl)-3-hydroxy-6-n-butoxy-8-n-butylbicyclo[4.2.0]octan-7-one.

PREPARATION 15

A. Preparation of (3'S,1S,2R,3S,6S)-spiro[2-(3'-hydroxy-3'-cyclohexylprop-1'-ynyl)-3-hydroxy-6-methoxybicyclo[4.2.0]octane-7,2''-(1'',3''-dioxolane)] and related compounds of formula (LIV)

To a solution of 4.7 g of (3'S,1S,2R,3S,6S)-spiro[2-(3'-t-butyldimethylsilyloxy-3'-cyclohexylprop-1'-ynyl)-3-hydroxy-6-methoxybicyclo[4.2.0]octane-7,2''-(1'',3''-dixolane)], prepared as shown in Preparation 13, in 60 ml of tetrahydrofuran at 23° C. was added 25 ml of 1M tetrabutylammonium fluoride in tetrahydrofuran. The solution was stirred at room temperature for 5 hours, then 200 ml of water and 50 ml of saturated aqueous sodium bicarbonate was added. The mixture was extracted with ethyl acetate, the organic layer dried over sodium sulfate and the solvent removed under reduced pressure. The residue was chromatographed on silica gel, eluting with hexane-ethyl acetate mixture (3:2), giving 3.25 g of (3'S,1S,2R,3S,6S)-spiro[2-(3'-hydroxy-3'-cyclohexylprop-1'-ynyl)-3-hydroxy-6-methoxybicyclo[4.2.0]octane-7,2''-(1'',3''-dioxolane)].

B. In like manner, following the procedure of paragraph 15.A. above but starting with the appropriate compounds of formula (XII) or (XIII), the following exemplary compounds of formula (LIV) are prepared:

(3'S,1R,2S,3R,6R)-spiro[2-(3'-hydroxy-3'-cyclohexylprop-1'-ynyl)-3-hydroxy-6-methoxybicyclo[4.2.0]octane-7,2''-(1'',3''-dioxolane)].

(3'R,1R,2S,3R,6R)-spiro[2-(3'-hydroxy-4'-phenoxybut-1'-ynyl)-3-hydroxy-6-methoxybicyclo[4.2.0]octane-7,2''-(1'',3''-dioxolane)].

(3'R,1S,2R,3S,6S)-spiro[2-(3'-hydroxy-4'-phenoxybut-1'-ynyl)-3-hydroxy-6-methoxybicyclo[4.2.0]octane-7,2''-(1'',3''-dioxolane)].

(3'R,1S,2S,3R,6R)-spiro[2-(3'-hydroxy-4'-phenoxybut-1'-ynyl)-3-hydroxy-6-methoxy-8-endo-methylbicyclo[4.2.0]octane-7,2''-(1'',3''-dioxolane)].

(3'R,1R,2R,3S,6S)-spiro[2-(3'-hydroxy-4'-phenoxybut-1'-ynyl)-3-hydroxy-6-methoxy-8-endo-methylbicyclo[4.2.0]octane-7,2''-(1'',3''-dioxolane)].

(3'S,1R,2S,3R,6R)-spiro[2-(3'-hydroxy-4'-(exo-bicyclo[3.1.0]hex-6-yl)but-1'-ynyl)-3-hydroxy-6-methoxybicyclo[4.2.0]octane-7,2''-(1'',3''-dioxolane)];

(3'S,1S,2R,3S,6S)-spiro[2-(3'-hydroxy-4'-(exo-bicyclo[3.1.0]hex-6-yl)but-1'-ynyl)-3-hydroxy-6-methoxybicyclo[4.2.0]octane-7,2''-(1'',3''-dioxolane)];

(3'S,1R,2S,3R,6R)-spiro[2-(3'-hydroxy-3-cyclohexylprop-1'-ynyl)-3-hydroxy-6-(2,2,2-trifluoroethoxy)-bicyclo[4.2.0]octane-7,2''-(1'', 3''-dioxolane)];

(3'S,1S,2R,3S,6S)-spiro[2-(3'hydroxy-3-cyclohexylprop-1'-ynyl)-3-hydroxy-6-(2,2,2-trifluoroethoxy)-bicyclo[4.2.0]octane-7,2''-(1'',3''-dioxolane)];

(3'S,1S,2S,3R,6R)-spiro[2-(3'-hydroxy-3-cyclohexylprop-1'-ynyl)-3-hydroxy-6-methoxy-8-exo-methylbicyclo[4.2.0]octane-7,2''-(1'',3''-dioxolane)];

(3'S,1R,2R,3S,6S)-spiro[2-(3'-hydroxy-3-cyclohexylprop-1'-ynyl)-3-hydroxy-6-methoxy-8-exo-methylbicyclo[4.2.0]octane-7,2''-(1'',3''-dioxolane)];

(3'S,1S,2S,3R,6R)-spiro[2-(3'-hydroxy-3-cyclohexylprop-1'-ynyl)-3-hydroxy-6-methoxy-8-endo-methylbicyclo[4.2.0]octane-7,2''-(1'',3''-dioxolane)];

(3'S,1R,2R,3S,6S)-spiro[2-(3'-hydroxy-3-cyclohexylprop-1'-ynyl)-3-hydroxy-6-methoxy-8-endo-methylbicyclo[4.2.0]octane-7,2''-(1'',3''-dioxolane)];

(3'S,1R,2S,3R,6R)-spiro[2-(3'-hydroxy-3'-cyclohexylprop-1'-ynyl)-3-hydroxy-6-ethoxybicyclo[4.2.0]octane-7,2''-(1'',3''-dioxolane)];

(3'S,1S,2R,3S,6S)-spiro[2-(3'-hydroxy-3'-cyclohexylprop-1'-ynyl)-3-hydroxy-6-ethoxybicyclo[4.2.0]octane-7,2''-(1'',3''-dioxolane)];

(3'S,1R,2S,3R,6R)-spiro[2-(3'-hydroxy-3'-cyclohexylprop-1'-ynyl)-3-hydroxy-6-n-butoxybicyclo[4.2.0]octane-7,2''-(1'',3''-dioxolane)];

(3'S,1S,2R,3S,6S)-spiro[2-(3'-hydroxy-3'-cyclohexylprop-1'-ynyl)-3-hydroxy-6-n-butoxybicyclo[4.2.0]octane-7,2''-(1'',3''-dioxolane)];

(3'S,1S,2S,3R,6R)-spiro[2-(3'-hydroxy-3'-cyclohexylprop-1'-ynyl)-3-hydroxy-6-ethoxy-8-exo-methylbicyclo[4.2.0]octane-7,2''-(1'',3''-dioxolane)];

(3'S,1R,2R,3S,6S)-spiro[2-(3'-hydroxy-3'-cyclohexyl-prop-1'-ynyl)-3-hydroxy-6-ethoxy-8-exo-methylbicyclo[4.2.0]octane-7,2''-(1'',3''-dioxolane)];

(3'S,1S,2S,3R,6R)-spiro[2-(3'-hydroxy-3'-cyclohexyl-prop-1'-ynyl)-3-hydroxy-6-(2,2,2-trifluoroethoxy)-8-endo-methylbicyclo[4.2.0]octane-7,2''-(1'',3''-dioxolane)];

(3'S,1R,2R,3S,6S)-spiro[2-(3'-hydroxy-3'-cyclohexyl-prop-1'-ynyl)-3-hydroxy-6-(2,2,2-trifluoroethoxy)-8-endo-methylbicyclo[4.2.0]octane-7,2''-(1'',3''-dioxolane)];

(3'S,1R,2S,3R,6R)-spiro[2-(3'-hydroxy-3'-cyclopentyl-but-1'-ynyl)-3-hydroxy-6-methoxybicyclo[4.2.0]octane-7,2''-(1'',3''-dioxolane)];

(3'S,1S,2R,3S,6S)-spiro[2-(3'-hydroxy-3'-cyclopentyl-but-1'-ynyl)-3-hydroxy-6-methoxybicyclo[4.2.0]octane-7,2''-(1'',3''-dioxolane)];

(3'S,1R,2S,3R,6R)-spiro[2-(3'-hydroxy-3'-cyclohexyl-but-1'-ynyl)-3-hydroxy-6-methoxybicyclo[4.2.0]octane-7,2''-(1'',3''-dioxolane)];

(3'S,1S,2R,3S,6S)-spiro[2-(3'-hydroxy-3'-cyclohexyl-but-1'-ynyl)-3-hydroxy-6-methoxybicyclo[4.2.0]octane-7,2''-(1'',3''-dioxolane)];

(3'S,1R,2S,3R,6R)-spiro[2-(3'-hydroxy-3'-dec-1'-ynyl)-3-hydroxy-6-methoxybicyclo[4.2.0]octane-7,2''-(1'',3''-dioxolane)];

(3'S,1S,2R,3S,6S)-spiro[2-(3'-hydroxy-3'-dec-1'-ynyl)-3-hydroxy-6-methoxybicyclo[4.2.0]octane-7,2''-(1'',3''-dioxolane)];

(3'S,1S,2S,3R,6R)-spiro[2-(3'-hydroxy-3'-cyclohexyl-prop-1'-ynyl)-3-hydroxy-6-methoxy-8-endo-ethyl-bicyclo[4.2.0]octane-7,2''-(1'',3''-dioxolane)];

(3'S,1R,2R,3S,6S)-spiro[2-(3'-hydroxy-3'-cyclohexyl-prop-1'-ynyl)-3-hydroxy-6-methoxy-8-endo-ethyl-bicyclo[4.2.0]octane-7,2''-(1'',3''-dioxolane)];

(3'S,1S,2S,3R,6R)-spiro[2-(3'-hydroxy-3'-cyclohexyl-prop-1'-ynyl)-3-hydroxy-6-methoxy-8-exo-n-butyl-bicyclo[4.2.0]octane-7,2''-(1'',3''-dioxolane)];

(3'S,1R,2R,3S,6S)-spiro[2-(3'-hydroxy-3'-cyclohexyl-prop-1'-ynyl)-3-hydroxy-6-methoxy-8-exo-n-butyl-bicyclo[4.2.0]octane-7,2''-(1'',3''-dioxolane)];

(3'S,1S,2S,3R,6R)-spiro[2-(3'-hydroxy-3'-cyclohexyl-prop-1'-ynyl)-3-hydroxy-6-n-butoxy-8-endo-n-butyl-bicyclo[4.2.0]octane-7,2''-(1'',3''-dioxolane)]; and (3'S,1R,2R,3S,6S)-spiro[2-(3'-hydroxy-3'-cyclohexyl-prop-1'-ynyl)-3-hydroxy-6-n-butoxy-8-endo-n-butyl-bicyclo[4.2.0]octane-7,2''-(1'',3''-dioxolane)].

PREPARATION 16

A. Preparation of (1'E)-(3'S,1S,2S,3S,6S)-spiro[2-(3'-hydroxy-3'-cyclohexylprop-1'-enyl)-3-hydroxy-6-methoxybicyclo[4.2.0]octane-7,2''-(1'',3''-dioxolane)] and related compounds of formula (LV)

To 2.4 g of lithium aluminum hydride in 80 ml of tetrahydrofuran at room temperature under nitrogen was added 2.4 g of (3'S,1S,2R,3S,6S)-spiro[2-(3'-hydroxy-3'-cyclohexylprop-1'-ynyl)-3-hydroxy-6-methoxybicyclo[4.2.0]octane-7,2''-(1'',3''-dioxolane)], prepared as shown in Preparation 15, was added. The mixture was refluxed for 3 hours, allowed to cool to room temperature and 2.5 ml of water added dropwise with vigorous stirring, followed by 2.5 ml of 15% aqueous sodium hydroxide and 7.5 ml of water. After 15 minutes the mixture was filtered and the filtrate concentrated under reduced pressure. The residue was chromatographed on silica gel, eluting with hexane:ethyl acetate mixture (2:1), giving 2.0 g of (1'E)--(3'S,1S,2S,3S,6S)-spiro[2-(3'-hydroxy-3'-cyclohexylprop-1'-enyl)-3-hydroxy-6-methoxybicyclo[4.2.0]octane-7,2''-(1'',3''-dioxolane)].

B. In like similar manner, following the procedures of paragraph 16.A. above, but starting with the appropriate compounds of formula (LIV), the following exemplary compounds of formula (LV) are made:

(1'E)-(3'S,1R,2R,3R,6R)-spiro[2-(3'-hydroxy-3'-cyclohexylprop-1'-enyl)-3-hydroxy-6-methoxybicyclo[4.2.0]octane-7,2''-(1'',3''-dioxolane)].

(1'E)-(3'R,1R,2R,3R,6R)-spiro[2-(3'-hydroxy-4'-phenoxybut-1'-enyl)-3-hydroxy-6-methoxybicyclo[4.2.0]octane-7,2''-(1'',3''-dioxolane)].

(1'E)-(3'R,1S,2S,3S,6S)-spiro[2-(3'-hydroxy-4'-phenoxybut-1'-enyl)-3-hydroxy-6-methoxybicyclo[4.2.0]octane-7,2''-(1'',3''-dioxolane)].

(1'E)-(3'S,1S,2S,3S,6S)-spiro[2-(3'-hydroxy-4'-(endo-bicyclo[3.1.0]hex-6-yl)but-1'-ynyl)-3-hydroxy-6-methoxybicyclo[4.2.0]octane-7,2''-(1'',3''-dioxolane)].

(1'E)-(3'S,1R,2R,3R,6R)-spiro[2-(3'-hydroxy-4'-(endo-bicyclo[3.1.0]hex-6-yl)but-1'-ynyl)-3-hydroxy-6-methoxybicyclo[4.2.0]octane-7,2''-(1'',3''-dioxolane)].

(1'E)-(3'R,1S,2R,3R,6R)-spiro[2-(3'-hydroxy-4'-phenoxybut-1'-enyl)-3-hydroxy-6-methoxy-8-endo-methylbicyclo-[4.2.0]octane-7,2''-(1'',3''-dioxolane)].

(1'E)-(3'R,1R,2S,3S,6S)-spiro[2-(3'-hydroxy-4'-phenoxybut-1'-enyl)-3-hydroxy-6-methoxy-8-endo-methylbicyclo-[4.2.0]octane-7,2''-(1'',3''-dioxolane)].

(1'E)-(3'S,1R,2R,3R,6R)-spiro[2-(3'-hydroxy-3-cyclohexylprop-1'-enyl)-3-hydroxy-6-(2,2,2-trifluoroethoxy)bicyclo[4.2.0]octane-7,2''-(1'',3''-dioxolane)];

(1'E)-(3'S,1S,2S,3S,6S)-spiro[2-(3'-hydroxy-3-cyclohexylprop-1'-enyl)-3-hydroxy-6-(2,2,2-trifluoroethoxy)bicyclo[4.2.0]octane-7,2''-(1'',3''-dioxolane)];

(1'E)-(3'S,1S,2R,3R,6R)-spiro[2-(3'-hydroxy-3-cyclohexylprop-1'-enyl)-3-hydroxy-6-methoxy-8-exo-methylbicyclo[4.2.0]octane-7,2''-(1'',3''-dioxolane)];

(1'E)-(3'S,1R,2S,3S,6S)-spiro[2-(3'-hydroxy-3-cyclohexylprop-1'-enyl)-3-hydroxy-6-methoxy-8-exo-methylbicyclo[4.2.0]octane-7,2''-(1'',3''-dioxolane)];

(1'E)-(3'S,1S,2R,3R,6R)-spiro[2-(3'-hydroxy-3-cyclohexylprop-1'-enyl)-3-hydroxy-6-methoxy-8-endo-methylbicyclo[4.2.0]octane-7,2''-(1'',3''-dioxolane)];

(1'E)-(3'S,1R,2S,3S,6S)-spiro[2-(3'-hydroxy-3-cyclohexylprop-1'-enyl)-3-hydroxy-6-methoxy-8-endo-methylbicyclo[4.2.0]octane-7,2''-(1'',3''-dioxolane)];

(1'E)-(3'S,1R,2R,3R,6R)-spiro[2-(3'-hydroxy-3'-cyclohexylprop-1'-enyl)-3-hydroxy-6-ethoxybicyclo[4.2.0]octane-7,2''-(1'',3''-dioxolane)];

(1'E)-(3'S,1S,2S,3S,6S)-spiro[2-(3'-hydroxy-3'-cyclohexylprop-1'-enyl)-3-hydroxy-6-ethoxybicyclo[4.2.0]octane-7,2''-(1'',3''-dioxolane)];

(1'E)-(3'S,1R,2R,3R,6R)-spiro[2-(3'-hydroxy-3'-cyclohexylprop-1'-enyl)-3-hydroxy-6-n-butoxybicyclo[4.2.0]octane-7,2''-(1'',3''-dioxolane)];

(1'E)-(3'S,1S,2S,3S,6S)-spiro[2-(3'-hydroxy-3'-cyclohexylprop-1'-enyl)-3-hydroxy-6-n-butoxybicyclo[4.2.0]octane-7,2''-(1'',3''-dioxolane)];

(1'E)-(3'S,1S,2R,3R,6R)-spiro[2-(3'-hydroxy-3'-cyclohexylprop-1'-enyl)-3-hydroxy-6-ethoxy-8-exo-methylbicyclo[4.2.0]octane-7,2''-(1'',3''-dioxolane)];

(1'E)-(3'S,1R,2S,3S,6S)-spiro[2-(3'-hydroxy-3'-cyclohexylprop-1'-enyl)-3-hydroxy-6-ethoxy-8-exo-methylbicyclo[4.2.0]octane-7,2"-(1",3"-dioxolane)];

(1'E)-(3'S,1S,2R,3R,6R)-spiro[2-(3'-hydroxy-3'-cyclohexylprop-1'-enyl)-3-hydroxy-6-(2,2,2-trifluoroethoxy)-8-endo-methylbicyclo[4.2.0]octane-7,2"-(1",3"-dioxolane)];

(1'E)-(3'S,1R,2S,3S,6S)-spiro[2-(3'-hydroxy-3'-cyclohexylprop-1'-enyl)-3-hydroxy-6-(2,2,2-trifluoroethoxy)-8-endo-methylbicyclo[4.2.0]octane-7,2"-(1",3"-dioxolane)];

(1'E)-(3'S,1R,2R,3R,6R)-spiro[2-(3'-hydroxy-3'-cyclopentylbut-1'-enyl)-3-hydroxy-6-methoxybicyclo[4.2.0]octane-7,2"-(1",3"-dioxolane)];

(1'E)-(3'S,1S,2S,3S,6S)-spiro[2-(3'-hydroxy-3'-cyclopentylbut-1'-enyl)-3-hydroxy-6-methoxybicyclo[4.2.0]octane-7,2"-(1",3"-dioxolane)];

(1'E)-(3'S,1R,2R,3R,6R)-spiro[2-(3'-hydroxy-3'-cyclohexylbut-1'-enyl)-3-hydroxy-6-methoxybicyclo[4.2.0]octane-7,2"-(1",3"-dioxolane)];

(1'E)-(3'S,1S,2S,3S,6S)-spiro[2-(3'-hydroxy-3'-cyclohexylbut-1'-enyl)-3-hydroxy-6-methoxybicyclo[4.2.0]octane-7,2"-(1",3"-dioxolane)];

(1'E)-(3'S,1R,2R,3R,6R)-spiro[2-(3'-hydroxy-3'-dec-1'-enyl)-3-hydroxy-6-methoxybicyclo[4.2.0]octane-7,2"-(1",3"-dioxolane)];

(1'E)-(3'S,1S,2S,3S,6S)-spiro[2-(3'-hydroxy-3'-dec-1'-enyl)-3-hydroxy-6-methoxybicyclo[4.2.0]octane-7,2"-(1",3"-dioxolane)];

(3'S,1S,2S,3S,6S)-[2-(3'-hydroxy-4'-(exo-bicyclo[3.1.0]hex-6-yl)but-1'-ynyl)-3-hydroxy-6-methoxybicyclo[4.2.0]octan-7-one;

(3'S,1R,2R,3R,6R)-[2-(3'-hydroxy-4'-(exo-bicyclo[3.1.0]hex-6-yl)but-1'-ynyl)-3-hydroxy-6-methoxybicyclo[4.2.0]octan-7-one;

(1'E)-(3'S,1S,2R,3R,6R)-spiro[2-(3'-hydroxy-3'-cyclohexylprop-1'-enyl)-3-hydroxy-6-methoxy-8-endo-ethylbicyclo[4.2.0]octane-7,2"-(1",3"-dioxolane)];

(1'E)-(3'S,1R,2S,3S,6S)-spiro[2-(3'-hydroxy-3'-cyclohexylprop-1'-enyl)-3-hydroxy-6-methoxy-8-endo-ethylbicyclo[4.2.0]octane-7,2"-(1",3"-dioxolane)];

(1'E)-(3'S,1S,2R,3R,6R)-spiro[2-(3'-hydroxy-3'-cyclohexylprop-1'-enyl)-3-hydroxy-6-methoxy-8-exo-n-butylbicyclo[4.2.0]octane-7,2"-(1",3"-dioxolane)];

(1'E)-(3'S,1R,2S,3S,6S)-spiro[2-(3'-hydroxy-3'-cyclohexylprop-1'-enyl)-3-hydroxy-6-methoxy-8-exo-n-butylbicyclo[4.2.0]octane-7,2"-(1",3"-dioxolane)];

(1'E)-(3'S,1S,2R,3R,6R)-spiro[2-(3'-hydroxy-3'-cyclohexylprop-1'-enyl)-3-hydroxy-6-n-butoxy-8-endo-n-butylbicyclo[4.2.0]octane-7,2"-(1",3"-dioxolane)]; and (1'E)-(3'S,1R,2S,3S,6S)-spiro[2-(3'-hydroxy-3'-cyclohexylprop-1'-enyl)-3-hydroxy-6-n-butoxy-8-endo-n-butylbicyclo[4.2.0]octane-7,2"-(1",3"-dioxolane)].

PREPARATION 17

Preparation of (1'E)-(3'S,1S,2S,3S,6S) and (1'E)-(3'R,1S,2S,3S,6S)-2-(3'-hydroxy-3'-cyclohexylprop-1'-enyl)-3-hydroxy-6-methoxybicyclo[4.2.0]octan-7-one and Related Compounds of Formula (LVI) and (LVII)

A. A solution of 2.0 g of (1'E)-(3'S,1S,2S,3S,6S) spiro[2-(3'-hydroxy-3'-cyclohexylprop-1'-enyl)-3-hydroxy-6-methoxybicyclo[4.2.0]octane-7,2"-(1",3"-dioxolane)], prepared as shown in Preparation 16, 30 ml of acetonitrile and 15 ml of 1.2M sulfuric acid was stirred at 65° C. for 2 hours. The reaction was quenched by neutralization at room temperature with aqueous sodium bicarbonate and the reaction mixture extracted with diethyl ether. The extracts were dried with magnesium sulfate, the solvent removed under reduced pressure and the residue chromatographed on silica gel, eluting with ethyl acetate-hexane (1:1), to give 281 mg of (1'E)-(3'S,1S,2S,3S,6S)-2-(3'-hydroxy-3'-cyclohexylprop-1'-enyl)-3-hydroxy-6-methoxybicyclo[4.2.0]octan-7-one and 253 mg of (1'E)-(3'R,1S,2S,3S,6S)-2-(3'-hydroxy-3'-cyclohexylprop-1'-enyl)-3-hydroxy-6-methoxybicyclo[4.2.0]octan-7-one.

B. In a similar manner, following the procedures of paragraph 17.A. above, but starting with the appropriate ketal of formula (LV), the following compounds of formula (LVI) and (LVII) were prepared:

(1'E)-(3'S,1R,2R,3R,6R)-2-(3'-hydroxy-3'-cyclohexylprop-1'-enyl)-3-hydroxy-6-methoxybicyclo[4.2.0]octan-7-one; and (1'E)-(3'R,1R,2R,3R,6R)-2-(3'-hydroxy-3'-cyclohexylprop-1'-enyl)-3-hydroxy-6-methoxybicyclo[4.2.0]octan-7-one.

C. Similarly, following the procedures of paragraph 17.A. above, the following exemplary compounds of formula (LVI) and (LVII) are made:

(1'E)-(3'S,1S,2S,3S,6S)-2-(3'-hydroxy-3'-cyclohexylprop-1'-enyl)-3-hydroxy-6-(2,2,2-trifluoroethoxy)-bicyclo[4.2.0]octan-7-one;

(1'E)-(3'R,1S,2S,3S,6S)-2-(3'-hydroxy-3'-cyclohexylprop-1'-enyl)-3-hydroxy-6-(2,2,2-trifluoroethoxy)-bicyclo[4.2.0]octan-7-one;

(1'E)-(3'S,1S,2S,3S,6S)-2-(3'-hydroxy-3'-cyclohexylprop-1'-enyl)-3-hydroxy-6-n-butoxybicyclo[4.2.0]octan-7-one;

(1'E)-(3'R,1S,2S,3S,6S)-2-(3'-hydroxy-3'-cyclohexylprop-1'-enyl)-3-hydroxy-6-butoxybicyclo[4.2.0]octan-7-one;

(1'E)-(3'R,1S,2S,3S,6S)-2-(3'-hydroxy-4'-phenoxybut-1'-enyl)-3-hydroxy-6-methoxybicyclo[4.2.0]octan-7-one (1'E)-(3'S,1S,2S,3S,6S)-2-(3'-hydroxy-4'-phenoxybut 1'-enyl)-3-hydroxy-6-methoxy-bicyclo[4.2.0]octan-7-one.

(1'E)-(3'S,1S,2S,3S,6S)-2-(3'-hydroxy-4'-cyclopentylbut-1'-enyl)-3-hydroxy-6-methoxybicyclo[4.2.0]octan-7-one;

(1'E)-(3'R,1S,2S,3S,6S)-2-(3'-hydroxy-4'-cyclopentylbut-1'-enyl)-3-hydroxy-6-methoxybicyclo[4.2.0]octan-7-one;

(1'E)-(3'S,1S,2S,3S,6S)-2-(3'-hydroxy-4'-cyclohexylbut-1'-enyl)-3-hydroxy-6-methoxybicyclo[4.2.0]octan-7-one;

(1'E)-(3'R,1S,2S,3S,6S)-2-(3'-hydroxy-4'-cyclohexylbut-1'-enyl)-3-hydroxy-6-methoxybicyclo[4.2.0]octan-7-one;

(1'E)-(3'S,1R,2S,3S,6S)-2-(3'-hydroxy-3'-cyclohexylprop-1'-enyl)-3-hydroxy-6-methoxy-8-exo-methylbicyclo[4.2.0]-octan-7-one;

(1'E)-(3'R,1R,2S,3S,6S)-3'-hydroxy-3'-cyclohexylprop-1'-enyl)-3-hydroxy-6-methoxy-8-exo-methylbicyclo[4.2.0]-octan-7-one;

(1'E)-(3'S,1R,2S,3S,6S)-2-(3'-hydroxy-3'-cyclohexylprop-1'-enyl)-3-hydroxy-6-methoxy-8-endo-methylbicyclo[4.2.0]octan-7-one;

(1'E)-(3'R,1R,2S,3S,6S)-2-(3'-hydroxy-3'-cyclohexyl-prop-1'-enyl)-3-hydroxy-6-methoxy-8-endo-methylbicyclo[4.2.0]octan-7-one;

(1'E)-(3'S,1R,2S,3S,6S)-2-(3'-hydroxy-3'-cyclohexyl-prop-1'-enyl)-3-hydroxy-6-ethoxy-8-exo-methylbicyclo[4.2.0]octan-7-one;

(1'E)-(3'R,1R,2S,3S,6S)-2-(3'-hydroxy-3'-cyclohexyl-prop-1'-enyl)-3-hydroxy-6-methoxy-8-exo-methylbicyclo[4.2.0]-octan-7-one;

(1'E)-(3'S,1R,2S,3S,6S)-2-(3'-hydroxy-3'-cyclohexyl-prop-1'-enyl)-3-hydroxy-6-(2,2,2-trifluoroethoxy)-8-endo-methylbicyclo[4.2.0]octan-7-one;

(1'E)-(3'R,1R,2S,3S,6S)-2-(3'-hydroxy-3'-cyclohexyl-prop-1'-enyl)-3-hydroxy-6-(2,2,2-trifluoroethoxy)-8-endo-methylbicyclo[4.2.0]octan-7-one;

(1'E)-(3'S,1R,2R,3R,6R)-2-(3'-hydroxy-cyclohexyl-prop-1'-enyl)-3-hydroxy-6-(2,2,2-trifluoroethoxy)-bicyclo[4.2.0]octan-7-one;

(1'E)-(3'S,1R,2R,3R,6R)-2-(3'-hydroxy-3'-cyclohexyl-prop-1'-enyl)-3-hydroxy-6-n-butoxybicyclo[4.2.0]octan-7-one;

(1'E)-(3'S,1R,2R,3R,6R)-2-(3'-hydroxy-4'-cyclopentyl-but-1'-enyl)-3-hydroxy-6-methoxybicyclo[4.2.0]octan-7-one;

(1'E)-(3'S,1R,2R,3R,6R)-2-(3'-hydroxy-4'-cyclohexyl-but-1'-enyl)-3-hydroxy-6-methoxybicyclo-8 4.2.0]octan-7-one;

(1'E)-(3'S,1S,2R,3R,6R)-2-(3'-hydroxy-3'-cyclohexyl-prop-1'-enyl)-3-hydroxy-6-methoxy-8-exo-methylbicyclo[4.2.0]octan-7-one;

(1'E)-(3'S,1S,2R,3R,6R)-2-(3'-hydroxy-3'-cyclohexyl-prop-1'-enyl)-3-hydroxy-6-methoxy-8-endo-methylbicyclo[4.2.0]octan-7-one;

(1'E)-(3'S,1S,2R,3R,6R)-2-(3'-hydroxy-3'-cyclohexyl-prop-1'-enyl)-3-hydroxy-6-ethoxy-8-exo-methylbicyclo[4.2.0]octan-7-one;

(1'E)-(3'S,1S,2R,3R,6R)-2-(3'-hydroxy-3'-cyclohexyl-prop-1'-enyl)-3-hydroxy-6-(2,2,2-trifluoroethoxy)-8-endo-methylbicyclo[4.2.0]octan-7-one;

(1'E)-(3'S,1R,2S,3S,6S)-2-(3'-hydroxy-3'-cyclohexyl-prop-1'-enyl)-3-hydroxy-6-methoxy-8-endo-ethylbicyclo[4.2.0]octan-7-one;

(1'E)-(3'R,1R,2S,3S,6S)-2-(3'-hydroxy-3'-cyclohexyl-prop-1'-enyl)-3-hydroxy-6-methoxy-8-endo-ethylbicyclo[4.2.0]octan-7-one;

(1'E)-(3'S,1S,2R,3R,6R)-2-(3'-hydroxy-3'-cyclohexyl-prop-1'-enyl)-3-hydroxy-6-methoxy-8-endo-ethylbicyclo[4.2.0]octan-7-one;

(1'E)-(3'S,1R,2S,3S,6S)-2-(3'-hydroxy-3'-cyclohexyl-prop-1'-enyl)-3-hydroxy-6-methoxy-8-exo-n-butylbicyclo[4.2.0]octan-7-one;

(1'E)-(3'R,1R,2S,3S,6S)-2-(3'-hydroxy-3'-cyclohexyl-prop-1'-enyl)-3-hydroxy-6-methoxy-8-exo-n-butylbicyclo[4.2.0]octan-7-one;

(1'E)-(3'S,1S,2R,3R,6R)-2-(3'-hydroxy-3'-cyclohexyl-prop-1'-enyl)-3-hydroxy-6-methoxy-8-exo-n-butylbicyclo[4.2.0]octan-7-one;

(1'E)-(3'S,1R,2S,3S,6S)-2-(3'-hydroxy-3'-cyclohexyl-prop-1'-enyl)-3-hydroxy-6-butoxy-8-endo-n-butylbicyclo[4.2.0]octan-7-one;

(1'E)-(3'R,1R,2S,3S,6S)-2-(3'-hydroxy-3'-cyclohexyl-prop-1'-enyl)-3-hydroxy-6-butoxy-8-endo-n-butylbicyclo[4.2.0]octan-7-one; and (1'E)-(3'S,1S,2R,3R,6R)-2-(3'-hydroxy-3'-cyclohexyl-prop-1'-enyl)-3-hydroxy-6-butoxy-8-endo-n-butylbicyclo[4.2.0]octan-7-one.

PREPARATION 18

Preparation of (3'SR,1RS,2SR,3RS,6RS)-2-(3'-hydroxy-3'-cyclohexyl-prop-1'-ynyl)-3,6-dihydroxybicyclo[4.2.0]octan-7-one and Related Compounds of Formula (XIV) and (XV) where X is hydroxy A. A solution of 400 mg of (3'SR,1RS,2SR,3RS,6RS)-2-(3'-hydroxy-3'-cyclohexyl-prop-1'-ynyl)-3-hydroxy-6-methoxybicyclo[4.2.0]octan-7-one, prepared as shown in Preparation 14, in 1 ml of acetone and 2 ml of 48% hydrobromic acid was stirred at room temperature for 24 hours. The reaction mixture was poured into water and extracted with ethyl acetate. The extract was dried over anhydrous sodium sulfate and the solvent removed under reduced pressure. The residue was chromatographed on silica gel, eluting with ethyl acetate-hexane (2:1) to give 230 mg of (3'SR,1RS,2SR,3RS,6RS)-2-(3'-hydroxy-3'-cyclohexyl-prop-1'-ynyl)-3,6-dihydroxybicyclo[4.2.0]octan-7-one.

B. In a like manner, following the procedure of paragraph 18.A. above, but substituting the appropriate 6-alkoxyketone of formula (XIV), (XV) (LVI) or (LVII) for 2-(3'-hydroxy-3-cyclohexylprop-1'-ynyl)-3-hydroxy-6-methoxybicyclo[4.2.0]octan-7-one the following exemplary compounds of formula (XIV) and (XV) where X is hydroxy are prepared:

(3'S,1R,2S,3R,6R)-2-(3'-hydroxy-4'-cyclohexylbut-1'-ynyl)-3,6-dihydroxybicyclo[4.2.0]octan-7-one;

(3'S,1S,2R,3S,6S)-2-(3'-hydroxy-4'-cyclohexylbut-1'-ynyl)-3,6-dihydroxybicyclo[4.2.0]octan-7-one;

(3'S,1R,2S,3R,6R)-2-(3'-hydroxy-4'-cyclopentylbut-1'-ynyl)-3,6-dihydroxybicyclo[4.2.0]octan-7-one;

(3'S,1S,2R,3S,6S)-2-(3'-hydroxy-4'-cyclopentylbut-1'-ynyl)-3,6-dihydroxybicyclo[4.2.0]octan-7-one;

(3'S,1R,2S,3R,6R)-2-(3'-hydroxy-3'-cyclopentylprop-1'-ynyl)-3,6-dihydroxybicyclo[4.2.0]octan-7-one;

(3'S,1S,2R,3S,6S)-2-(3'-hydroxy-3'-cyclopentylprop-1'-ynyl)-3,6-dihydroxybicyclo[4.2.0]octan-7-one;

(3'S,1R,2S,3R,6R)-2-(3'-hydroxydec-1'-ynyl)-3,6-dihydroxybicyclo[4.2.0]octan-7-one;

(3'S,1S,2R,3S,6S)-2-(3'-hydroxydec-1'-ynyl)-3,6-dihydroxybicyclo[4.2.0]octan-7-one;

(1'E)-(3'S,1R,2R,3R,6R)-2-(3'-hydroxy-3'-cyclohexyl-prop-1'-enyl)-3,6-dihydroxybicyclo[4.2.0]octan-7-one;

(1'E)-(3'S,1S,2S,3S,6S)-2-(3'-hydroxy-3'-cyclohexyl-prop-1'-enyl)-3,6-dihydroxybicyclo[4.2.0]octan-7-one;

(1'E)-(3'S,1R,2R,3R,6R)-2-(3'-hydroxy-3'-cyclopentyl-prop-1'-enyl)-3,6-dihydroxybicyclo[4.2.0]octan-7-one;

(1'E)-(3'S,1S,2S,3S,6S)-2-(3'-hydroxy-3'-cyclopentyl-prop-1'-enyl)-3,6-dihydroxybicyclo[4.2.0]octan-7-one;

(3'S,1R,2S,3R,6R)-2-(3'-hydroxydec-1'-ynyl)-3,6-dihydroxybicyclo[4.2.0]octan-7-one;

(3'S,1S,2R,3S,6S)-2-(3'-hydroxydec-1'-ynyl)-3,6-dihydroxybicyclo[4.2.0]octan-7-one;

(3'S,1S,2S,3R,6R)-2-(3'-hydroxy-4'-cyclohexylbut-1'-ynyl)-3,6-dihydroxy-8-exo-methylbicyclo[4.2.0]octan-7-one;

(3'S,1R,2R,3S,6S)-2-(3'-hydroxy-4'-cyclohexylbut-1'-ynyl)-3,6-dihydroxy-8-exo-methylbicyclo[4.2.0]octan-7-one;

(3'S,1S,2S,3R,6R)-2-(3'-hydroxy-4'-cyclopentylbut-1'-ynyl)-3,6-dihydroxy-8-endo-methylbicyclo[4.2.0]octan-7-one;

(3'S,1R,2R,3S,6S)-2-(3'-hydroxy-4'-cyclopentylbut-1'-ynyl)-3,6-dihydroxy-8-endo-methylbicyclo[4.2.0]octan-7-one;

(3'S,1S,2S,3R,6R)-2-(3'-hydroxy-3'-cyclopentylprop-1'-ynyl)-3,6-dihydroxy-8-exo-methylbicyclo-[4.2.0]octan-7-one;

(3'S,1R,2R,3S,6S)-2-(3'-hydroxy-3'-cyclopentylprop-1'-ynyl)-3,6-dihydroxy-8-exo-methylbicyclo[4.2.0]octan-7-one;

(3'S,1S,2S,3R,6R)-2-(3'-hydroxydec-1'-ynyl)-3,6-dihydroxy-8-endo-methylbicyclo[4.2.0]octan-7-one;

(3'S,1R,2R,3S,6S)-2-(3'-hydroxydec-1'-ynyl)-3,6-dihydroxy-8-endo-methylbicyclo[4.2.0]octan-7-one;

(1'E)-(3'S,1S,2R,3R,6R)-2-(3'-hydroxy-3'-cyclohexylprop-1'-enyl)-3,6-dihydroxy-8-exo-methylbicyclo[4.2.0]octan-7-one;

(1'E)-(3'S,1R,2S,3S,6S)-2-(3'-hydroxy-3'-cyclohexylprop-1'-enyl)-3,6-dihydroxy-8-exo-methylbicyclo[4.2.0]octan-7-one;

(1'E)-(3'S,1S,2R,3R,6R)-2-(3'-hydroxy-3'-cyclopentylprop-1'-enyl)-3,6-dihydroxy-8-endo-methylbicyclo[4.2.0]octan-7-one;

(1'E)-(3'S,1R,2S,3S,6S)-2-(3'-hydroxy-3'-cyclopentylprop-1'-enyl)-3,6-dihydroxy-8-endo-methylbicyclo[4.2.0]octan-7-one;

(3'S,1S,2S,3R,6R)-2-(3'-hydroxydec-1'-ynyl)-3,6-dihydroxy-8-endo-methylbicyclo[4.2.0]octan-7-one;

(3'S,1R,2R,3S,6S)-2-(3'-hydroxydec-1'-ynyl)-3,6-dihydroxy-8-endo-methylbicyclo[4.2.0]octan-7-one;

(1'E)-(3'S,1R,2S,3S,6S)-2-(3'-hydroxy-4'-cyclopentylbut-1'-enyl)-3,6-dihydroxy-8-exo-methylbicylo[4.2.0]octan-7-one;

(1'E)-(3'S,1S,2R,3R,6R)-2-(3'-hydroxydec-1'-enyl)-3,6-dihydroxy-8-exo-methylbicyclo[4.2.0]octan-7-one;

(1'E)-(3'S,1R,2S,3S,6S)-2-(3'-hydroxydec-1'-enyl)-3,6-dihydroxy-8-exo-methylbicyclo[4.2.0]octan-7-one;

(3'S,1S,2S,3R,6R)-2-(3'-hydroxy-3'-cyclohexyl-prop-1'-ynyl)-3,6-dihydroxy-8-endo-ethylbicyclo[4.2.0]octan-7-one;

(3'S,1R,2R,3S,6S)-2-(3'-hydroxy-3'-cyclohexyl-prop-1'-ynyl)-3,6-dihydroxy-8-endo-ethylbicyclo[4.2.0]octan-7-one;

(3'S,1S,2S,3R,6R)-2-(3'-hydroxy-3'-cyclohexyl-prop-1'-ynyl)-3,6-dihydroxy-8-exo-n-butylbicyclo[4.2.0]octan-7-one; and (3'S,1R,2R,3S,6S)-2-(3'-hydroxy-3'-cyclohexylprop-1'-ynyl)-3,6-dihydroxy-8-exo-n-butylbicyclo[4.2.0]octan-7-one.

PREPARATION 19

A. Preparation of a mixture of (1'E)-(3'S,1S,2S,3S,6S)- and (1'E)-(3'S,1R,2R,3R,6R)-2-(3'-hydroxy-3'-cyclohexyl-prop-1'-enyl)-3-hydroxy-6-methoxybicyclo[4.2.0]octan-7-one and related mixtures of compounds of formula (LVI) and (LVIA)

(a) A mixture of 1.2 g of (S)-3-t-butyldimethylsilyloxy-3-cyclohexyl-1-propyne and 1.5 g of tri-n-butyltin hydride was heated at 85° C. for 1 hour in the presence of 3 mg of azobisisobutyronitrile. The temperature was raised to 125° C. for 1 hour, and excess tri-n-butyltin hydride then removed by careful distillation.

(b) A solution of 1.6 g of tri-n-butyl[3-(S)-t-butyldimethylsilyloxy-3-cyclohexyl-(1E)-propenyl]stannane, prepared as shown in paragraph 19(a), in tetrahydrofuran was cooled to −78° C. under nitrogen and 1 molar equivalent of n-butyl lithium added. The mixture was stirred at −40° C. for 1 hour, then recooled to −78° C. A solution of 300 mg of a mixture of (1RS,2SR,3RS,6RS)-spiro[2,3-epoxy-6-methoxy-bicyclo[4.2.0]octane-7,2''-(1'',3''-dioxolane)] and (1RS,2RS,3SR,6RS)-spiro-[2,3-epoxy-6-methoxybicyclo[4.2.0]octane-7,2''-(1'',3''-dioxolane)] in 3 ml tetrahydrofuran was added. To this stirred mixture at −78° C. was added 0.25 ml boron trifluoride etherate dropwise over a 1 hour period, followed by 25 ml of saturated sodium sulfate solution. The resulting mixture was warmed to room temperature and extracted thoroughly with ethyl acetate. This solution was dried over sodium sulfate and concentrated in vacuo to give an oily residue. Volatiles were removed on a Kugelrohr distillation device at 95° C. (0.1 mm Hg) to leave 260 mg of a residue, which was further purified by flash chromatography on silica gel using 1.8% acetone-dichloromethane. Acid hydrolysis of the product thus obtained using the conditions as described in Preparation 14, gives the title compounds.

B. In a similar manner, following the procedure of paragraphs 19.A. above, the following exemplary mixtures of compounds of formula (LVI) and (LVIA) or (LVII) and its diastereomer, where Y is H, or exo or endo-(lower alkyl), are prepared:

(1'E)-(3'S,1S,2S,3S,6S)- and (1'E)-(3'S,1R,2R,3R,6R)-2-(3'-hydroxy-3'-cyclohexylprop-1'-enyl)-3-hydroxy-6-butoxybicyclo[4.2.0]octan-7-one;

(1'E)-(3'S,1S,2S,3S,6S)- and (1'E)-(3'S,1R,2R,3R,6R)-2-(3'-hydroxy-4'-cyclopentylbut-1'-enyl)-3-hydroxy-6-methoxybicyclo[4.2.0]octan-7-one;

(1'E)-(3'S,1S,2S,3S,6S)- and (1'E)-(3'S,1R,2R,3R,6R)-2-(3'-hydroxy-5',9'-dimethyldec-1',8'-dien-1'-yl)-3-hydroxy-6-methoxybicyclo[4.2.0]octan-7-one;

(1'E)-(3'S,1R,2S,3S,6S)- and (1'E)-(3'S,1S,2R,3R,6R)-2-(3'-hydroxy-5',9'-dimethyldec-1',8'-dien-1'-yl)-3-hydroxy-6-methoxy-8-methylbicyclo[4.2.0]octan-7-one;

(1'E)-(3'S,1S,2S,3S,6S)- and (1'E)-(3'S,1R,2R,3R,6R)-2-(3'-hydroxy-4'-cyclohexylbut-1'-enyl)-3-hydroxy-6-methoxybicyclo[4.2.0]octan-7-one;

(1'E)-(3'R,1S,2S,3S,6S)- and (1'E)-3'R,1R,2R,3R,6R)-2-(3'-hydroxy-4'-phenoxybut-1'enyl)-3-hydroxy-6-methoxybicyclo[4.2.0]octan-7-one;

(1'E)-(3'R,1R,2S,3S,6S)- and (1'E)-(3'R,1S,2R,3R,6R)-2-(3'-hydroxy-4'-phenoxybut-1'-enyl)-3-hydroxy-6-methoxy-8-methylbicyclo[4.2.0]octan-7-one;

(1'E)-(3'S,1R,2S,3S,6S)- and (1'E)-(3'S,1S,2R,3R,6R)-2-(3'-hydroxy-3'-cyclohexylprop-1'-enyl)-3-hydroxy-6-methoxy-8-exo-methylbicyclo[4.2.0]-octan-7-one;

(1'E)-(3'S,1R,2S,3S,6S)- and (1'E)-(3'S,1S,2R,3R,6R)-2-(3'-hydroxy-3'-cyclohexylprop-1'-enyl)-3-hydroxy-6-methoxy-8-endo-methylbicyclo[4.2.0]-octan-7-one;

(1'E)-(3'S,1R,2S,3S,6S)- and (1'E)-(3'S,1S,2R,3R,6R)-2-(3'-hydroxy-3'-cyclohexylprop-1'-enyl)-3-hydroxy-6-ethoxy-8-exo-methylbicyclo[4.2.0]octan-7-one;

(1'E)-(3'S,1R,2S,3S,6S)- and (1'E)-(3'E)-(3'S,1S,2R,3R,6R)-2-(3'-hydroxy-3'-cyclohexylprop-1'-enyl)-3-hydroxy-6-(2,2,2-trifluoroethoxy)-8-endo-methylbicyclo[4.2.0]octan-7-one;

(1'E)-(3'S,1S,2R,3R,6R)- and (1'E)-(3'S,1R,2S,3S,6S)-2-(3'hydroxy-3'-cyclohexylprop-1'-enyl)-3-hydroxy-6-methoxy-8-ethylbicyclo[4.2.0]octan-7-one;

(1'E)-(3'S,1S,2R,3R,6R)- and (1'E)-(3'S,1R,2S,3S,6S)-2-(3'hydroxy-3'-cyclohexylprop-1'-enyl)-3-hydroxy-6-methoxy-8-n-butylbicyclo[4.2.0]octan-7-one; and (1'E)-(3'S,1S,2R,3R,6R)- and (1'E)-(3'S,1R,2S,3S,6S)-2-(3'hydroxy-3'-cyclohexylprop-1'-enyl)-3-hydroxy-6-n-butoxy-8-n-butylbicyclo[4.2.0]octan-7-one.

PREPARATION 20

A. Preparation of (3'S,1S,2R,3S,6S)-2-(3'-tert-butyldimethylsilyloxy-3'-cyclohexylprop-1'-ynyl)-3-tert-butyldimethylsilyloxy-6-methoxybicyclo[4.2.0]octan-7-one and related compounds of Formula (XXXIII) and (XXXIV)

A mixture of 0.52 g (3'S,1S,2R,3S,6S)4-[2-(3'-hydroxy-3'-cyclohexylprop-1'-ynyl)-3-hydroxy-6-methoxybicyclo[4.2.0]octan-7-one, 0.55 g tert-butyldimethylsilyl chloride, 0.18 g 4-dimethylaminopyridine, 2 g of imidazole and 10 ml dichloromethane is stirred at 23° C. the 24 hours. After dilution with 20 ml of dichloromethane the mixture is washed with 10 ml water, three 20-ml portions of 1N HCl and 10 ml sat. sodium bicarbonate. After drying over sodium sulfate the solvent is removed to give the title compound.

B. In like manner, following the procedure of paragraph 20.A. above, but starting with other appropriate compounds of formula (XIV) or (XV) the following exemplary compounds of formula (XXXIII) or (XXXIV) where Y is H, or exo or endo-(lower alkyl) are obtained:

(3'S,1R,2S,3R,6R)-2-(3'-tert-butyldimethylsilyloxy-3'-cyclohexylprop-1'-ynyl)-3-tert-butyldimethylsilyloxy-6-methoxybicyclo-[4.2.0]octan-7-one (3'R,1R,2S,3R,6R)-2-(3'-tert-butyldimethylsilyloxy-4'-phenoxybut-1'-ynyl)-3-tert-butyldimethylsilyloxy-6-methoxybicyclo-[4.2.0]octan-7-one (3'R,1S,2R,3S,6S)-2-(3'-tert-butyldimethylsilyloxy-4'-phenoxybut-1'-ynyl)-3-tert-butyldimethylsilyloxy-6-methoxybicyclo-[4.2.0]octan-7-one (3'R,1R,2S,3R,6R)-2-(3'-tert-butyldimethylsilyloxy-4'-phenoxybut-1'-ynyl)-3-tert-butyldimethylsilyloxy-6-methoxy-8-methylbicyclo-[4.2.0]octan-7-one (3'R,1R,2R,3S,6S)-2-(3'-tert-butyldimethylsilyloxy-4'-phenoxybut-1'-ynyl)-3-tert-butyldimethylsilyloxy-6-methoxy-8-methylbicyclo-[4.2.0]octan-7-one (3'S,1R,2S,3R,6R)-2-(3'-t-butyldimethylsilyloxy-3'-cyclohexylprop-1'-ynyl)-3-t-butyldimethylsilyloxy-6-(2,2,2-trifluoroethoxy)bicyclo[4.2.0]octan-7-one;

(3'S,1S,2R,3S,6S)-2-(3'-t-butyldimethylsilyloxy-3'-cyclohexylprop-1'-ynyl)-3-t-butyldimethylsilyloxy-6-(2,2,2-trifluoroethoxy)bicyclo[4.2.0]octan-7-one;

(3'S,1S,2S,3R,6R)-2-(3'-t-butyldimethylsilyloxy-3'-cyclohexylprop-1'-ynyl)-3-t-butyldimethylsilyloxy-6-methoxy-8-methylbicyclo[4.2.0]octan-7-one;

(3'S,1R,2R,3S,6S)-2-(3'-t-butyldimethylsilyloxy-3'-cyclohexylprop-1'-ynyl)-3-t-butyldimethylsilyloxy-6-methoxy-8-methylbicyclo[4.2.0]octan-7-one;

(3'S,1R,2S,3R,6R)-2-(3'-t-butyldimethylsilyloxy-3'-cyclohexylprop-1'-ynyl)-3-t-butyldimethylsilyloxy-6-ethoxybicyclo[4.2.0]octan-7-one;

(3'S,1S,2R,3S,6S)-2-(3'-t-butyldimethylsilyloxy-3'-cyclohexylprop-1'-ynyl)-3-t-butyldimethylsilyloxy-6-ethoxybicyclo[4.2.0]octan-7-one;

(3'S,1R,2S,3R,6R)-2-(3'-t-butyldimethylsilyloxy-3'-cyclohexylprop-1'-ynyl)-3-t-butyldimethylsilyloxy-6-n-butoxybicyclo[4.2.0]octan-7-one;

(3'S,1S,2R,3S,6S)-2-(3'-t-butyldimethylsilyloxy-3'-cyclohexylprop-1'-ynyl)-3-t-butyldimethylsilyloxy-6-n-butoxybicyclo[4.2.0]octan-7-one;

(3'S,1S,2S,3R,6R)-2-(3'-t-butyldimethylsilyloxy-3'-cyclohexylprop-1'-ynyl)-3-t-butyldimethylsilyloxy-6-ethoxy-8-methylbicyclo[4.2.0]octan-7-one;

(3'S,1R,2R,3S,6S)-2-(3'-t-butyldimethylsilyloxy-3'-cyclohexylprop-1'-ynyl)-3-t-butyldimethylsilyloxy-6-ethoxy-8-methylbicyclo[4.2.0]octan-7-one;

(3'S,1S,2S,3R,6R)-2-(3'-t-butyldimethylsilyloxy-3'-cyclohexylprop-1'-ynyl)-3-t-butyldimethylsilyloxy-6-(2,2,2-trifluoroethoxy)-8-methylbicyclo[4.2.0]octan-7-one;

(3'S,1R,2R,3S,6S)-2-(3'-t-butyldimethylsilyloxy-3'-cyclohexylprop-1'-ynyl)-3-t-butyldimethylsilyloxy-6-(2,2,2-trifluoroethoxy)-8-methylbicyclo[4.2.0]octan-7-one;

(3'S,1R,2S,3R,6R)-2-(3'-t-butyldimethylsilyloxy-3'-cyclopentylbut-1'-ynyl)-3-t-butyldimethylsilyloxy-6-methoxybicyclo[4.2.0]octan-7-one;

(3'S,1S,2R,3S,6S)-2-(3'-t-butyldimethylsilyloxy-3'-cyclopentylbut-1'-ynyl)-3-t-butyldimethylsilyloxy-6-methoxybicyclo[4.2.0]octan-7-one;

(3'S,1R,2S,3R,6R)-2-(3'-t-butyldimethylsilyloxy-3'-cyclohexylbut-1'-ynyl)-3-t-butyldimethylsilyloxy-6-methoxybicyclo[4.2.0]octan-7-one;

(3'S,1S,2R,3S,6S)-2-(3'-t-butyldimethylsilyloxy-3'-cyclohexylbut-1'-ynyl)-3-t-butyldimethylsilyloxy-6-methoxybicyclo[4.2.0]octan-7-one;

(3'S,1R,2S,3R,6R)-2-(3'-t-butyldimethylsilyloxy-3'-dec-1'-ynyl)-3-hydroxy-6-methoxybicyclo[4.2.0]octan-7-one;

(3'S,1S,2R,3S,6S)-2-(3'-t-butyldimethylsilyloxy-3'-dec-1'-ynyl)-3-hydroxy-6-methoxybicyclo[4.2.0]octan-7-one;

(1'E)-(3'S,1S,2S,3S,6S)-2-(3'-t-butyldimethylsilyloxycyclohexylprop-1'-enyl)-3-t-butyldimethylsilyloxy-6-(2,2,2-trifluoroethoxy)bicyclo[4.2.0]octan-7-one;

(1'E)-(3'R,1S,2S,3S,6S)-2-(3'-t-butyldimethylsilyloxy-3'-cyclohexylprop-1'-enyl)-3-t-butyldimethylsilyloxy-6-(2,2,2-trifluoroethoxy)bicyclo[4.2.0]octan-7-one;

(1'E)-(3'S,1S,2S,3S,6S)-2-(3'-t-butyldimethylsilyloxy-3'-cyclohexylprop-1'-enyl)-3-t-butyldimethylsilyloxy-6-n-butoxybicyclo[4.2.0]octan-7-one;

(1'E)-(3'R,1S,2S,3S,6S)-2-(3't-butyldimethylsilyloxy-3'-cyclohexylprop-1'-enyl)-3-t-butyldimethylsilyloxy-6-butoxybicyclo[4.2.0]octan-7-one;

(1'E)-(3'S,1S,2S,3S,6S)-2-(3'-t-butyldimethylsilyloxy-4'-cyclopentylbut-1'-enyl)-3-t-butyldimethylsilyloxy-6-methoxybicyclo[4.2.0]octan-7-one;

(1'E)-(3'R,1S,2S,3S,6S)-2-(3'-t-butyldimethylsilyloxy-4'-cyclopentylbut-1'-enyl)-3-t-butyldimethylsilyloxy-6-methoxybicyclo[4.2.0]octan-7-one;

(1'E)-(3'S,1S,2S,3S,6S)-2-(3'-t-butyldimethylsilyloxy-4'-cyclohexylbut-1'-enyl)-3-t-butyldimethylsilyloxy-6-methoxybicyclo[4.2.0]octan-7-one;

(1'E)-(3'R,1S,2S,3S,6S)-2-(3'-t-butyldimethylsilyloxy-4'-cyclohexylbut-1'-enyl)-3-t-butyldimethylsilyloxy-6-methoxybicyclo[4.2.0]octan-7-one;

(1'E)-(3'S,1R,2S,3S,6S)-2-(3'-t-butyldimethylsilyloxy-3'-cyclohexylprop-1'-enyl)-3-t-butyldimethylsilyloxy-6-methoxy-8-exo-methylbicyclo[4.2.0]octan-7-one;

(1'E)-(3'S,1R,2S,3S,6S)-2-(3'-t-butyldimethylsilyloxy-3'-cyclohexylprop-1'-enyl)-3-t-butyldimethylsilyloxy-6-methoxy-8-endo-methylbicyclo[4.2.0]octan-7-one;

(1'E)-(3'S,2R,3R,6R)-2-(3'-t-butyldimethylsilyloxy-3'-cyclohexylprop-1'-enyl)-3-t-butyldimethylsilyloxy-6-ethoxy-8-methylbicyclo[4.2.0]octan-7-one;

(3'R,1R,2R,3S,6S)-2-(3'-t-butyl-dimethylsilyloxy-3'-cyclohexylprop-1'-ynyl)-3-t-butyldimethylsilyloxy-6-methoxy-8-ethylbicyclo[4.2.0]octan-7-one;

(3'S,1R,2R,3S,6S)-2-(3'-t-butyl-dimethylsilyloxy-3'-cyclohexylprop-1'-ynyl)-3-t-butyldimethylsilyloxy-6-methoxy-8-ethylbicyclo[4.2.0]octan-7-one;

(3'R,1R,2R,3S,6S)-2-(3'-t-dimethylsilyloxy-3'-cyclohexylprop-1'-ynyl)-3-t-butyldimethylsilyloxy-6-methoxy-8-n-butylbicyclo[4.2.0]octan-7-one;

(3'S,1R,2R,3S,6S)-2-(3'-t-butyl-dimethylsilyloxy-3'-cyclohexylprop-1'-ynyl)-3-t-butyldimethylsilyloxy-6-methoxy-8-n-butylbicyclo[4.2.0]octan-7-one;

(3'R,1R,2R,3S,6S)-2-(3'-t-butyl-dimethylsilyloxy-3'-cyclohexylprop-1'-ynyl)-3-t-butyldimethylsilyloxy-6-n-butoxy-8-n-butylbicyclo[4.2.0]octan-7-one; and (3'S,1R,2R,3S,6S)-2-(3'-t-butyldimethylsilyloxy-3'-cyclohexylprop-1'-ynyl)-3-t-butyldimethylsilyloxy-6-n-butoxy-8-n-butylbicyclo[4.2.0]octan-7-one.

PREPARATION 21

A. Preparation of (3'S,1S,2R,3S,6S)-2-(3'-tert-butyldimethylsilyloxy-3'-cyclohexylprop-1'-ynyl)-3-tert-butyldimethylsilyloxy-6-methoxy-7-hydroxy-7-vinylbicyclo[4.2.0]octane and related compounds of formula (XXXV) and (XXXVI)

A soluton of 350 mg of (3'S,1S,2R,3S,6S)-2-(3'-tert-butyldimethylsilyloxy-3'-cyclohexylprop-1'-ynyl)-3-tert-butyldimethylsilyoxy-6-methoxybicyclo[4.2.0]octan-7-one, prepared as described in Preparation 20, in 1.5 ml of dry tetrahydrofuran under nitrogen is cooled to −78° C. and 650 μl of 1M vinyl magnesium bromide in tetrahydrofuran is added dropwise. The mixture is stirred for 1 hour at −78° C. and the reaction quenched by addition of saturated aqueous ammonium chloride solution. The mixture is extracted with ethyl acetate, the extract dried over sodium sulfate, and solvent removed under reduced pressure. The resulting residue is chromatographed on silica gel to give (3'S,1S,2R,3S,6S)-2-(3'-tert-butyldimethylsilyloxy-3'-cyclohexylprop-1'-ynyl)-3-tert-butyldimethylsilyoxy-6-methoxy-7-hydroxy-7-vinylbicyclo[4.2.0]octane.

Similarly, starting with the appropriate compounds of formula (XXXIII) or (XXXIV), prepared as described in Preparation 20, any compound of formula (XXXV) or (XXXVI) where Y is H, or exo or endo-(lower alkyl) is prepared, for example:

(3'S,1R,2S,3R,6R)-2-(3'-tert-butyldimethylsilyloxy-3'-cyclohexylprop-1'-ynyl)-3-tert-butyldimethyl-silyloxy-6-methoxy-7-hydroxy-7-vinylbicyclo[4.2.0]octane.

(3'R,1S,2R,3S,6S)-2-(3'-tert-butyldimethylsilyloxy-4'-phenoxybut-1'-ynyl)-3-tert-butyldimethylsilyloxy-6-methoxy-7-hydroxy-7-vinylbicyclo[4.2.0]octane.

(3'R,1R,2S,3R,6R)-2-(3'-tert-butyldimethylsilyloxy-4'-phenoxybut-1'-ynyl)-3-tert-butyldimethylsilyloxy-6-methoxy-7-hydroxy-7-vinylbicyclo[4.2.0]octane.

(3'S,1S,2R,3S,6S)-2-(3'-tert-butyldimethylsilyloxy-4'-(endo-bicyclo[3.1.0]hex-6-yl)but-1'-ynyl)-3-tert-butyldimethylsilyloxy-6-methoxy-7-hydroxy-7-vinylbicyclo[4.2.0]octane.

(3'S,1R,2S,3R,6R)-2-(3'-tert-butyldimethylsilyloxy-4'-(endo-bicyclo[3.1.0]hex-6-yl)but-1'-ynyl)-3-tert-butyldimethylsilyloxy-6-methoxy-7-hydroxy-7-vinylbicyclo[4.2.0]octane.

(3'R,1R,2R,3S,6S)-2-(3'-tert-butyldimethylsilyloxy-4'-phenoxybut-1'-ynyl)-3-tert-butyldimethylsilyloxy-6-methoxy-7-hydroxy-7-vinyl-8-methylbicyclo[4.2.0]octane.

(3'R,1S,2S,3R,6R)-2-(3'-tert-butyldimethylsilyloxy-4'-phenoxybut-1'-ynyl)-3-tert-butyldimethylsilyloxy-6-methoxy-7-hydroxy-7-vinyl-8-methylbicyclo[4.2.0]octane.

(3'S,1R,2S,3R,6R)-2-(3'-t-butyldimethylsilyloxy-3'-cyclohexylprop-1'-ynyl)-3-t-butyldimethylsilyloxy-6-(2,2,2-trifluoroethoxy)-7-hydroxy-7-vinylbicyclo[4.2.0]-octan-7-one;

(3'S,1S,2R,3S,6S)-2-(3'-t-butyldimethylsilyloxy-3'-cyclohexylprop-1'-ynyl)-3-t-butyldimethylsilyloxy-6-(2,2,2-trifluoroethoxy)-7-hydroxy-7-vinylbicyclo[4.2.0]octan-7-one;

(3'S,1S,2S,3R,6R)-2-(3'-t-butyldimethylsilyloxy-3'-cyclohexylprop-1'-ynyl)-3-t-butyldimethylsilyloxy-6-methoxy-7-hydroxy-7-vinyl-8-methylbicyclo[4.2.0]octan-7-one;

(3'S,1R,2R,3S,6S)-2-(3'-t-butyldimethylsilyloxy-3'-cyclohexylprop-1'-ynyl)-3-t-butyldimethylsilyloxy-6-methoxy-7-hydroxy-7-vinyl-8-methylbicyclo[4.2.0]octan-7-one;

(3'S,1R,2S,3R,6R)-2-(3'-t-butyldimethylsilyloxy-3'-cyclohexylprop-1'-ynyl)-3-t-butyldimethylsilyloxy-6-ethoxy-7-hydroxy-7-vinylbicyclo[4.2.0]octan-7-one;

(3'S,1S,2R,3S,6S)-2-(3'-t-butyldimethylsilyloxy-3'-cyclohexylprop-1'-ynyl)-3-t-butyldimethylsilyloxy-6-ethoxy-7-hydroxy-7-vinylbicyclo[4.2.0]octan-7-one;

(3'S,1R,2S,3R,6R)-2-(3'-t-butyldimethylsilyloxy-3'-cyclohexylprop-1'-ynyl)-3-t-butyldimethylsilyloxy-6-n-butoxy-7-hydroxy-7-vinylbicyclo[4.2.0]octan-7-one;

(3'S,1S,2R,3S,6S)-2-(3'-t-butyldimethylsilyloxy-3'-cyclohexylprop-1'-ynyl)-3-t-butyldimethylsilyloxy-6-n-butoxy-7-hydroxy-7-vinylbicyclo[4.2.0]octan-7-one;

(3'S,1S,2S,3R,6R)-2-(3'-t-butyldimethylsilyloxy-3'-cyclohexylprop-1'-ynyl)-3-t-butyldimethylsilyloxy-6-ethoxy-7-hydroxy-7-vinyl-8-methylbicyclo[4.2.0]octan-7-one;

(3'S,1R,2R,3S,6S)-2-(3'-t-butyldimethylsilyloxy-3'-cyclohexylprop-1'-ynyl)-3-t-butyldimethylsilyloxy-6-ethoxy-7-hydroxy-7-vinyl-8-methylbicyclo[4.2.0]octan-7-one;

(3'S,1S,2S,3R,6R)-2-(3'-t-butyldimethylsilyloxy-3'-cyclohexylprop-1'-ynyl)-3-t-butyldimethylsilyloxy-6-(2,2,2-trifluoroethoxy)-7-hydroxy-7-vinyl-8-methylbicyclo[4.2.0]octan-7-one;

(3'S,1R,2R,3S,6S)-2-(3'-t-butyldimethylsilyloxy-3'-cyclohexylprop-1'-ynyl)-3-t-butyldimethylsilyloxy-6-(2,2,2-trifluoroethoxy)-7-hydroxy-7-vinyl-8-methylbicyclo[4.2.0]octan-7-one;

(3'S,1R,2S,3R,6R)-2-(3'-t-butyldimethylsilyloxy-3'-cyclopentylbut-1'-ynyl)-3-t-butyldimethylsilyloxy-6-methoxy-7-hydroxy-7-vinylbicyclo[4.2.0]octan-7-one;

(3'S,1S,2R,3S,6S)-2-(3'-t-butyldimethylsilyloxy-3'-cyclopentylbut-1'-ynyl)-3-t-butyldimethylsilyloxy-6-methoxy-7-hydroxy-7-vinylbicyclo[4.2.0]octan-7-one;

(3'S,1R,2S,3R,6R)-2-(3'-t-butyldimethylsilyloxy-3'-cyclohexylbut-1'-ynyl)-3-t-butyldimethylsilyloxy-6-methoxy-7-hydroxy-7-vinylbicyclo[4.2.0.]octan-7-one;

(3'S,1S,2R,3S,6S)-2-(3'-t-butyldimethylsilyloxy-3'-cyclohexylbut-1'-ynyl)-3-t-butyldimethylsilyloxy-6- methoxy-7-hydroxy-7-vinylbicyclo[4.2.0]octan-7-one;

(3'S,1R,2S,3R,6R)-2-(3'-t-butyldimethylsilyloxy-3'-dec-1'-ynyl)-3-hydroxy-6-methoxy-7-hydroxy-7-vinyl-bicyclo[4.2.0]octan-7-one;

(3'S,1S,2R,3S,6S)-2-(3'-t-butyldimethylsilyloxy-3'-dec-1'-ynyl)-3-hydroxy-6-methoxy-7-hydroxy-7-vinyl-bicyclo[4.2.0]octan-7-one;

(1'E)-(3'S,1S,2S,3S,6S)-2-(3'-t-butyldimethylsilyloxy-cyclohexylprop-1'-enyl)-3-t-butyldimethylsilyloxy-6-(2,2,2-trifluoroethoxy)-7-hydroxy-7-vinylbicyclo[4.2.0]octan-7-one;

(1'E)-(3'R,1S,2S,3S,6S)-2-(3'-t-butyldimethylsilyloxy-3'-cyclohexylprop-1'-enyl)-3-t-butyldimethylsilyloxy-6-(2,2,2-trifluoroethoxy)-7-hydroxy-7-vinyl-bicyclo[4.2.0]octan-7-one;

(1'E)-(3'S,1S,2S,3S,6S)-2-(3'-t-butyldimethylsilyloxy-3'-cyclohexylprop-1'-enyl)-3-t-butyldimethylsilyloxy-6-n-butoxy-7-hydroxy-7-vinylbicyclo[4.2.0]octan-7-one;

(1'E)-(3'R,1S,2S,3S,6S)-2-(3'-t-butyldimethylsilyloxy-3'-cyclohexylprop-1'-enyl)-3-t-butyldimethylsilyloxy-6-butoxy-7-hydroxy-7-vinylbicyclo[4.2.0]octan-7-one;

(1'E)-(3'S,1S,2S,3S,6S)-2-(3'-t-butyldimethylsilyloxy-4'-cyclopentylbut-1'-enyl)-3-t-butyldimethylsilyloxy-6-methoxy-7-hydroxy-7-vinylbicyclo[4.2.0]octan-7-one;

(1'E)-(3'R,1S,2S,3S,6S)-2-(3'-t-butyldimethylsilyloxy-4'-cyclopentylbut-1'-enyl)-3-t-butyldimethylsilyloxy-6-methoxy-7-hydroxy-7-vinylbicyclo[4.2.0]octan-7-one;

(1'E)-(3'S,1S,2S,3S,6S)-2-(3'-t-butyldimethylsilyloxy-4'-cyclohexylbut-1'-enyl)-3-t-butyldimethylsilyloxy-6-methoxy-7-hydroxy-7-vinylbicyclo[4.2.0]octan-7-one;

(1'E)-(3'R,1S,2S,3S,6S)-2-(3'-t-butyldimethylsilyloxy-4'-cyclohexylbut-1'-enyl)-3-t-butyldimethylsilyloxy-6-methoxy-7-hydroxy-7-vinylbicyclo[4.2.0]octan-7-one;

(1'E)-(3'S,1R,2S,3S,6S)-2-(3'-t-butyldimethylsilyloxy-3'-cyclohexylprop-1'-enyl)-3-t-butyldimethylsilyloxy-6-methoxy-7-hydroxy-7-vinyl-8-exo-methylbicyclo[4.2.0]octan-7-one;

(1'E)-(3'R,1R,2S,3S,6S)-2-(3'-t-butyldimethylsilyloxy-3'-cyclohexylprop-1'-enyl)-3-t-butyldimethylsilyloxy-6-methoxy-7-hydroxy-7-vinyl-8-exo-methylbicyclo[4.2.0]octan-7-one;

(1'E)-(3'S,1R,2S,3S,6S)-2-(3'-t-butyldimethylsilyloxy-3'-cyclohexylprop-1'-enyl)-3-t-butyldimethylsilyloxy-6-methoxy-7-hydroxy-7-vinyl-8-endo-methylbicyclo[4.2.0]octan-7-one;

(1'E)-(3'R,1R,2S,3S,6S)-2-(3'-t-butyldimethylsilyloxy-3'-cyclohexylprop-1'-enyl)-3-t-butyldimethylsilyloxy-6-methoxy-7-hydroxy-7-vinyl-8-endo-methylbicyclo[4.2.0]octan-7-one;

(1'E)-(3'S,1R,2S,3S,6S)-2-(3'-t-butyldimethylsilyloxy-3'-cyclohexylprop-1'-enyl)-3-t-butyldimethylsilyloxy-6-ethoxy-7-hydroxy-7-vinyl-8-exo-methylbicyclo[4.2.0]octan-7-one;

(3'R,1R,2R,3S,6S)-2-(3'-t-butyl-dimethylsilyloxy-3'-cyclohexylprop-1'-ynyl)-3-t-butyldimethylsilyloxy-6-methoxy-7-hydroxy-7-vinyl-8-ethylbicyclo[4.2.0]octan-7-one;

(3'S,1R,2R,3S,6S)-2-(3'-t-butyl-dimethylsilyloxy-3'-cyclohexylprop-1'-ynyl)-3-t-butyldimethylsilyloxy-6-methoxy-7-hydroxy-7-vinyl-8-ethylbicyclo[4.2.0]octan-7-one;

(3'R,1R,2R,3S,6S)-2-(3'-t-butyl-dimethylsilyloxy-3'-cyclohexylprop-1'-ynyl)-3-t-butyldimethylsilyloxy-6-methoxy-7-hydroxy-7-vinyl-8-n-butylbicyclo[4.2.0]octan-7-one;

(3'S,1R,2R,3S,6S)-2-(3'-t-butyldimethylsilyloxy-3'-cyclohexylprop-1'-ynyl)-3-t-butyldimethylsilyloxy-6-methoxy-7-hydroxy-7-vinyl-8-n-butylbicyclo[4.2.0]octan-7-one;

(3'R,1R,2R,3S,6S)-2-(3'-t-butyl-dimethylsilyloxy-3'-cyclohexylprop-1'-ynyl)-3-t-butyldimethylsilyloxy-6-n-butoxy-7-hydroxy-7-vinyl-8-n-butylbicyclo[4.2.0]octan-7-one;

(3'S,1R,2R,3S,6S)-2-(3'-t-butyl-dimethylsilyloxy-3'-cyclohexylprop-1'-ynyl)-3-t-butyldimethylsilyloxy-6-n-butoxy-7-hydroxy-7-vinyl-8-n-butylbicyclo[4.2.0]octan-7-one;

PREPARATION 22

Preparation of (1S,6R)-8,8-dichlorobicyclo[4.2.0]oct-2-en-7-one and (1R,6S,7S)-8,8-dichlorobicyclo[4.2.0]oct-2-en-7-ol, the compounds of formula (XXXIX) and (XL)A A mixture of 3 liters of water, 150 g of an active Bakers Yeast, 15 g of edible yeast and 10 g of sucrose were stirred at 33° C. A solution of 24 g of 8,8-dichlorobicyclo[4.2.0]oct-2-en-7-one in 170 ml of ethanol was added dropwise over a 15 minute period, followed by a further 5 g of sucrose. After stirring for 45 minutes the reaction mixture was centrifuged to remove the yeast, which was washed with acetone and the washings combined with the aqueous product from the centrifuge. The combined solution was washed several times with ethyl acetate, the organic washings combined and refiltered, and solvent removed from the filtrate under reduced pressure. The residue was chromatographed on silica gel, eluting with 5% acetone in hexane, initially and gradually increasing the proportion of acetone to 100%, giving 4.0 g of (1S,6R)-8,8-dichlorobicyclo[4.2.0]oct-2-en-7-one (XXXIX) as a liquid, $[\alpha]_D = -78.7°$ (C=0.8, CHCl$_3$), and 8.8 g of crude (1R,6S,7S)-8,8-dichlorobicyclo[4.2.0]oct-2-en-7-ol, which was recrystallized from hexane to give 6.4 g of pure (XL), m.p.=86°-7° C., $[\alpha]_D = -217.1°$ (C=0.5, CHCl$_3$).

In an alternative work-up procedure to that shown above, an equal volume of acetone was added to the fermentation broth, the solid filtered off through celite, the celite washed with acetone and solvent removed from the filtrate under reduced pressure. The residue was then chromatographed and purified as shown above.

PREPARATION 23

Preparation of (1S,6R,7R)-8,8-dichlorobicyclo[4.2.0]oct-2-en-7-ol, the compound of formula (XLI)

A solution of 3.0 g of (1S,6R)-8,8-dichlorobicyclo[4.2.0]oct-2-en-7-one, the compound of formula (XXXIX), prepared as shown in Preparation 22, is dissolved in 120 ml of methanol and treated at 0° C. with 1.2 g of sodium borohydride, and the mixture is stirred at 25° C. for 1 hour. The solvent is removed under reduced pressure and the residue partitioned between methylene chloride and water. The extract is dried over anhydrous sodium sulfate, filtered and the solvent removed under reduced pressure. The residue is recrystallized from hexane to give (1S,6R,7R)-8,8-dichlorobicyclo[4.2.0]oct-2-en-7-ol, $[\alpha]_D = +214.4°$, (C=0.5, CHCl₃).

PREPARATION 24

A. Preparation of (1R,6S)-8,8-dichlorobicyclo[4.2.0]oct-2-en-7-one, the compound of formula (XLII)

A. A mixture of 3.9 g of (1R,6S,7S)-8,8-dichlorobicyclo[4.2.0]oct-2-en-7-ol, prepared as shown in Preparation 22, 9.0 g of pyridinium chlorochromate and 14 g of magnesium sulfate in 200 ml of methylene chloride under nitrogen was refluxed for 4 hours. The mixture was cooled and filtered through celite, then Florisil. Solvent was removed from the eluate under reduced pressure and the residue distilled under vacuum to give 3.1 g of (1R,6S)-8,8-dichlorobicyclo[4.2.0]oct-2-en-7-one, $[\alpha]_D = +71.4°$ C., (C=0.7, CHCl₃).

B. Similarly, starting from (1S,6R,7R)-8,8-dichlorobicyclo[4.2.0]oct-2-en-7-ol, prepared as shown in Preparation 23, and following the procedure of Paragraph 24.A. above, (1S,6R)-8,8-dichlorobicyclo[4.2.0]oct-2-en-7-one is prepared, the compound of formula (XXXIX).

PREPARATION 25

A. Preparation of 3-hydroxy-4-methyloct-1,6-diyne (a) To a solution of 2.4 g of lithium aluminum hydride in 200 ml of diethyl ether at 10° C. under nitrogen was added dropwise a solution of 12.5 g of ethyl 1-methylhex-3-ynoate in 100 ml of diethyl ether. After 1 hour at between −10° C. and 0° C., 2.5 ml of water was slowly added at 0° C., followed by 2.5 ml of 15% aqueous sodium hydroxide and 8 ml of water. The mixture was filtered and the precipitate washed with ether. The organic solution was washed with brine, dried over anhydrous sodium sulfate and the solvent removed under reduced pressure to give 9.1 g of 1-hydroxy-2-methylhex-4-yne.

(b) A mixture of 9 g of 1-hydroxy-2-methylhex-4-yne, 29.5 g of pyridinium chlorochromate and 16.45 g of magnesium sulfate in 200 ml of methylene chloride under nitrogen was refluxed for 3 hours. The mixture was cooled 100 ml of diethyl ether added and the mixture filtered through Florisil. Solvent was removed from the eluate under reduced pressure to give 9 g of 1-oxo-2-methylhex-4-yne.

(c) To a solution of 50 ml of 2M ethylmagnesium bromide in tetrahydrofuran at 0° C. was added a solution of 1-oxo-2-methylhex-4-yne in 20 ml of tetrahydrofuran. The mixture was stirred for 1½ hour at 0° C., poured into saturated ammonium chloride solution, and extracted three times with diethyl ether. The combined extracts were washed with brine, dried over anhydrous sodium sulfate and solvent removed under reduced pressure. The residue was chromatographed on silica gel, eluting with 20% ethyl acetate in hexane, to give 6.0 g of 3-hydroxy-4-methyloct-1,6-diyne, the compound of formula (LXV).

B. Similarly, starting with ethyl 1-methylhept-3-ynoate and following the procedures of Preparation 25.A., 3-hydroxy-4-methylnon-1,6-diyne is prepared.

C. Similarly, starting with ethyl 1,4-dimethylhex-3-enoate and following the procedures of Preparation 25.A., 3-hydroxy-5,8-dimethylnon-1-yn-7-ene is prepared.

EXAMPLE 1

Preparation of (Z)-(3′S,1S,2R,3S,SR)-4-[2-(3′-hydroxy-3′-cyclohexylprop-1′-ynyl)-3-hydroxy-6-methoxybicyclo[4.2.0]oct-7-ylidene]butanoic acid and (E)-(3′S,1S,2R,3S,SR)-4-[2-(3′-hydroxy-3′-cyclohexylprop-1′-ynyl)-3-hydroxy-6-methoxybicyclo[4.2.0]oct-7-ylidene]butanoic acid and Related Compounds of Formulas (1), (2) and (3) in which R₁ is —CO₂H A. A stock solution of dimsyl sodium was prepared by dissolving 1.44 g sodium hydride in 30 ml dimethyl sulfoxide at 65° C. under nitrogen. To a stirred slurry of 6.97 g of 3-carboxypropyltriphenylphosphonium bromide in 25 ml dimethyl sulfoxide under nitrogen was added 15 ml of the stock solution of dimsyl sodium. After 20 min at 23° C. a solution of 995 mg of (3′S,1S,2R,3S,6S)-2-(3′-hydroxy-3′-cyclohexylprop-1′-ynyl)-3-hydroxy-6-methoxybicyclo[4.2.0]octane-7-one in 4 ml of dimethyl sulfoxide was added in one portion. After 5 h at 60° c. the mixture was poured onto 75 ml 5% sodium carbonate solution. This mixture was washed with two 60 ml portions of ethyl acetate and was then acidified with conc. HCl. The aqueous layer was extracted three times with 50 ml portions of diethyl ether. The combined ether extract was concentrated to 20 ml and this was kept at −20° C. for 2 h. The resulting precipitate was filtered and was discarded. Evaporation of the filtrate gave 1.73 mg of an oil. This material was purified by silica gel flash chromatography using a solvent mixture of acetic acid-ethyl acetate-hexane (0.25:75:25) to give 337 mg of an oil. Further purification by silica gel flash chromatography using a solvent mixture of acetic acid-methanol-dichloromethane (0.2:5.3:94.5) separated the product mixture into the individual (E) and (Z) isomers of formula 1.

The first eluted was:
(E)-(3′S,1S,2R,3S,6S)-4-[2-(3′-hydroxy-3′-cyclohexylprop-1′-ynyl)-3-hydroxy-6-methoxybicyclo[4.2.0]oct-7-ylidene]butanoic acid, 48 mg. CIMS m/z 394(M+NH₄⁺)

The second eluted was:
(Z)-(3′S,1S,2R,3S,6S)-4-[2-(3′-hydroxy-3′-cyclohexylprop-1′-ynyl)-3-hydroxy-6-methoxybicyclo[4.2.0]oct-7-ylidene]butanoic acid, 360 mg. CIMS m/z 394(M+NH₄⁺)

B. In like manner, following the procedure of Example 1.A. above, but replacing the (3′S,1S,2R,3S,6S)-2-(3′-hydroxy-3′-cyclohexylprop-1′-ynyl)-3-hydroxy-6-methoxybicyclo[4.2.0]-octane-7-one with other appropriate compounds of formula (XIV), (XV), (LVI) or (LVII), obtained as described in Preparations 14, 17 and 18, the following compounds of formulas (1), (2) or (3) were obtained:

(E)-(3′S,1R,2S,3R,6R)-4-[2-(3′-hydroxy-3′-cyclohexylprop-1′-ynyl)-3-hydroxy-6-methoxybicyclo[4.2.0]oct-7-ylidene]butanoic acid. CIMS m/z 394(M+NH₄⁺)

(Z)-(3′S,1R,2S,3R,6R)-4-[2-(3′-hydroxy-3′-cyclohexylprop-1′-ynyl)-3-hydroxy-6-methoxybicyclo[4.2.0]oct-7-ylidene]butanoic acid. CIMS m/z 394(M+NH₄⁺)

(E)-(3′S,1S,2R,3S,6S)-4-[2-(3′-hydroxy-3′-cyclohexylprop-1′-ynyl)-3-hydroxy-6-(2,2,2-trifluoroethoxy)-bicyclo[4.2.0]oct-7-ylidene]butanoic acid. CIMS m/z 462(M+NH₄⁺)

(Z)-(3'S,1S,2R,3S,6S)-4-[2-(3'-hydroxy-3'-cyclohexyl-prop-1'-ynyl)-3-hydroxy-6-(2,2,2-trifluoroethoxy)-bicyclo[4.2.0]oct-7-ylidene]butanoic acid. CIMS m/z 462(M+NH₄⁺)

(Z)-(3'S,1R,2S,3R,6R)-4-[2-(3'-hydroxy-3'-cyclohexyl-prop-1'-ynyl)-3-hydroxy-6-methoxy-8-endo-methyl-bicyclo[4.2.0]oct-7-ylidene]butanoic acid; 1H NMR (CDCl₃) δ=5.22 (td, 1, J=1.5, 7.0), δ=4.14 (dd, 1, J=1.7, 6.0), δ=3.88 (ddd, 1, J=6.8, 6.8, 6.8), δ=3.25(S, 3), δ=0.95-2.6(M, 21), δ=1.14(d, 3, J=6.7)

(Z)-(3'S,1S,2R,3S,6S)-4-[2-(3'-hydroxy-3'-cyclohexyl-prop-1'-ynyl)-3-hydroxy-6-methoxy-8-endo-methyl-bicyclo[4.2.0]oct-7-ylidene]butanoic acid; 1H NMR (CDCl₃) δ=5.22 (td, 1, J=1.5, 7.0), δ=4.16 (dd, 1, J=1.6, 5.9), δ=3.25(S, 3), δ=3.89 (ddd, 1, J=7.0, 7.0, 7.0), δ=0.95-2.6 (M, 21), δ=1.14 (d, 3, J=6.8)

(Z)-(3'SR,1RS,2SR,3RS,6RS)-4-[2-(3'-hydroxy-3'-cyclohexylprop-1'-ynyl)-3,6-dihydroxybicyclo[4.2.0]oct-7-ylidene]butanoic acid. CIMS m/z 326(M—2H₂O)

(Z)-(3'S,1S,2S,3S,6S)-4-[2-(3'-hydroxy-3'-cyclohexyl-prop-(1'E)-enyl)-3-hydroxy-6-methoxybicyclo[4.2.0]oct-7-ylidene]butanoic acid. CIMS m/z 396(M+NH₄⁺)

(E)-(3'S,1S,2S,3S,6S)-4-[2-(3'-hydroxy-3'-cyclohexyl-prop-(1'E)-enyl)-3-hydroxy-6-methoxybicyclo[4.2.0]oct-7-ylidene]butanoic acid. CIMS m/z 396(M+NH₄⁺)

(E)-(3'S,1R,2R,3R,6R)-4-[2-(3'-hydroxy-3'-cyclohexyl-prop-(1'E)-enyl)-3-hydroxy-6-methoxybicyclo[4.2.0]oct-7-ylidene]butanoic acid. CIMS m/z 396(M+NH₄⁺)

(Z)-(3'S,1R,2R,3R,6R)-4-[2-(3'-hydroxy-3'-cyclohexyl-prop-(1'E)-enyl)-3-hydroxy-6-methoxybicyclo[4.2.0]oct-7-ylidene]butanoic acid. CIMS m/z 396(M+NH₄⁺)

(E)-(3'R,1S,2S,3S,6S)-4-[2-(3'-hydroxy-3'-cyclohexyl-prop-(1'E)-enyl)-3-hydroxy-6-methoxybicyclo[4.2.0]oct-7-ylidene]pentanoic acid. CIMS m/z 396(M+NH₄⁺)

(Z)-(3'R,1S,2S,3S,6S)-4-[2-(3'-hydroxy-3'-cyclohexyl-prop-(1'E)-enyl)-3-hydroxy-6-methoxybicyclo[4.2.0]oct-7-ylidene]pentanoic acid. CIMS m/z 396(M+NH₄⁺)

C. In like manner, replacing 3-carboxypropyltriphosphonium bromide with 4-carboxybutyltriphenylphosphonium bromide, the following compounds were prepared:

(Z)-(3'S,1S,2R,3S,6S)-5-[2-(3'-hydroxy-3'-cyclohexyl-prop-1'-ynyl)-3-hydroxy-6-methoxybicyclo[4.2.0]oct-7-ylidene]pentanoic acid. CIMS m/z 408(M+NH₄⁺)

(Z)-(3'S,1R,2S,3R,6R)-5-[2-(3'-hydroxy-3'-cyclohexyl-prop-1'-ynyl)-3-hydroxy-6-methoxybicyclo[4.2.0]oct-7-ylidene]pentanoic acid. CIMS m/z 408(M+NH₄⁺)

(Z)-(3'S,1S,2R,3S,6S)-5-[2-(3'-hydroxy-3'-cyclohexyl-prop-1'-ynyl)-3-hydroxy-6-methoxy-8-endo-methyl-bicyclo[4.2.0]oct-7-ylidene]pentanoic acid; 1H NMR (CDCl₃) δ=5.18 (td, 1, J=1.5, 7.0), δ=4.17 (dd, 1, J=1.65, 5.85), δ=3.88 (ddd, 1, J=7.0, 7.0, 7.0), δ=3.25(s, 3), δ=0.95-2.6 (m, 21), δ=1.14 (d, 3, J=6.7)

(Z)-(3'S,1S,2S,3S,6S)-5-[2-(3'-hydroxy-3'-cyclohexyl-prop-(1'E)-enyl)-3-hydroxy-6-methoxybicyclo[4.2.0]oct-7-ylidene]pentanoic acid. CIMS m/z 374(M—H₂O)

(Z)-(3'R,1S,2S,3S,6S)-5-[2-(3'-hydroxy-3'-cyclohexyl-prop-(1'E)-enyl)-3-hydroxy-6-methoxybicyclo[4.2.0]oct-7-ylidene]pentanoic acid. CIMS m/z 374(M—H₂O)

D. Similarly, the (E) and (Z) isomers of the following exemplary compounds of formula (1), (2) and (3), where Y is H, or exo or endo-(lower alkyl), are made:

(3'S,1R,2S,3R,6R)-4-[2-(3'-hydroxy-3'-cyclohexylprop-1'-ynyl)-3-hydroxy-6-methoxy-8-exo-methylbicyclo[4.2.0]oct-7-ylidene]butanoic acid;

(E)-(3'S,1R,2S,3R,6R)-4-[2-(3'-hydroxy-3'-cyclohexyl-prop-1'-ynyl)-3-hydroxy-6-methoxy-8-endo-methyl-bicyclo[4.2.0]oct-7-yidene]butanoic acid. CIMS m/z 394(M+NH)

(3'S,1R,2S,3R,6R)-4-[2-(3'-hydroxy-3'-cyclohexylprop-1'-ynyl)-3,6-dihydroxybicyclo[4.2.0]oct-7-ylidene]butanoic acid;

(3'S,1S,2S,3S,6S)-4-[2-(3'-hydroxy-3'-cyclohexylprop-(1'E)-enyl)-3-hydroxy-6-methoxybicyclo[4.2.0]oct-7-ylidene]butanoic acid;

(3'S,1S,2R,3S,6S)-5-[2-(3'-hydroxy-3'-cyclohexylprop-1'-ynyl)-3-hydroxy-6-methoxybicyclo[4.2.0]oct-7-ylidene]pentanoic acid;

(3'S,1R,2S,3R,6R)-5-[2-(3'-hydroxy-3'-cyclohexylprop-1'-ynyl)-3-hydroxy-6-methoxybicyclo[4.2.0]oct-7-ylidene]pentanoic acid;

(3'S,1R,2S,3R,6R)-4-[2-(3'-hydroxy-3'-cyclohexylprop-1'-ynyl)-3-hydroxy-6-ethoxybicyclo[4.2.0]oct-7-ylidene]butyric acid;

(3'S,1S,2R,3S,6S)-4-[2-(3'-hydroxy-3'-cyclohexylprop-1'-ynyl)-3-hydroxy-6-ethoxybicyclo[4.2.0]oct-7-ylidene]butyric acid;

(3'R,1R,2S,3R,6R)-4-[2-(3'-hydroxy-4'-phenoxybut-1'-ynyl)-3-hydroxy-6-methoxybicyclo[4.2.0]oct-7-ylidene]butyric acid;

(3'R,1S,2R,3S,6S)-4-[2-(3'-hydroxy-4'-phenoxybut-1'-ynyl)-3-hydroxy-6-methoxybicyclo[4.2.0]oct-7-ylidene]butyric acid;

(3'S,1R,2S,3R,6R)-4-[2-(3'-hydroxy-4'-(endo-bicyclo[3.1.0]hex-6-yl)but-1'-ynyl)-3-hydroxy-6-methoxybicyclo[4.2.0]oct-7-ylidene]butyric acid;

(3'S,1S,2R,3S,6S)-4-[2-(3'-hydroxy-4'-(endo-bicyclo[3.1.0]hex-6-yl)but-1'-ynyl)-3-hydroxy-6-methoxybicyclo[4.2.0]oct-7-ylidene]butyric acid;

(3'R,1R,2S,3R,6R)-4-[2-(3'-hydroxy-4'-phenoxybut-1'-ynyl)-3-hydroxy-6-methoxy-8-methylbicyclo[4.2.0]oct-7-ylidene]butyric acid;

(3'R,1S,2R,3S,6S)-4-[2-(3'-hydroxy-4'-phenoxybut-1'-ynyl)-3-hydroxy-6-methoxy-8-methylbicyclo[4.2.0]oct-7-ylidene]butyric acid;

(3'S,1R,2R,3R,6R)-4-[2-(3'-hydroxy-5',9'-dimethyldec-1',8'-dien-(1'E)-yl)-3-hydroxy-6-methoxybicyclo[4.2.0]oct-7-ylidene]butyric acid;

(3'S,1S,2R,3S,6S)-4-[2-(3'-hydroxy-5',9'-dimethyldec-1',8'-dien-(1'E)-yl)-3-hydroxy-6-methoxybicyclo[4.2.0]oct-7-ylidene]butyric acid;

(3'S,1R,2S,3R,6R)-4-[2-(3'-hydroxy-3'-cyclohexylprop-1'-ynyl)-3-hydroxy-6-n-butoxybicyclo[4.2.0]oct-7-ylidene]butyric acid;

(3'S,1S,2R,3S,6S)-4-[2-(3'-hydroxy-3'-cyclohexylprop-1'-ynyl)-3-hydroxy-6-n-butoxybicyclo[4.2.0]oct-7-ylidene]butyric acid;

(3'S,1R,2S,3R,6R)-4-[2-(3'-hydroxy-4'-cyclopentylbut-1'-ynyl)-3-hydroxy-6-methoxybicyclo[4.2.0]oct-7-ylidene]butyric acid;

(3'S,1S,2R,3S,6S)-4-[2-(3'-hydroxy-4'-cyclopentylbut-1'-ynyl)-3-hydroxy-6-methoxybicyclo[4.2.0]oct-7-ylidene]butyric acid;

(3′S,1R,2S,3R,6R)-4-[2-(3′-hydroxy-4′-cyclohexylbut-1′-ynyl)-3-hydroxy-6-methoxybicyclo[4.2.0]oct-7-ylidene]butyric acid;

(3′S,1S,2R,3S,6S)-4-[2-(3′-hydroxy-4′-cyclohexylbut-1′-ynyl)-3-hydroxy-6-methoxybicyclo[4.2.0]oct-7-ylidene]butyric acid;

(3′S,1R,2S,3R,6R)-4-[2-(3′-hydroxy-dec-1′-ynyl)-3-hydroxy-6-methoxybicyclo[4.2.0]oct-7-ylidene]butyric acid;

(3′S,1S,2R,3S,6S)-4-[2-(3′-hydroxy-dec-1′-ynyl)-3-hydroxy-6-methoxybicyclo[4.2.0]oct-7-ylidene]butyric acid;

(3′S,1R,2S,3R,6R)-4-[2-(3′-hydroxy-4′-cyclopentylbut-1′-ynyl)-3-hydroxy-6-methoxy-8-exo-methylbicyclo[4.2.0]-oct-7-ylidene]butyric acid;

(3′S,1S,2R,3S,6S)-4-[2-(3′-hydroxy-4′-cyclopentylbut-1′-ynyl)-3-hydroxy-6-methoxy-8-exo-methylbicyclo[4.2.0]oct-7-ylidene]butyric acid;

(3′S,1S,2R,3S,6S)-4-[2-(3′-hydroxy-3′-cyclohexylprop-1′-ynyl)-3-hydroxy-6-methoxy-8-ethylbicyclo[4.2.0]oct-7-ylidene]butyric acid;

(3′S,1R,2S,3R,6R)-4-[2-(3′-hydroxy-3′-cyclohexylprop-1′-ynyl)-3-hydroxy-6-methoxy-8-ethylbicyclo[4.2.0]oct-7-ylidene]butyric acid;

(3′S,1S,2R,3S,6S)-4-[2-(3′-hydroxy-3′-cyclohexylprop-1′-ynyl)-3-hydroxy-6-methoxy-8-n-butylbicyclo[4.2.0]oct-7-ylidene]butyric acid;

(3′S,1R,2S,3R,6R)-4-[2-(3′-hydroxy-3′-cyclohexylprop-1′-ynyl)-3-hydroxy-6-methoxy-8-n-butylbicyclo[4.2.0]oct-7-ylidene]butyric acid;

(3′S,1S,2R,3S,6S)-4-[2-(3′-hydroxy-3′-cyclohexylprop-1′-ynyl)-3-hydroxy-6-n-butoxy-8-n-butylbicyclo[4.2.0]oct-7-ylidene]butyric acid;

(3′S,1R,2S,3R,6R)-4-[2-(3′-hydroxy-3′-cyclohexylprop-1′-ynyl)-3-hydroxy-6-n-butoxy-8-n-butylbicyclo[4.2.0]oct-7-ylidene]butyric acid;

(3′S,1R,2S,3R,6R)-5-[2-(3′-hydroxy-3′-cyclohexylprop-1′-ynyl)-3-hydroxy-6-methoxy-8-exo-methylbicyclo[4.2.0]oct-7-ylidene]pentanoic acid;

(3′S,1R,2S,3R,6R)-5-[2-(3′-hydroxy-3′-cyclohexylprop-1′-ynyl)-3-hydroxy-6-methoxy-8-endo-methylbicyclo[4.2.0]oct-7-ylidene]pentanoic acid;

(3′S,1S,2R,3S,6S)-5-[2-(3′-hydroxy-3′-cyclohexylprop-1′-ynyl)-3-hydroxy-6-ethoxybicyclo[4.2.0]oct-7-ylidene]pentanoic acid;

(3′S,1S,2R,3S,6S)-5-[2-(3′-hydroxy-3′-cyclohexylprop-1′-ynyl)-3-hydroxy-6-n-butoxybicyclo[4.2.0]oct-7-ylidene]pentanoic acid;

(3′S,1R,2S,3R,6R)-5-[2-(3′-hydroxy-dec-1′-ynyl)-3-hydroxy-6-methoxybicyclo[4.2.0]oct-7-ylidene]pentanoic acid;

(3′R,1S,2S,3S,6S)-4-[2-(3′-hydroxy-3′-cyclohexylprop-(1′E)-enyl)-3-hydroxy-6-ethoxybicyclo[4.2.0]oct-7-ylidene]butyric acid;

(3′S,1S,2S,3S,6S)-4-[2-(3′-hydroxy-3′-cyclohexylprop-(1′E)-enyl)-3-hydroxy-6-ethoxybicyclo[4.2.0]oct-7-ylidene]butyric acid;

(3′R,1S,2S,3S,6S)-4-[2-(3′-hydroxy-3′-cyclohexylprop-(1′E)-enyl)-3-hydroxy-6-trifluoroethoxybicyclo[4.2.0]oct-7-ylidene]butyric acid;

(3′S,1S,2S,3S,6S)-4-[2-(3′-hydroxy-3′-cyclohexylprop-(1′E)-enyl)-3-hydroxy-6-trifluoroethoxybicyclo[4.2.0]oct-7-ylidene]butyric acid;

(3′R,1S,2S,3S,6S)-4-[2-(3′-hydroxy-3′-cyclohexylprop-(1′E)-enyl)-3-hydroxy-6-n-butoxybicyclo[4.2.0]oct-7-ylidene]butyric acid;

(3′S,1S,2S,3S,6S)-4-[2-(3′-hydroxy-3′-cyclohexylprop-(1′E)-enyl)-3-hydroxy-6-n-butoxybicyclo[4.2.0]oct-7-ylidene]butyric acid;

(3′R,1S,2S,3S,6S)-4-[2-(3′-hydroxy-3′-cyclohexylprop-(1′E)-enyl)-3-hydroxy-6-methoxy-8-exo-methylbicyclo[4.2.0]oct-7-ylidene]butyric acid;

(3′S,1S,2S,3S,6S)-4-[2-(3′-hydroxy-3′-cyclohexylprop-(1′E)-enyl)-3-hydroxy-6-methoxy-8-exo-methylbicyclo[4.2.0]oct-7-ylidene]butyric acid;

(3′R,1S,2S,3S,6S)-4-[2-(3′-hydroxy-3′-cyclohexylprop-(1′E)-enyl)-3-hydroxy-6-methoxy-8-endomethylbicyclo[4.2.0]oct-7-ylidene]butyric acid;

(3′S,1S,2S,3S,6S)-4-[2-(3′-hydroxy-3′-cyclohexylprop-(1′E)-enyl)-3-hydroxy-6-methoxy-8-endo-methylbicyclo[4.2.0]oct-7-ylidene]butyric acid;

(3′R,1S,2S,3S,6S)-4-[2-(3′-hydroxy-3′-dec-(1′E)-enyl)-3-hydroxy-6-methoxybicyclo[4.2.0]oct-7-ylidene]butyric acid;

(3′S,1S,2S,3S,6S)-4-[2-(3′-hydroxy-3′-dec-(1′E)-enyl)-3-hydroxy-6-methoxybicyclo[4.2.0]oct-7-ylidene]butyric acid;

(3′R,1S,2S,3S,6S)-4-[2-(3′-hydroxy-3′-cyclopentylprop-(1′E)-enyl)-3-hydroxy-6-methoxybicyclo[4.2.0]oct-7-ylidene]butyric acid;

(3′S,1S,2S,3S,6S)-4-[2-(3′-hydroxy-3′-cyclopentylprop-(1′E)-enyl)-3-hydroxy-6-methoxybicyclo[4.2.0]oct-7-ylidene]butyric acid;

(3′R,1S,2S,3S,6S)-5-[2-(3′-hydroxy-3′-cyclopentylprop-(1′E)-enyl)-3-hydroxy-6-methoxybicyclo[4.2.0]oct-7-ylidene]pentanoic acid;

(3′S,1S,2S,3S,6S)-5-[2-(3′-hydroxy-3′-cyclopentylprop-(1′E)-enyl)-3-hydroxy-6-methoxybicyclo[4.2.0]oct-7-ylidene]pentanoic acid;

(3′R,1S,2S,3S,6S)-5-[2-(3′-hydroxy-3′-cyclopentylprop-(1′E)-enyl)-3-hydroxy-6-methoxy-8-exomethylbicyclo[4.2.0]oct-7-ylidene]pentanoic acid;

(3′S,1S,2S,3S,6S)-5-[2-(3′-hydroxy-3′-cyclopentylprop-(1′E)-enyl)-3-hydroxy-6-methoxy-8-exomethylbicyclo[4.2.0]oct-7-ylidene]pentanoic acid;

(3′R,1S,2S,3S,6S)-5-[2-(3′-hydroxy-3′-cyclopentylprop-(1′E)-enyl)-3-hydroxy-6-methoxy-8-endomethylbicyclo[4.2.0]oct-7-ylidene]pentanoic acid;

(3′S,1S,2S,3S,6S)-5-[2-(3′-hydroxy-3′-cyclopentylprop-(1′E)-enyl)-3-hydroxy-6-methoxy-8-endomethylbicyclo[4.2.0]oct-7-ylidene]pentanoic acid;

(3′R,1S,2S,3S,6S)-5-[2-(3′-hydroxy-3′-cyclopentylprop-(1′E)-enyl)-3-hydroxy-6-n-butoxybicyclo[4.2.0]-oct-7-ylidene]pentanoic acid;

(3′S,1S,2S,3S,6S)-5-[2-(3′-hydroxy-3′-cyclopentylprop-(1′E)-enyl-3-hydroxy-6-n-butoxybicyclo[4.2.0]oct-7-ylidene]pentanoic acid;

(3′R,1S,2S,3S,6S)-6-[2-(3′-hydroxy-3′-cyclohexylprop-(1′E)-enyl)-3-hydroxy-6-methoxybicyclo[4.2.0]oct-7-ylidene]hexanoic acid;

(3′R,1S,2S,3S,6S)-6-[2-(3′-hydroxy-3′-cyclohexylprop-1′-yl)-3-hydroxy-6-methoxybicyclo[4.2.0]-oct-7-ylidene]butanoic acid;

(3′R,1R,2R,3R,6R)-6-[2-(3′-hydroxy-3′-cyclohexylprop-1′-yl)-3-hydroxy-6-methoxybicyclo[4.2.0]-oct-7-ylidene]butanoic acid;

(3′R,1S,2S,3S,6S)-6-[2-(3′-hydroxy-3′-cyclohexylprop-1′-yl)-3-hydroxy-6-methoxy-8-methylbicyclo[4.2.0]oct-7-ylidene]butyric acid;

(3′R,1R,2R,3R,6R)-6-[2-(3′-hydroxy-3′-cyclohexylprop-1′-yl)-3-hydroxy-6-methoxy-8-methylbicyclo[4.2.0]oct-7-ylidene]butanoic acid;

(3'R,1S,2S,3S,6S)-6-[2-(3'-hydroxy-4'-phenoxybut-1'-yl)-3-hydroxy-6-methoxybicyclo[4.2.0]-oct-7-ylidene]butanoic acid;

(3'R,1R,2R,3R,6R)-6-[2-(3'-hydroxy-4'-phenoxybut-1'-yl)-3-hydroxy-6-methoxybicyclo[4.2.0]-oct-7-ylidene]butanoic acid;

(3'S,1R,2R,3R,6R)-4-[2-(3'-hydroxy-3'-cyclohexylprop-(1'E)-enyl)-3-hydroxy-6-ethoxybicyclo[4.2.0]oct-7-ylidene]butyric acid;

(3'S,1R,2R,3R,6R)-4-[2-(3'-hydroxy-3'-cyclohexylprop-(1'E)-enyl)-3-hydroxy-6-trifluoroethoxybicyclo[4.2.0]oct-7-ylidene]butyric acid;

(3'S,1R,2R,3R,6R)-4-[2-(3'-hydroxy-3'-cyclohexylprop-(1'E)-enyl)-3-hydroxy-6-n-butoxybicyclo[4.2.0]oct-7-ylidene]butyric acid;

(3'S,1R,2R,3R,6R)-4-[2-(3'-hydroxy-3'-cyclohexylprop-(1'E)-enyl)-3-hydroxy-6-methoxy-8-exomethylbicyclo[4.2.0]oct-7-ylidene]butyric acid;

(3'S,1R,2R,3R,6R)-4-[2-(3'-hydroxy-3'-cyclohexylprop-(1'E)-enyl)-3-hydroxy-6-methoxy-8-endo-methylbicyclo[4.2.0]oct-7-ylidene]butyric acid;

(3'S,1R,2R,3R,6R)-4-[2-(3'-hydroxy-3'-dec-(1'E)-enyl)-3-hydroxy-6-methoxybicyclo[4.2.0]oct-7-ylidene]butyric acid; and (3'S,1R,2R,3R,6R)-4-[2-(3'-hydroxy-3'cyclohexylprop-(1'E)-enyl)-3-hydroxy-6-methoxy-8-ethylbicyclo[4.2.0]oct-7-ylidene]butyric acid;

(3'R,1S,2S,3S,6S)-4-[2-(3'-hydroxy-3'cyclohexylprop-(1'E)-enyl)-3-hydroxy-6-methoxy-8-ethylbicyclo[4.2.0]oct-7-ylidene]butyric acid;

(3'S,1S,2S,3S,6S)-4-[2-(3'-hydroxy-3'cyclohexylprop-(1'E)-enyl)-3-hydroxy-6-methoxy-8-n-butylbicyclo[4.2.0]oct-7-ylidene]butyric acid;

(3'S,1R,2R,3R,6R)-4-[2-(3'-hydroxy-3'cyclohexylprop-(1'E)-enyl)-3-hydroxy-6-methoxy-8-n-butylbicyclo[4.2.0]oct-7-ylidene]butyric acid;

(3'S,1R,2R,3R,6R)-4-[2-(3'-hydroxy-3'cyclohexylprop-(1'E)-enyl)-3-hydroxy-6-n-butoxy-8-n-butylbicyclo[4.2.0]oct-7-ylidene]butyric acid; and (3'R,1S,2S,3S,6S)-4-[2-(3'-hydroxy-3'cyclohexylprop-(1'E)-enyl)-3-hydroxy-6-n-butoxy-8-n-butylbicyclo[4.2.0]oct-7-ylidene]butyric acid.

EXAMPLE 2

A. Alternative preparation of (Z)-(3'S,1S,2R,3S,6S)-4-[2-(3'-hydroxy-3'-cyclohexylprop-1'-ynyl)-3-hydroxy-6-methoxybicyclo[4.2.0]oct-7-ylidene]butanoic acid and (E)-(3'S,1S,2R,3S,6S)-4-[2-(3'-hydroxy-3'cyclohexylprop-1'-ynyl)-3-hydroxy-6-methoxybicyclo[4.2.0]oct-7-ylidene]butanoic acid and Related Compounds of Formulas (1), (2) and (3) in which $R_1$ is —$CO_2H$ (a) A solution of 100 mg of (Z)-(3'S,1S,2R,3S,6S)-4-[2-(3'-tert-butyldimethylsilyloxy-3'-cyclohexylprop-1'-ynyl)-3-tert-butyldimethylsilyloxy-6-methoxy-7-hydroxy-7-vinyl-bicyclo[4.2.0]octane, prepared as shown in Preparation 21, 5 μl of acetic acid and 0.6 ml of triethyl orthoacetate is heated at 120° C. for 20 hrs. The excess reactants are then removed under reduced pressure and the residue chromatographed on silica gel, eluting with 10% ethyl acetate in hexane to give a mixture of the (E) and (Z) isomers of ethyl (3'S,1S,2R,3S,6S)-4-[2-(3'-tert-butyldimethylsilyloxy-3'-cyclohexylprop-1'-ynyl)-3-tert-butyldimethylsilyloxy-6-methoxybicyclo[4.2.0]oct-7-ylidene]butyrate.

(b) The mixture of the (E) and (Z) isomers is dissolved in 1 ml of a mixture of 1N sulfuric acid-acetonitrile (1:1) and stirred at room temperature for 48 hours. The reaction mixture is then poured into water, extracted with ethyl acetate, the extract dried over sodium sulfate and solvent removed under reduced pressure. The residue is treated with 2 ml of 0.5M lithium hydroxide in methanol, stirring for 16 hours at room temperature. The reaction mixture is then acidified with 0.5M potassium bisulfate and extracted with ethyl acetate. The organic layer is washed with brine, dried over sodium sulfate and the solvent removed under reduced pressure. The residue is chromatographed on silica gel eluting with a mixture of acetic acid-methanoldichloromethane (0.2:5.3:94.5) to give (Z)-(3'S,1S,2R,3S,6S)-4-[2-(3'-hydroxy-3'-cyclohexylprop-1'-ynyl)-3-hydroxy-6-methoxybicyclo[4.2.0]oct-7-ylidene]butanoic acid and (E)-(3'S,1S,2R,3S,6S)-4-[2-(3'-hydroxy-3'-cyclohexylprop-1'-ynyl)-3-hydroxy-6-methoxybicyclo[4.2.0]oct-7-ylidene]butanoic acid.

B. In like manner, starting with the appropriate compounds of formula (XXXV) or (XXXVI), obtained as described in Preparation 20, the following exemplary compounds of formula (1), (2) and (3) where Y is H, or exo or endo-(lower alkyl) are obtained as (E) or (Z) isomers:

(3'S,1R,2S,3R,6R)-4-[2-(3'-hydroxy-3'-cyclohexylprop-1'-ynyl)-3-hydroxy-6-ethoxybicyclo[4.2.0]oct-7-ylidene]butyric acid;

(3'S,1S,2R,3S,6S)-4-[2-(3'-hydroxy-3'-cyclohexylprop-1'-ynyl)-3-hydroxy-6-ethoxybicyclo[4.2.0]oct-7-ylidene]butyric acid;

(3'R,1R,2S,3R,6R)-4-[2-(3'-hydroxy-4'-phenoxybut-1'-ynyl)-3-hydroxy-6-methoxybicyclo[4.2.0]oct-7-ylidene]butyric acid;

(3'R,1S,2R,3S,6S)-4-[2-(3'-hydroxy-4'-phenoxybut-1'-ynyl)-3-hydroxy-6-methoxybicyclo[4.2.0]oct-7-ylidene]butyric acid;

(3'S,1R,2S,3R,6R)-4-[2-(3'-hydroxy-5',9'-dimethyldec-1',8'-dien-(1'E)-yl)-3-hydroxy-6-methoxybicyclo[4.2.0]oct-7-ylidene]butyric acid;

(3'S,1S,2R,3S,6S)-4-[2-(3'-hydroxy-5',9'-dimethyldec-1',8'-dien-(1'E)-yl)-3-hydroxy-6-methoxybicyclo[4.2.0]oct-7-ylidene]butyric acid;

(3'S,1R,2S,3R,6R)-4-[2-(3'-hydroxy-3'-cyclohexylprop-1'-ynyl)-3-hydroxy-6-n-butoxybicyclo[4.2.0]oct-7-ylidene]butyric acid;

(3'S,1S,2R,3S,6S)-4-[2-(3'-hydroxy-3'-cyclohexylprop-1'-ynyl)-3-hydroxy-6-n-butoxybicyclo[4.2.0]oct-7-ylidene]butyric acid;

(3'S,1R,2S,3R,6R)-4-[2-(3'-hydroxy-4'-cyclopentylbut-1'-ynyl)-3-hydroxy-6-methoxybicyclo[4.2.0]oct-7-ylidene]butyric acid;

(3'S,1S,2R,3S,6S)-4-[2-(3'-hydroxy-4'-cyclopentylbut-1'-ynyl)-3-hydroxy-6-methoxybicyclo[4.2.0]oct-7-ylidene]butyric acid;

(3'S,1R,2S,3R,6R)-4-[2-(3'-hydroxy-4'-cyclohexylbut-1'-ynyl)-3-hydroxy-6-methoxybicyclo[4.2.0]oct-7-ylidene]butyric acid;

(3'S,1S,2R,3S,6S)-4-[2-(3'-hydroxy-4'-cyclohexylbut-1'-ynyl)-3-hydroxy-6-methoxybicyclo[4.2.0]oct-7-ylidene]butyric acid;

(3'S,1R,2S,3R,6R)-4-[2-(3'-hydroxydec-1'-ynyl)-3-hydroxy-6-methoxybicyclo[4.2.0]oct-7-ylidene]butyric acid;

(3'S,1S,2R,3S,6S)-4-[2-(3'-hydroxydec-1'-ynyl)-3-hydroxy-6-methoxybicyclo[4.2.0]oct-7-ylidene]butyric acid;

(3'S,1R,2S,3R,6R)-4-[2-(3'-hydroxy-4'-cyclopentylbut-1'-ynyl)-3-hydroxy-6-methoxy-8-exo-methylbicyclo[4.2.0]oct-7-ylidene]butyric acid;

(3'S,1S,2R,3S,6S)-4-[2-(3'-hydroxy-4'-cyclopentylbut-1'-ynyl)-3-hydroxy-6-methoxy-8-exo-methylbicyclo[4.2.0]oct-7-ylidene]butyric acid;

(3'S,1S,2R,3S,6S)-4-[2-(3'-hydroxy-3'-cyclohexylprop-1'-ynyl)-3-hydroxy-6-methoxy-8-ethylbicyclo[4.2.0]oct-7-ylidene]butyric acid;

(3'S,1R,2S,3R,6R)-4-[2-(3'-hydroxy-3'-cyclohexylprop-1'-ynyl)-3-hydroxy-6-methoxy-8-ethylbicyclo[4.2.0]oct-7-ylidene]butyric acid;

(3'S,1S,2R,3S,6S)-4-[2-(3'-hydroxy-3'-cyclohexylprop-1'-ynyl)-3-hydroxy-6-methoxy-8-n-butylbicyclo[4.2.0]oct-7-ylidene]butyric acid;

(3'S,1R,2S,3R,6R)-4-[2-(3'-hydroxy-3'-cyclohexylprop-1'-ynyl)-3-hydroxy-6-methoxy-8-n-butylbicyclo[4.2.0]oct-7-ylidene]butyric acid;

(3'S,1S,2R,3S,6S)-4-[2-(3'-hydroxy-3'-cyclohexylprop-1'-ynyl)-3-hydroxy-6-n-butoxy-8-n-butylbicyclo[4.2.0]oct-7-ylidene]butyric acid;

(3'S,1R,2S,3R,6R)-4-[2-(3'-hydroxy-3'-cyclohexylprop-1'-ynyl)-3-hydroxy-6-n-butoxy-8-n-butylbicyclo[4.2.0]oct-7-ylidene]butyric acid;

(3'R,1S,2S,3S,6S)-4-[2-(3'-hydroxy-3'-cyclohexylprop-(1'E)-enyl)-3-hydroxy-6-methoxy-8-exo-methylbicyclo[4.2.0]oct-7-ylidene]butyric acid;

(3'S,1S,2S,3S,6S)-4-[2-(3'-hydroxy-3'-cyclohexylprop-(1'E)-enyl)-3-hydroxy-6-methoxy-8-exo-methylbicyclo[4.2.0]oct-7-ylidene]butyric acid;

(3'R,1S,2S,3S,6S)-4-[2-(3'-hydroxy-3'-cyclohexylprop-(1'E)-enyl)-3-hydroxy-6-methoxy-8-endo-methylbicyclo[4.2.0]oct-7-ylidene]butyric acid;

(3'S,1S,2S,3S,6S)-4-[2-(3'-hydroxy-3'-cyclohexylprop-(1'E)-enyl)-3-hydroxy-6-methoxy-8-endomethylbicyclo[4.2.0]oct-7-ylidene]butyric acid;

(3'S,1R,2S,3R,6R)-4-[2-(3'-hydroxy-4'-cyclopentylbut-1'-ynyl)-3-hydroxy-6-methoxy-8-exo-methylbicyclo[4.2.0]oct-7-ylidene]butyric acid;

(3'S,1S,2R,3S,6S)-4-[2-(3'-hydroxy-4'-cyclopentylbut-1'-ynyl)-3-hydroxy-6-methoxy-8-exo-methylbicyclo[4.2.0]oct-7-ylidene]butyric acid;

(3'R,1S,2S,3S,6S)-4-[2-(3'-hydroxy-3'-cyclohexylprop-(1'E)-enyl)-3-hydroxy-6-ethoxybicyclo[4.2.0]oct-7-ylidene]butyric acid;

(3'S,1S,2S,3S,6S)-4-[2-(3'-hydroxy-3'-cyclohexylprop-(1'E)-enyl)-3-hydroxy-6-ethoxybicyclo[4.2.0]oct-7-ylidene]butyric acid;

(3'R,1S,2S,3S,6S)-4-[2-(3'-hydroxy-3'-cyclohexylprop-(1'E)-enyl)-3-hydroxy-6-trifluoroethoxybicyclo[4.2.0]oct-7-ylidene]butyric acid;

(3'S,1S,2S,3S,6S)-4-[2-(3'-hydroxy-3'-cyclohexylprop-(1'E)-enyl)-3-hydroxy-6-trifluoroethoxybicyclo[4.2.0]oct-7-ylidene]butyric acid;

(3'R,1S,2S,3S,6S)-4-[2-(3'-hydroxy-3'-cyclohexylprop-(1'E)-enyl)-3-hydroxy-6-n-butoxybicyclo[4.2.0]oct-7-ylidene]butyric acid;

(3'S,1S,2S,3S,6S)-4-[2-(3'-hydroxy-3'-cyclohexylprop-(1'E)-enyl)-3-hydroxy-6-n-butoxybicyclo[4.2.0]oct-7-ylidene]butyric acid;

(3'R,1S,2S,3S,6S)-4-[2-(3'-hydroxy-3'-cyclohexylprop-(1'E)-enyl)-3-hydroxy-6-methoxy-8-exo-methylbicyclo[4.2.0]oct-7-ylidene]butyric acid;

(3'S,1S,2S,3S,6S)-4-[2-(3'-hydroxy-3'-cyclohexylprop-(1'E)-enyl)-3-hydroxy-6-methoxy-8-exo-methylbicyclo[4.2.0]oct-7-ylidene]butyric acid;

(3'R,1S,2S,3S,6S)-4-[2-(3'-hydroxy-3'-cyclohexylprop-(1'E)-enyl)-3-hydroxy-6-methoxy-8-endo-methylbicyclo[4.2.0]oct-7-ylidene]butyric acid;

(3'S,1S,2S,3S,6S)-4-[2-(3'-hydroxy-3'-cyclohexylprop-(1'E)-enyl)-3-hydroxy-6-methoxy-8-endo-methylbicyclo[4.2.0]oct-7-ylidene]butyric acid;

(3'S,1S,2S,3S,6S)-4-[2-(3'-hydroxy-3'-cyclohexylprop-(1'E)-enyl)-3-hydroxy-6-methoxy-8-ethylbicyclo[4.2.0]oct-7-ylidene]butyric acid;

(3'R,1S,2S,3S,6S)-4-[2-(3'-hydroxy-3'-cyclohexylprop-(1'E)-enyl)-3-hydroxy-6-methoxy-8-ethylbicyclo[4.2.0]oct-7-ylidene]butyric acid;

(3'S,1S,2S,3S,6S)-4-[2-(3'-hydroxy-3'-cyclohexylprop-(1'E)-enyl)-3-hydroxy-6-methoxy-8-n-butylbicyclo[4.2.0]oct-7-ylidene]butyric acid;

(3'S,1S,2S,3S,6S)-4-[2-(3'-hydroxy-3'-cyclohexylprop-(1'E)-enyl)-3-hydroxy-6-methoxy-8-n-butylbicyclo[4.2.0]oct-7-ylidene]butyric acid;

(3'S,1S,2S,3S,6S)-4-[2-(3'-hydroxy-3'-cyclohexylprop-(1'E)-enyl)-3-hydroxy-6-n-butoxy-8-n-butylbicyclo[4.2.0]oct-7-ylidene]butyric acid; and (3'R,1S,2S,3S,6S)-4-[2-(3'-hydroxy-3'-cyclohexylprop-(1'E)-enyl)-3-hydroxy-6-n-butoxy-8-n-butylbicyclo[4.2.0]oct-7-ylidene]butyric acid.

(3'R,1S,2S,3S,6S)-4-[2-(3'-hydroxy-3'-dec-(1'E)-enyl)-3-hydroxy-6-methoxybicyclo[4.2.0]oct-7-ylidene]butyric acid;

(3'S,1R,2R,3R,6R)-4-[2-(3'-hydroxy-3'-dec-(1'E)-enyl)-3-hydroxy-6-methoxybicyclo[4.2.0]oct-7-ylidene]butyric acid.

(3'R,1S,2S,3S,6S)-4-[2-(3'-hydroxy-3'-cyclohexylprop-1'-yl)-3-hydroxy-6-methoxy-8-methylbicyclo[4.2.0]oct-7-ylidene]butyric acid;

(3'R,1S,2S,3S,6S)-6-[2-(3'-hydroxy-3'-cyclohexylprop-1'-yl)-3-hydroxy-6-methoxy-8-methylbicyclo[4.2.0]oct-7-ylidene]butyric acid;

(3'R,1S,2S,3S,6S)-4-[2-(3'-hydroxy-4'-phenoxybut-1'-yl)-3-hydroxy-6-methoxy-8-methylbicyclo[4.2.0]oct-7-ylidene]butyric acid; and (3'R,1S,2S,3S,6S)-4-[2-(3'-hydroxy-4'-phenoxybut-1'-yl)-3-hydroxy-6-methoxy-8-methylbicyclo[4.2.0]oct-7-ylidene]butyric acid;

EXAMPLE 3

Preparation of Salt Derivatives from Acids

This example illustrates methods for preparing the pharmaceutically acceptable salts of the invention. To prepare a sodium salt, for example, of a compound of formula (1), (2) or (3) where $R_1$ is $CO_2H$, for example (Z)-(3'S,1S,2R,3S,6S)-4-[2-(3'-hydroxy-3'-cyclohexylprop-1'-ynyl)-3-hydroxy-6-methoxybicyclo[4.2.0]oct-7-ylidene]butanoic acid, the acid is dissolved in methanol and one molar equivalent of sodium hydroxide dissolved in water is added. The solvent is removed under reduced pressure and the residue recrystallized from a suitable solvent, for example ethyl acetate-methanol, to furnish the desired sodium salt.

The sodium salts of other compounds of formula (1), (2) or (3), where $R_1$ is $CO_2H$, made as shown in Example 1, are similarly prepared using the above procedure. Other salts are similarly prepared, replacing sodium hydroxide with the desired base.

EXAMPLE 4

Preparation of Acid Derivatives from Salts

The sodium salt of (Z)-(3'S,1S,2R,3S,6S)-4-[2-(3'-hydroxy-3'-cyclohexylprop-1'-ynyl)-3-hydroxy-6- methoxybicyclo[4.2.0]oct-7-ylidene]butanoic acid, prepared as shown in Example 3, is suspended in ethyl acetate and stirred with 2 molar equivalents of dilute aqueous sulfuric acid until the salt is completely dissolved. The organic layer is separated, washed with water, dried over magnesium sulfate and evaporated to give (Z)-(3′S,1S,2R,3S,6S)-4-[2-(3′-hydroxy-3′-cyclohexylprop-1′-ynyl)-3-hydroxy-6-methoxybicyclo[4.2.0]oct-7-ylidene]butanoic acid.

Similarly, other salts of compounds of formula (1), (2) or (3) where $R_1$ is $CO_2H$ are converted to the corresponding free acid.

EXAMPLE 5

A. Preparation of methyl (Z)-(3′S,1S,2R,3S,6S)-4-[2-(3′-hydroxy-3′-cyclohexylprop-1′-ynyl)-3-hydroxy-6-methoxybicyclo[4.2.0]oct-7-ylidene]butyrate A solution of (Z)-(3′S,1S,2R,3S,6S)-4-[2-(3′-hydroxy-3′-cyclohexylprop-1′-ynyl)-3-hydroxy-6-methoxybicyclo[4.2.0]oct-7-ylidene]butyric acid, prepared as shown in Example 1 or Example 2, is dissolved in ether and treated with an ethereal solution containing a molar excess of diazomethane. The yellow mixture is held at room temperature for 2 hours, then acetic acid is added dropwise until the remaining color is discharged. Solvent is removed by evaporation under reduced pressure, and the virtually pure residue so obtained is given a final purification by chromatography on silica gel, eluting with 4% methanol in methylene chloride to furnish the title compound.

B. In similar fashion but substituting higher diazoalkanes for the diazomethane employed in the preceeding example, the corresponding higher alkyl esters of the starting acid are prepared. The requisite diazoalkanes are known. They may be prepared, by conventional methods, e.g. as described in Org.Reactions, 8, 389–94, (1954).

Furthermore, by employing the procedure and diazoalkane reagents of this Example but substituting the other acid products of formula (1), (2) or (3) prepared according to Example 1 for the starting material utilized above, the corresponding alkyl esters of each acid product of formula (1), (2) or (3) are prepared.

EXAMPLE 6

Preparation of Free Carboxylic Acids by Hydrolysis of the Corresponding Ester

This Example describes preparation of the carboxylic acids of our invention of formula (1), (2) or (3) by hydrolysis of their corresponding alkyl esters. Hydrolysis may be carried out employing a wide variety of organic and/or inorganic bases under conventional and well-known reaction conditions. The following procedure is given for illustrative purposes only and is not intended to be limiting in any sense.

A solution of the methyl ester (0.05 g) of (Z)-(3′S,1S,2R,3S,6S)-4-[2-(3′-hydroxy-3′-cyclohexylprop-1′-ynyl)-3-hydroxy-6-methoxybicyclo[4.2.0]oct-7-ylidene]butyric acid, prepared according to Example 5, in 3 ml of methanol is purged with argon and stirred under an argon atmosphere while 0.5 ml of in aqueous NaOH is added. Stirring is continued for 4 hours at ambient temperature, followed by evaporation of most of the solvent under reduced pressure. The concentrate is diluted with 10 ml of $H_2O$ and, after adjusting the pH to between 5.5 and 6.5, extracted with 3 portions of methylene chloride. The combined extracts are washed with saturated brine, dried over sodium sulfate, and evaporated under reduced pressure to afford the free carboxylic acid, i.e., (Z)-(3′S,1S,2R,3S,6S)-4-[2-(3′-hydroxy-3′-cyclohexylprop-1′-ynyl)-3-hydroxy-6-methoxybicyclo[4.2.0]oct-7-ylidene]butyric acid. Similarly, the other esters prepared from the novel acids of our invention are hydrolysed to furnish the corresponding free acid.

EXAMPLE 7

Compounds Wherein $R_1$ is $CH_2OH$

A. Preparation of methyl Z-(3′S,1S,2R,3S,6S)-4-[2-(3′-tert-butyldimethylsilyloxy-3′-cyclohexylprop-1′-ynyl)-3-tert-butyldimethyl-silyloxy-6-methoxybicyclo[4.2.0]oct-7-ylidene]butyrate and related compounds of Formula (XXIX)

A mixture of 0.52 g of methyl Z-(3′S,1S,2R,3S,6S)-4-[2-(3′-hydroxy-3′-cyclohexylprop-1′-ynyl)-3-hydroxy-6-methoxybicyclo[4.2.0]oct-7-ylidene]butyrate, 0.55 g tert-butyldimethylsilyl chloride, 0.18 g 4-dimethylaminopyridine, 2 ml triethylamine and 10 ml dichloromethane is stirred at 23° C. for 24 hours. After dilution with 20 ml of dichloromethane the mixture is washed with 10 ml water, three 20-ml portions of 1N HCl and 10 ml sat. sodium bicarbonate. After drying over sodium sulfate the solvent is removed to give 0.76 of the title compound.

B.

In similar fashion, substituting other esters of formula (XXVIII) in the procedure of 7A above, the corresponding protected compounds of formula (XXIX) are prepared.

C. Preparation of Z-(3′S,1S,2R,3S,6S)-4-[2-(3′-tert-butyldimethylsilyloxy-3′-cyclohexyl-prop-1′-ynyl)-3-tert-butyldimethyl-silyloxy-6-methoxybicyclo[4.2.0]oct-7-ylidene]butan-1-ol and related compounds of Formula (XXX)

To a stirred mixture of 0.1 g lithium aluminum hydride in 15 ml diethyl ether is added in dropwise fashion a solution of 0.78 g of methyl Z-(3′S,1S,2R,3S,6S)-4-[2-(3′-tert-butyldimethylsilyloxy-3′-cyclohexylprop-1′-ynyl)-3-tert-butyldimethylsilyloxy-6-methoxybicyclo[4.2.0]oct-7-ylidene]butyrate in 5 ml of diethyl ether. This mixture is heated at reflux for 2 h. After cooling the reaction is worked up by sequential dropwise addition of 0.1 ml water, 0.1 ml 15% sodium hydroxide, and 0.3 ml water. The resulting precipitate is removed by filtration. Evaporation of the filtrate gives the title compound.

In a similar manner, but starting instead with other appropriate compounds of Formula (XXIX), prepared according to the method described in paragraph A above, other compounds of Formula (XXX) are prepared.

D. Preparation of Z-(3′S,1S,2R,3S,6S)-4-[2-(3′-hydroxy-3′-cyclohexylprop-1′-ynyl)-3-hydroxy-6-methoxybicyclo[4.2.0]oct-7-ylidene]butan-1-ol and related compounds of Formulas (1), (2) and (3) in which $R_1$ is $CH_2OH$ To a solution of 0.15 g Z-(3′S,1S,2R,3S,6S)-4-[2-(3′-tert-butyldimethylsilyloxy-3′-cyclohexylprop-1′-ynyl)-3-tert-butyldimethylsilyloxy-6-methoxybicyclo[4.2.-o]oct-7-ylidene]-1-butanol in 3 ml tetrahydrofuran is added 5 ml of a 1M solution of tetrabutylammonium fluoride in tetrahydrofuran. After 12 hours at 23° C. the solution is diluted with 20 ml water and the product is extracted into diethyl ether. Evaporation of the solvent and purification of the product using silica gel flash chromatography with ethyl acetate-hexane (1:1) gives the title compound.

In like manner, but starting with other compounds of Formula (XXX), preparation of which is described in Example 7C above, other compounds of formula (1), (2) or (3) are prepared.

EXAMPLE 8

Preparation of Z-(3'S,1S,2R,3S,6S)-4-[2-(3'-hydroxy-3'-cyclohexylprop-1'-ynyl)-3-hydroxy-6-methoxybicyclo[4.2.0]oct-7-ylidene]butan-1-al and related compounds of Formulas (1), (2) or (3) wherein $R_1$ is CHO A. To a stirred mixture of 0.25 g pyridinium chlorochromate in 7 ml dichloromethane is added a solution of 0.2 g of Z-(3'S,1S,2R,3S,6S)-4-[2-(3'-tert-butyldimethylsilyloxy-3'-cyclohexylprop-1'-ynyl)-3-tert-butyldimethylsilyloxy-6-methoxybicyclo[4.2.0]oct-7-ylidene]-1-butanol, prepared according to Example 7, in 3 ml dichloromethane. After 4 hours at 23° C. the solution is decanted from the precipitate and filtered through 10 g Florisil with dichloromethane. The filtrate is concentrated to a residue, which is dissolved in 3 ml tetrahydrofuran. To this solution is added 2 ml of a 1M solution of tetrabutylammonium fluoride in tetrahydrofuran. After 16 hours at 23° C. this solution is diluted with 20 ml water and the product extracted into diethyl ether. Evaporation of solvent followed by silica gel flash chromatography using ethyl acetate-hexane (30:70) gives the title compound.

B. In a similar manner, starting with other compounds of formula (XXX) and following the procedures of Example 7A above, other compounds of formula (1), (2) or (3) where $R_1$ is CHO are prepared.

EXAMPLE 9

Preparation of p-Benzamidophenyl Z-(3'S,1S,2R,3S,6S)-4-[2-(3'-hydroxy-3'-cyclohexylprop-1'-ynyl)-3-hydroxy-6-methoxybicyclo[4.2.0]oct-7-ylidene]butyrate, and related compounds of Formulas (1), (2) and (3) in which $R_1$ is $CO_2R$ A. A solution of Z-(3'S,1S,2R,3S,6S)-4-[2-(3'-hydroxy-3'-cyclohexylprop-1'-ynyl)-3-hydroxy-6-methoxybicyclo[4.2.0]oct-7-ylidene]butyric acid (35 mg, 0.101 mmol) in acetone (2.7 mL) is treated with triethylamine (28.1 μL, 0.202 mmol). The solution is cooled to −5° C. under $N_2$ and isobutyl chlorocarbonate (27.3 μL, 0.202 mmol) added. After 5 minutes at −5° C., a solution of p-benzamidophenol (109.2 mg, 0.51 mmol) in dry pyridine (1.1 mL) is added. After 3 hours at room temperature, the solvent is removed under vacuum. The residue is extracted with dichloromethane and the solid (excess p-benzamidophenol) is removed by filtration. After evaporation of the solvent, the residue is purified by column chromatography using 30% acetone in hexane to afford the title compound.

B. In like manner, but starting with other appropriate compounds of Formulas (1), (2) or (3) in which $R_1$ is $CO_2H$, and substituting for the p-benzamidophenol other appropriate substituted phenols, other compounds in which $R_1$ is $CO_2R$ are prepared.

EXAMPLE 10

Determination of Inhibition of Platelet Aggregation

Human venous blood from drug-free healthy volunteers is collected into 15 ml-vacutainers and anticoagulated with 0.5 ml of 11.4% sodium citrate. The blood is centrifuged at room temperature for 15 minutes at 150 g in a Sorvall GLC-28 centrifuge and the supernatant platelet-rich plasma (PRP) is collected by aspiration. Platelet-poor plasma (PPP) is prepared by centrifuging the blood from which PRP has been removed at 12,800 g for 3 minutes in an Eppendorf centrifuge at room temperature. Platelet aggregation is carried out by the method of Born (J. Physiology, 168, 178 (1963)) in Payton aggregometers. Platelet aggregation is induced by adding ADP (2–5 nmoles) into 1 ml of PRP containing 10 μl of various concentrations of test compounds or vehicle incubated in the aggregometer cuvette at 37° C. for 5 minutes with the stirring speed set at 500 rpm. Then, for each test compound, a percent inhibition versus concentration curve is drawn on semi-logarithmic paper and the concentration corresponding to 50% inhibition is expressed as the $IC_{50}$ for this compound. All the test compounds (1–2 mg) are prepared as 0.01M stock solutions in 10% ethanol and 59 mM $Na_2CO_3$. Subsequent dilutions are made with water.

EXAMPLE 11

Determination of Antihypertensive Activity

The antihypertensive effects of the prostaglandin-like compounds are evaluated in spontaneously hypertensive rats (SHR/NCrlBR). Under ether anesthesia, femoral arterial and venous cannulae are implanted and the rats are restrained in a supine position. After recovery from the anesthesia, lidocaine is administered. Blood pressures are obtained via the femoral arterial cannula and recorded on a Beckman R611 polygraph. Groups of four rats are studied for each compound. Vehicle is administered at the beginning of the study and compound is intravenously administered at 30 min intervals thereafter, at increasing doses of 1, 3, 10, 30 and 100 μg/Kg. Baseline mean arterial blood pressure is the blood pressure immediately prior to the first dose of the compound. $ED_{20}s$ are calculated from a linear regression of the percent decrease of mean blood pressures following each dose of the compound. The duration of activity is determined based on the recovery to 90% of the control blood pressure following the 100 μg/Kg, i.v., dose.

EXAMPLE 12

| Formulation Ingredient | Composition | |
|---|---|---|
| | Amount mg | Amount (1000 Tablets) |
| Sodium (Z)-(3'S,1S,2R,3S,6S)-4-[2-(3'-hydroxy-3'-cyclohexylprop-1'-ynyl)-3-hydroxy-6-methoxybicyclo[4.2.0]oct-7-ylidene]butyrate | 52.6 | 52.6 Gm |
| Spray Dried Lactose | 200 | 200 Gm |
| Magnesium Stearate | 3 | 3 Gm |

Preparation

The above ingredients are homogeneously mixed and the power mixture then compressed into approximately 256 mg tablets each containing approximately 52.6 mg of the active ingredient.

Similarly, the active ingredient in the above formulation may be replaced by other compounds of formula (1), (2) or (3), or their pharmaceutically acceptable salts or esters, to give a suitable composition.

What we claim is:

1. A compound of formula (1), (2) or (3);

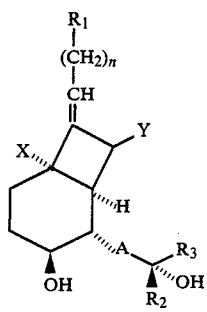 (1)

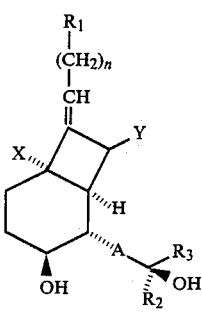 (2)

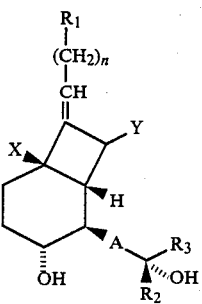 (3)

wherein:

A is —C≡C—, trans —HC=CH—, —CH₂CH₂— or —CH=CHCH₂—;

X is lower alkoxy, hydroxy, or (2,2,2)-trifluoroethoxy;

Y is hydrogen, exo-(lower alkyl) or endo-(lower alkyl);

n is an integer from 2–4;

R₁ is —CH₂OH, —CHO, —CO₂R or —CO₂H, and the olefin formed by the R₁(CH₂)ₙCH= moiety is either (E) or (Z);

R₂ is hydrogen or methyl, or optionally —CH=CH₂ when A is —CH=CHCH₂—; and

R₃ is linear or branched alkyl, alkenyl or alkynyl having 5–10 carbon atoms,

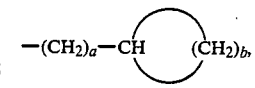

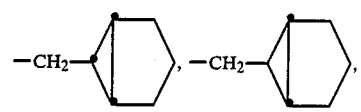

—(CH₂)ₘ-phenyl or CH₂O-phenyl;

in which each phenyl may be optionally substituted with lower alkyl, lower alkoxy, trifluoromethyl, or halogen;

in which:
a is an integer of 0, 1 or 2;
b is an integer of 3–7;
m is an integer of 0, 1 or 2; and
R is

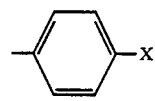

wherein X₁ is

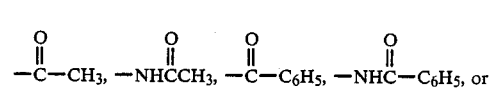

in which each R₄ is independently hydrogen or lower alkyl having 1–6 carbon atoms, or a pharmaceutically acceptable, non-toxic salt or ester thereof.

2. A compound of claim 1 in which the olefin formed by the R₁(CH₂)ₙCH= moiety is (Z), or a pharmaceutically acceptable non-toxic salt or ester thereof.

3. A compound of claim 2 represented by formula (1) or (2), or a pharmaceutically acceptable non-toxic salt or ester thereof.

4. A compound of claim 3 in which X is lower alkoxy and n is 2 or 3, or a pharmaceutically acceptable non-toxic salt or ester thereof.

5. A compound of claim 4 represented by the formula (1) in which A is —C≡C—, or a pharmaceutically acceptable non-toxic salt or ester thereof.

6. A compound of claim 5 in which X is methoxy, R₂ is hydrogen and R₃ is

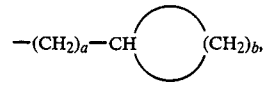

or a pharmaceutically acceptable non-toxic salt or ester thereof.

7. A compound of claim 6 in which a is zero and b is 5, or a pharmaceutically acceptable non-toxic salt or ester thereof.

8. A compound of claim 7 in which R₁ is —CO₂H and Y is hydrogen, or a pharmaceutically acceptable non-toxic salt or ester thereof.

9. The compound of claim 8 in which n is 2, namely (Z)-(3'S,1S,2R,3S,6S)-4-[2-(3'-hydroxy-3'-cyclohexylprop-1'-ynyl)-3-hydroxy-6-methoxybicyclo[4.2.0]oct-7-ylidene]butyric acid, or a pharmaceutically acceptable non-toxic salt or ester thereof.

10. The racemic compound of claim 8 in which n is 2, namely (Z)-(3'SR,1SR,2RS,3SR,6SR)-4-[2-(3'-hydroxy-3'-cyclohexylprop-1'-ynyl)-3-hydroxy-6-methoxybicyclo[4.2.0]oct-7-ylidene]butyric acid, pharmaceutically acceptable non-toxic salt or ester thereof.

11. The compound of claim 8 in which n is 3, namely (Z)-(3'S,1S,2R,3S,6S)-5-[2-(3'-hydroxy-3'-cyclohexylprop-1'-ynyl)-3-hydroxy-6-methoxybicyclo[4.2.0]oct-7-ylidene]pentanoic acid, or a pharmaceutically acceptable non-toxic salt or ester thereof.

12. The racemic compound of claim 8 in which n is 3 namely (Z)-(3'SR,1SR,2RS,3SR,6SR)-5-[2-(3'-hydroxy-3'-cyclohexylprop-1'-ynyl)-3-hydroxy-6-methoxybicyclo[4.2.0]oct-7-ylidene]pentanoic acid, or a pharmaceutically acceptable non-toxic salt or ester thereof.

13. A compound of claim 7 in which $R_1$ is $-CO_2H$ and Y is exo-methyl or endo-methyl, or a pharmaceutically acceptable non-toxic salt or ester thereof.

14. A compound of claim 13 in which Y is exo-methyl, or a pharmaceutically acceptable non-toxic salt or ester thereof.

15. The compound of claim 14 in which n is 2, namely (Z)-(3'S,1S,2R,3S,6S)-4-[2-(3'-hydroxy-3'-cyclohexylprop-1'-ynyl)-3-hydroxy-6-methoxy-8-oxo-methylbicyclo[4.2.0]oct-7-ylidene]butyric acid, or a pharmaceutically acceptable non-toxic salt or ester thereof.

16. The racemic compound of claim 14 in which n is 2, namely (Z)-(3'SR,1SR,2RS,3SR,6SR)-4-[2-(3'-hydroxy-3'-cyclohexylprop-1'-ynyl)-3-hydroxy-6-methoxy-8-exo-methylbicyclo[4.2.0]oct-7-ylidene]butyric acid, or a pharmaceutically acceptable non-toxic salt or ester thereof.

17. The compound of claim 14 in which n is 3, namely (Z)-(3'S,1S,2R,3S,6S)-5-[2-(3'-hydroxy-3'-cyclohexylprop-1'-ynyl)-3-hydroxy-6-methoxy-8-exo-methylbicyclo[4.2.0]oct-7-ylidene]pentanoic acid, or a pharmaceutically acceptable non-toxic salt or ester thereof.

18. The racemic compound of claim 14 in which n is 3, namely (Z)-(3'SR,1SR,2RS,3SR,6SR)-5-[2-(3'-hydroxy-3'-cyclohexylprop-1'-ynyl)-3-hydroxy-6-methoxy-8-exo-methylbicyclo[4.2.0]oct-7-ylidene]pentanoic acid, or a pharmaceutically acceptable non-toxic salt or ester thereof.

19. A compound of claim 13 in which Y is endo-methyl, or a pharmaceutically acceptable non-toxic salt or ester thereof.

20. The compound of claim 19 in which n is 2, namely (Z)-(3'S,1S,2R,3S,6S)-4-[2-(3'-hydroxy-3'-cyclohexylprop-1'-ynyl)-3-hydroxy-6-methoxy-8-endo-methylbicyclo[4.2.0]oct-7-ylidene]butyric acid, or a pharmaceutically acceptable non-toxic salt or ester thereof.

21. The racemic compound of claim 19 in which n is 2, namely (Z)-(3'SR,1SR,2RS,3SR,6SR)-4-[2-(3'-hydroxy-3'-cyclohexylprop-1'-ynyl)-3-hydroxy-6-methoxy-8-endo-methylbicyclo[4.2.0]oct-7-ylidene]butyric acid, or a pharmaceutically acceptable non-toxic salt or ester thereof.

22. The compound of claim 19 in which n is 3, namely (Z)-(3'S,1S,2R,3S,6S)-5-[2-(3'-hydroxy-3'-cyclohexylprop-1'-ynyl)-3-hydroxy-6-methoxy-8-endo-methylbicyclo[4.2.0]oct-7-ylidene]pentanoic acid, or a pharmaceutically acceptable non-toxic salt or ester thereof.

23. The racemic compound of claim 19 in which n is 3, namely (Z)-(3'SR,1SR,2RS,3SR,6SR)-5-[2-(3'-hydroxy-3'-cyclohexylprop-1'-ynyl)-3-hydroxy-6-methoxy-8-endo-methylbicyclo[4.2.0]oct-7-ylidene]pentanoic acid, or a pharmaceutically acceptable non-toxic salt or ester thereof.

24. A compound of claim 4 in which A is trans $-CH=CH-$, or a pharmaceutically acceptable non-toxic salt or ester thereof.

25. A compound of claim 24 in which X is methoxy, Y is hydrogen and $R_3$ is

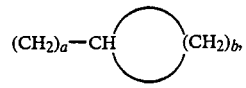

or a pharmaceutically acceptable non-toxic salt or ester thereof.

26. A compound of claim 25 in which a is zero and b is 5, or a pharmaceutically acceptable non-toxic salt or ester thereof.

27. A compound of claim 26 in which n is 2 and $R_1$ is $-CO_2H$, or a pharmaceutically acceptable non-toxic salt or ester thereof.

28. The compound of claim 27, represented by the formula (1), namely (Z)-(3'S,1S,2S,3S,6S)-4-[2-(3'-hydroxy-3'-cyclohexylprop-(1'E)-enyl)-3-hydroxy-6-methoxybicyclo[4.2.0]oct-7-ylidene]butyric acid, or a pharmaceutically acceptable non-toxic salt or ester thereof.

29. The racemic compound of claim 27, represented by the formula (I) namely (Z)-(3'SR,1SR,2SR,3SR,6SR)-4-[2-(3'-hydroxy-3'-cyclohexylprop-(1'E)-enyl)-3-hydroxy-6-methoxybicyclo[4.2.0]oct-7-ylidene]butyric acid, or a pharmaceutically acceptable non-toxic salt or ester thereof.

30. The compound of claim 27, represented by the formula (2), namely (Z)-(3'R,1S,2S,3S,6S)-4-[2-(3'-hydroxy-3'-cyclohexylprop-(1'E)-enyl)-3-hydroxy-6-methoxybicyclo[4.2.0]oct-7-ylidene]butyric acid, or a pharmaceutically acceptable non-toxic salt or ester thereof.

31. The racemic compound of claim 27, represented by the formula (2) namely (Z)-(3'RS,1SR,2SR,3SR,6SR)-4-[2-(3'-hydroxy-3'-cyclohexylprop-(1'-E)-enyl)-3-hydroxy-6-methoxybicyclo[4.2.0]oct-7-ylidene]butyric acid, or a pharmaceutically acceptable non-toxic salt or ester thereof.

32. The compound of claim 1, in which X is methoxy and A is $-CH_2CH_2-$, or a pharmaceutically acceptable non-toxic salt or ester thereof.

33. The compound of claim 1, in which X is methoxy and A is $-CH=CHCH_2-$, or a pharmaceutically acceptable non-toxic salt or ester thereof.

34. A method for treating cardiovascular disorders in mammals which comprises administering a therapeutically effective amount of a compound of claim 1, or a pharmaceutically acceptable non-toxic salt or ester thereof, to a subject in need of such treatment.

35. The method of claim 34 in which the disorder is atherosclerosis.

36. The method of claim 34 in which the disorder involves a thrombotic condition.

37. The method of claim 34 in which the disorder involves a vasospastic condition.

38. The method of claim 34 in which the disorder is hypertension.

39. The method of claim 34 in which the disorder is elevated cholesterol levels.

40. A pharmaceutical composition containing at least one suitable pharmaceutical excipient and a compound of claim 1 or a pharmaceutically acceptable, non-toxic salt or ester thereof.

41. The compound of claim 32, represented by the formula (1) in which the olefin formed by the $R_1(CH_2)_nCH=$ moiety is (Z), wherein $R_1$ is $-CO_2H$, n is 1, $R_2$ and Y are hydrogen and $R_3$ is cyclohexyl, namely (3'R,1S,2S,3S,6S)-6-[2-(3'-hydroxy-3'-cyclohexylprop-1'-yl)-3-hydroxy-6-methoxybicyclo[4.2.0]oct-7-ylidene]butanoic acid, or a pharmaceutically acceptable non-toxic salt or ester thereof.

* * * * *